United States Patent
Dominguez et al.

(10) Patent No.: US 10,765,764 B2
(45) Date of Patent: *Sep. 8, 2020

(54) PROBES FOR IMAGING HUNTINGTIN PROTEIN

(71) Applicant: CHDI Foundation, Inc., New York, NY (US)

(72) Inventors: Celia Dominguez, Los Angeles, CA (US); John Wityak, Carlsbad, CA (US); Jonathan Bard, New York, NY (US); Christopher John Brown, Abingdon (GB); Michael Edward Prime, Swindon (GB); Peter David Johnson, Abingdon (GB); Thomas Martin Krulle, Oxford (GB); Daniel Clark-Frew, Wantage (GB); Duane Higgins, Oxford (GB); Matthew Robert Mills, Wantage (GB); Richard Waldron Marston, Wantage (GB); Samuel Coe, Northampton (GB); Samantha Brown, Bath (GB); Sarah Hayes, Wantage (GB)

(73) Assignee: CHDI Foundation, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/172,425

(22) Filed: Oct. 26, 2018

(65) Prior Publication Data

US 2019/0167821 A1    Jun. 6, 2019

Related U.S. Application Data

(63) Continuation of application No. 15/249,223, filed on Aug. 26, 2016, now Pat. No. 10,137,211.

(60) Provisional application No. 62/211,118, filed on Aug. 28, 2015.

(51) Int. Cl.
| | |
|---|---|
| *A61K 51/04* | (2006.01) |
| *C07D 513/04* | (2006.01) |
| *C07D 487/04* | (2006.01) |
| *C07D 513/14* | (2006.01) |
| *C07B 59/00* | (2006.01) |

(52) U.S. Cl.
CPC ...... *A61K 51/0455* (2013.01); *A61K 51/0459* (2013.01); *C07B 59/002* (2013.01); *C07D 487/04* (2013.01); *C07D 513/04* (2013.01); *C07D 513/14* (2013.01)

(58) Field of Classification Search
CPC ............ A61K 51/0455; A61K 51/0459; C07B 59/002; C07D 513/04; C07D 513/14; C07D 487/04

See application file for complete search history.

(56) References Cited

U.S. PATENT DOCUMENTS

| | | |
|---|---|---|
| 5,639,756 A | 6/1997 | Anisimova et al. |
| 6,642,264 B1 | 11/2003 | Hayashibe et al. |
| 6,676,926 B2 | 1/2004 | Dinter et al. |
| 8,153,796 B2 | 4/2012 | Dubois et al. |
| 9,067,948 B2 | 6/2015 | Harriman et al. |
| 10,137,211 B2 | 11/2018 | Dominguez et al. |
| 2010/0098634 A1 | 4/2010 | Kolb et al. |
| 2012/0070374 A1 | 3/2012 | Gjermund et al. |
| 2013/0302248 A1 | 11/2013 | Gangadharmath et al. |
| 2016/0016914 A1 | 1/2016 | Ladziata et al. |
| 2017/0281804 A1 | 10/2017 | Dominguez et al. |
| 2017/0283436 A1 | 10/2017 | Dominguez et al. |
| 2017/0283439 A1 | 10/2017 | Dominguez et al. |
| 2017/0292150 A1 | 10/2017 | Dominguez et al. |

FOREIGN PATENT DOCUMENTS

WO    WO 2007/086800    8/2007

OTHER PUBLICATIONS

Dianov, Pharm. Chem. Journal, 2007, 41(6), p. 308-9. (Year: 2007).*
Clements-Jewery, J. Med. Chem., 1988, 31, p. 1220-1226. (Year: 1988).*
Clements-Jewery et al., (Imidazo[1,2-a]pyrimidin-2-yl)phenylmethanones and related compounds as potential nonsedative anxiolytics. J Med Chem. Jun. 1988;31 (6):1220-6.
International Preliminary Report on Patentability dated Mar. 6, 2018 for PCT/US2011/021890, 6 pages.
International Search Report and Written Opinion dated Nov. 14, 2016 for PCT/US2016/049112. 12 pages.
Yanamoto, et al. Radiosynthesis and evaluation of [11C]YM-202074 as a PET ligand for imaging the metabotropic glutamate receptor type 1. Nucl Med Biol. Jul. 2010;37(5):615-24.
Yousefi et al. A Novel (18)F-Labeled Imidazo[2,1-b]benzothiazole (IBT) for High Contrast PET Imaging of β-Amyloid Plaques. ACS Med Chem Lett. Jul. 2011;2(9):673-7.
Yousefi, et al. Synthesis and evaluation of 11C-labeled imidazo[2,1-b]benzothiazoles (IBTs) as PET tracers for imaging β-amyloid plaques in Alzheimer's disease. J Med Chem. Feb. 2011;54(4):949-56.

(Continued)

*Primary Examiner* — Michael G. Hartley
*Assistant Examiner* — Leah H Schlientz
(74) *Attorney, Agent, or Firm* — Sheppard Mullin Richter & Hampton LLP

(57) ABSTRACT

Provided are imaging agents comprising a compound of Formula I, or a pharmaceutically acceptable salt thereof, and methods of their use.

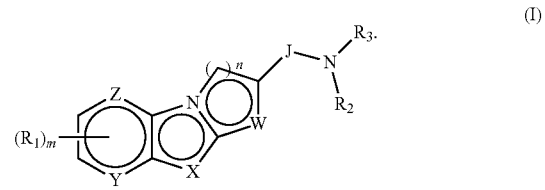

27 Claims, 4 Drawing Sheets

(56) References Cited

OTHER PUBLICATIONS

Extended European Search Report and Opinion dated Apr. 17, 2019 for EP Application No. 16842715.1. 12 pages.

* cited by examiner

R6/2 Mouse ARG

8TR  HPC total binding

NSB

WT Mouse ARG

8TR  HPC total binding

NSB

PROBES FOR IMAGING HUNTINGTIN PROTEIN

CROSS-REFERENCE TO RELATED APPLICATIONS

This application is a continuation of U.S. patent application Ser. No. 15/249,223, filed Aug. 26, 2016, which claims the benefit under 35 U.S.C. § 119(e) to U.S. Provisional Application Ser. No. 62/211,118, filed on Aug. 28, 2015, each of which is hereby incorporated by reference in their entirety.

FIELD

The present disclosure relates to imaging agents that bind to abnormalities of the HTT protein with high sensitivity and specificity for molecular imaging and methods of use of such imaging agents.

BACKGROUND

The advent of molecular imaging approaches such as positron emission tomography (PET) and single photon emission computed tomography (SPECT) has enabled measurements of molecular and cellular mechanisms throughout the body in preclinical and clinical settings. Such measurements have widespread diagnostic utility and their use for evaluation of treatment responses and to assist drug development is expanding rapidly. The recent introduction of high-resolution molecular imaging technology is considered by many experts as a major breakthrough that will potentially lead to a revolutionary paradigm shift in health care and revolutionize clinical practice.

PET involves the administration to a subject of a positron-emitting radionuclide tracer followed by detection of the positron emission (annihilation) events in the body. The radionuclide tracer is typically composed of a targeting molecule having incorporated therein one or more types of positron-emitting radionuclides.

Many new molecular probes labeled with positron-emitting radionuclides and associated PET imaging assays are under development to target, detect, visualize, and quantify various extracellular and intracellular molecules and processes associated with diseases such as cancer, heart disease, and neurological disorders. For instance, several types of agents have been synthesized and evaluated for imaging amyloid β (Aβ) plaques in patients with Alzheimer's disease (AD) including, arylbenzothiazoles, stilbenes, imidazopyridines, pyridylbenzothiazoles, pyridylbenzoxazoles and pyridylbenzofurans (Swahn et al., *Bioorganic & Medicinal Chemistry Letters*, 20 (2010) 1976-1980). Furthermore, styrylbenzimidazole (SBIM) derivatives have been developed as agents for imaging neurofibrillary tangles (NFT), composed of hyperphosphorylated tau protein, in patients with AD. In binding experiments using recombinant tau and amyloid $β_{1-42}$ ($Aβ_{1-42}$) aggregates, 4-[(E)-2-(6-iodo-1H-benzimidazol-2-yl)ethenyl]-N,N-dimethylaniline (SBIM-3) showed higher affinity for the tau aggregates than $Aβ_{1-42}$ aggregates (ratio of $K_d$ values was 2.73). In in vitro autoradiography and fluorescent staining, [$^{125}$I]SBIM-3 (or SBIM-3) bound NFT in sections of AD brain tissue. In biodistribution experiments using normal mice, all [$^{125}$I]SBIM derivatives showed high initial uptake into (3.20-4.11% ID/g at 2 minutes after the injection) and rapid clearance from (0.12-0.33% ID/g at 60 minutes after the injection) the brain (Matsumura et al., *Bioorganic & Medicinal Chemistry*, 21 (2013) 3356-3362).

Huntington's disease (HD) is an inherited progressive neurodegenerative disorder, characterized by motor, cognitive, and psychiatric deficits as well as neurodegeneration and brain atrophy beginning in the striatum and the cortex and extending to other subcortical brain regions. It belongs to a family of neurodegenerative diseases caused by mutations in which an expanded CAG repeat tract results in long stretches of polyglutamine (polyQ) in the encoded mutant protein. This family also includes dentatorubral-pallidoluysian atrophy (DRPLA), spinal and bulbar muscular atrophy (SBMA) and the spinocerebellar ataxias (SCAs). Apart from their polyQ repeats, the proteins involved are unrelated, and although they are all widely expressed in the central nervous system and peripheral tissues, they lead to characteristic patterns of neurodegeneration.

In HD, the selective neurodegeneration of the γ-aminobutyric acid-releasing spiny-projection neurons of the striatum is predominant, although loss of neurons in many other brain regions has also been reported. In the unaffected population, the number of CAG repeats in the $IT_{15}$ gene that encodes the HD protein huntingtin (HTT protein) varies from 6 to 35. CAG repeats of 36 or more define an HD allele, thereby resulting in translation of a mutant huntingtin protein (mHTT) containing a longer polyQ stretch. This mHTT protein is prone to misfolding and aggregate formation. The length of the CAG expansion is inversely correlated with age of disease onset, with cases of juvenile onset characterized by expansions of more than 60 repeats. HD has a prevalence of 5-10 cases per 100,000 worldwide, which makes it the most common inherited neurodegenerative disorder.

The HTT protein is a 348-kDa multidomain protein that contains a polymorphic glutamine/proline-rich domain at its amino-terminus. The longer polyQ domain of mHTT seems to induce conformational changes in the protein, which causes it to form intracellular aggregates that, in most cases, manifest as nuclear inclusions. However, aggregates can also form outside of the nucleus. mHTT protein is present in the nucleus, cell body, dendrites and nerve terminals of neurons, and is also associated with a number of organelles including the Golgi apparatus, endoplasmic reticulum and mitochondria.

Several clinical trials are investigating means to alleviate or reduce symptoms and slow progression in clinically diagnosed HD. Consistent with other medical conditions, treatments might be ideally initiated at or before the earliest signs of disease. There are at least two primary challenges to the design of clinical trials for pre-HD: selection of participants who are most likely to show measurable change over the course of a clinical trial, and development of outcome measures that are sensitive to interventions and can demonstrate variation over the natural history of pre-HD. In order to meet these and other challenges to preventive clinical trials, indicators of very early disease are required.

In view of the central role of the accumulation of aggregated forms of HTT protein (i.e. mHTT) in the pathogenesis of HD, there is a need for molecular probes that bind to such abnormalities with high sensitivity and specificity for molecular imaging in the living subject using PET. The compounds described herein meet this and other needs.

SUMMARY

Provided is an imaging agent comprising a compound of Formula I:

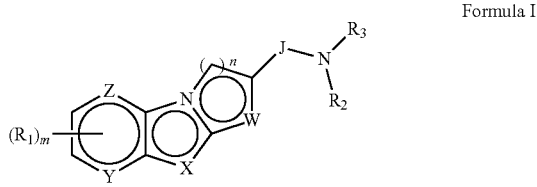

Formula I or a pharmaceutically acceptable salt thereof, wherein
m is 0, 1, or 2;
n is 1 or 2;
J is C(=O) or —CH—;
X is S or N;
Y is CH or N;
Z is CH or N;
W is N or S;
for each occurrence, $R_1$ is independently chosen from halo, lower alkoxy, hydroxy, aryl, heteroaryl, cycloalkoxy, or lower alkyl, wherein the lower alkoxy, cycloalkoxy, lower alkyl, aryl, or heteroaryl are each optionally substituted with one, two, or three groups independently selected from lower alkoxy, alkenyl, —$NR_4R_5$, halo, or heteroaryl optionally substituted with one to three lower alkoxy;
$R_2$ is hydrogen or lower alkyl; and
$R_3$ is alkyl, aryl, aralkyl, heterocycloalkyl, heterocycloalkenyl, heteroaryl, or heteroaralkyl, each of which is optionally substituted with one, two, or three groups independently chosen from hydroxy, lower alkoxy optionally substituted with lower alkoxy or halo, lower alkyl optionally substituted with halo, halo, heteroaryl, —$(CH_2)NR_4R_5$, oxo, cyano, or —C(O)—$NR_4R_5$, or
$R_2$ and $R_3$ taken together with the nitrogen to which they are bound form a heterocycloalkyl ring, optionally substituted with one, two, or three groups independently chosen from hydroxy, lower alkoxy, lower alkyl, halo, or —C(O)—$NR_4R_5$;
t is 0, 1, or 2;
each $R_4$ is independently chosen from hydrogen or lower alkyl;
each $R_5$ is independently chosen from hydrogen or lower alkyl; or
$R_4$ and $R_5$ taken together with the nitrogen to which they are bound form a heterocycloalkyl ring, optionally substituted with one, two, or three groups independently chosen from hydroxy, lower alkoxy, lower alkyl, halo, or —C(O)—$NR_6R_7$;
each $R_6$ is independently hydrogen or lower alkyl; and
each $R_7$ is independently hydrogen or lower alkyl;
wherein the compound of Formula I, or a pharmaceutically acceptable salt thereof, is labeled with one or more positron-emitting radionuclides.

Also provided is a method of generating diagnostic images in an individual comprising administering an effective amount of an imaging agent described herein to an individual, and generating an image of at least a part of said individual.

DETAILED DESCRIPTION

Figure 1A:
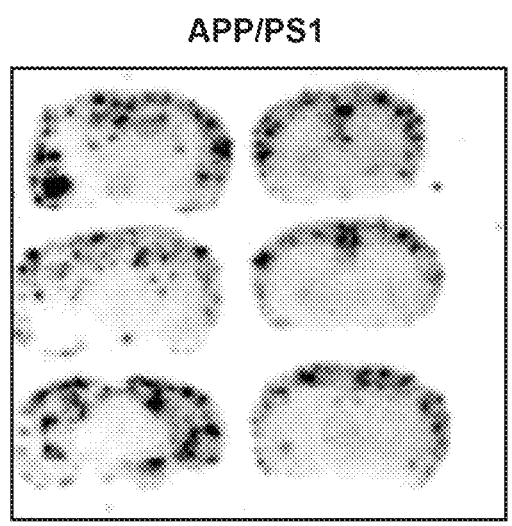
FIG. 1A shows that Aβ aggregates are visible in the 12-month old heterozygous, APP/PS1 mouse brain after incubation with 1 nM 10-[$^3$H]-methoxy-N-(pyridin-3-yl)-7-thia-2,5-diazatricyclo[6.4.0.0$^{2,6}$]dodeca-1(12),3,5,8,10-pentaene-4-carboxamide.

As used in the present specification, the following words, phrases and symbols are generally intended to have the meanings as set forth below, except to the extent that the context in which they are used indicates otherwise. The following abbreviations and terms have the indicated meanings throughout:

A dash ("—") that is not between two letters or symbols is used to indicate a point of attachment for a substituent. For example, —$CONH_2$ is attached through the carbon atom.

As used herein the terms "group", "radical" or "fragment" refer to a functional group or fragment of a molecule attachable to a bond or other fragments of molecules.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

When a moiety is defined as being optionally substituted, it may be substituted as itself or as part of another moiety. For example, if RX is defined as "$C_{1-6}$ alkyl or $OC_{1-6}$ alkyl, wherein $C_{1-6}$ alkyl is optionally substituted with halogen", then both the $C_{1-6}$ alkyl group alone and the $C_{1-6}$ alkyl that makes up part of the $OC_{1-6}$ alkyl group may be substituted with halogen.

The term "alkyl" encompasses straight chain and branched chain having the indicated number of carbon atoms, usually from 1 to 20 carbon atoms, for example 1 to 8 carbon atoms, such as 1 to 6 carbon atoms. For example C1-C6 alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. When an alkyl residue having a specific number of carbons is named, all geometric isomers having that number of carbons are intended to be encompassed; thus, for example, "butyl" is meant to include n-butyl, sec-butyl, isobutyl and tert-butyl; "propyl" includes n-propyl and isopropyl. "Lower alkyl" refers to alkyl groups having 1 to 6 carbons.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, iso-pentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to alkoxy groups having 1 to 6 carbons. By "cycloalkoxy" is meant a cycloalkyl group that is likewise attached through an oxygen bridge.

"Alkenyl" refers to an unsaturated branched or straight-chain alkyl group having the indicated number of carbon atoms (e.g., 2 to 8 or 2 to 6 carbon atoms) and at least one carbon-carbon double bond derived by the removal of one molecule of hydrogen from adjacent carbon atoms of the corresponding alkyl. Alkenyl groups include, but are not limited to, ethenyl, propenyl (e.g., prop-1-en-1-yl, prop-2-en-1-yl) and butenyl (e.g., but-1-en-1-yl, but-1-en-3-yl, but-3-en-1-yl). "Lower alkenyl" refers to alkenyl groups having 2 to 6 carbons.

"Alkynyl" refers to an unsaturated branched or straight-chain alkyl group having the indicated number of carbon atoms (e.g., 2 to 8 or 2 to 6 carbon atoms) and at least one carbon-carbon triple bond derived by the removal of two molecules of hydrogen from adjacent carbon atoms of the corresponding alkyl. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl). "Lower alkynyl" refers to alkynyl groups having 2 to 6 carbons.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl" regardless of the point of attachment (e.g., both quinolin-5-yl and quinolin-2-yl are heteroaryl groups). In some instances, aryl is phenyl or naphthyl. In certain instances, aryl is phenyl.

"Aralkyl" refers to "-alkylene-aryl."

Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentenyl and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond derived by the removal of one molecule of hydrogen from adjacent carbon atoms of the corresponding cycloalkyl. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group. Examples of polycyclic cycloalkenyl groups consisting of a cycloalkenyl group fused to an aromatic ring are described below.

The term cyano refers to —CN.

The term "halo" includes fluoro, chloro, bromo, and iodo, and the term "halogen" includes fluorine, chlorine, bromine, and iodine.

"Haloalkyl" includes straight and branched carbon chains having the indicated number of carbon atoms (e.g., 1 to 6 carbon atoms) substituted with at least one halogen atom. In instances wherein the haloalkyl group contains more than one halogen atom, the halogens may be the same (e.g., dichloromethyl) or different (e.g., chlorofluoromethyl). Examples of haloalkyl groups include, but are not limited to, chloromethyl, dichloromethyl, trichloromethyl, fluoroethyl, difluoromethyl, trifluoromethyl, chlorofluoromethyl, 2-fluoroethyl, 2,2-difluoroethyl, 2,2,2-trifluoroethyl, 1,2-difluoroethyl, 2-chloroethyl, 2,2-dichloroethyl, 2,2,2-trichloroethyl, 1,2-dichloroethyl, pentachloroethyl, and pentafluoroethyl.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group.

"Heteroaralkyl" refers to the group "-alkylene-heteroaryl."

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic).

Examples of monocyclic heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl.

When nitrogen is present in a heterocycloalkyl ring, it may, where the nature of the adjacent atoms and groups permits, exist in an oxidized state (i.e., $N^+$—$O^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine S-oxide and thiomorpholine S,S-dioxide.

In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). When nitrogen is present in a heterocycloalkenyl ring, it may, where the nature of the adjacent atoms and groups permits, exist in an oxidized state (i.e., $N^+$—$O^-$). Additionally, when sulfur is present in a heterocycloalkenyl ring, it may, where the nature of the adjacent atoms and groups permits, exist in an oxidized state (i.e., $S^+$—$O^-$ or —$SO_2$—). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group.

The term "hydroxy" refers to —OH.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation $C_1$-$C_4$ alkyl), cycloalkyl, cycloalkenyl, aryl, heterocycloalkyl, heterocycloalkenyl, and heteroaryl, unless otherwise expressly defined, refer respectively to alkyl, cycloalkyl, cycloalkenyl, aryl, heterocycloalkyl, heterocycloalkenyl, and heteroaryl, wherein one or more (such as up to 5, for example, up to 3) hydrogen atoms are replaced by a substituent independently chosen from: —$R^a$, —$OR^b$, —$O(C_1$-$C_2$ alkyl)O— (e.g., methylenedioxy-), —$SR^b$, guanidine (—NHC(=NH)NH$_2$), guanidine wherein one or more of the guanidine hydrogens are replaced with a $C_1$-$C_4$alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from $C_1$-$C_6$ alkyl, cycloalkyl, aryl, heterocycloalkyl, and heteroaryl; $R^b$ is chosen from H, $C_1$-$C_6$ alkyl, aryl, and heteroaryl; and $R^c$ is chosen from hydrogen and $C_1$-$C_4$ alkyl; or $R^b$ and $R^c$, and the nitrogen to which they are attached, form a heterocycloalkyl group; and where each $C_1$-$C_6$ alkyl, cycloalkyl, aryl, heterocycloalkyl, and heteroaryl is optionally substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —N($C_1$-$C_4$ alkyl)($C_1$-$C_4$ alkylheteroaryl), —NH($C_1$-$C_4$ alkylphenyl), cyano, nitro, oxo (as a substituent for heteroaryl), —CO$_2$H, —C(O)OC$_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)C$_1$-$C_4$ alkyl, —C(O)C$_1$-$C_4$ phenyl, —C(O)C$_1$-$C_4$ haloalkyl, —OC(O)C$_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

The term "substituted amino" refers to the group —NHR$^d$ or —NR$^d$R$^d$ where each R$^d$ is independently chosen from: optionally substituted alkyl, optionally substituted cycloalkyl, optionally substituted acyl, optionally substituted aryl, optionally substituted heteroaryl, optionally substituted heterocycloalkyl, alkoxycarbonyl, sulfinyl and sulfonyl, wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:
—$R^a$, —$OR^b$, —$O(C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$CO_2R^b$, —$CONR^bR^c$, —$NR^cCOR^b$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl;

where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —N($C_1$-$C_4$ alkyl)($C_1$-$C_4$ alkylheteroaryl), —NH($C_1$-$C_4$ alkylphenyl), cyano, nitro, oxo (as a substitutent for heteroaryl), —CO$_2$H, —C(O)OC$_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)C$_1$-$C_4$ alkyl, —C(O)C$_1$-$C_4$ phenyl, —C(O)C$_1$-$C_4$ haloalkyl, —OC(O)C$_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

The terms "substituted" alkyl (including without limitation $C_1$-$C_4$ alkyl), cycloalkyl, cycloalkenyl, aryl, heterocycloalkyl, heterocycloalkenyl, and heteroaryl, unless otherwise expressly defined, refer respectively to alkyl, cycloalkyl, cycloalkenyl, aryl, heterocycloalkyl, heterocycloalkenyl, and heteroaryl, wherein one or more (such as up to 5, for example, up to 3) hydrogen atoms are replaced by a substituent independently chosen from: —$R^a$, —$OR^b$, —$O(C_1$-$C_2$ alkyl)O— (e.g., methylenedioxy-), —$SR^b$, guanidine (—NHC(=NH)NH$_2$), guanidine wherein one or more of the guanidine hydrogens are replaced with a $C_1$-$C_4$alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from $C_1$-$C_6$ alkyl, cycloalkyl, aryl, heterocycloalkyl, and heteroaryl; $R^b$ is chosen from H, $C_1$-$C_6$ alkyl, aryl, and heteroaryl; and $R^c$ is chosen from hydrogen and $C_1$-$C_4$ alkyl; or $R^b$ and $R^c$, and the nitrogen to which they are attached, form a heterocycloalkyl group; and where each $C_1$-$C_6$ alkyl, cycloalkyl, aryl, heterocycloalkyl, and heteroaryl is optionally substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —N($C_1$-$C_4$ alkyl)($C_1$-$C_4$ alkylheteroaryl), —NH($C_1$-$C_4$ alkylphenyl), cyano, nitro, oxo (as a substituent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(aryl), —$SO_2$(heteroaryl), —$SO_2$($C_1$-$C_4$ haloalkyl), —$SO_2NH_2$, —$SO_2$NH($C_1$-$C_4$ alkyl), —$SO_2$NH(aryl), —$SO_2$NH(heteroaryl), —$SO_2$(aryl), —$NHSO_2$($C_1$-$C_4$ alkyl), —$NHSO_2$(phenyl), —$NHSO_2$(aryl), —$NHSO_2$(heteroaryl), and —$NHSO_2$($C_1$-$C_4$ haloalkyl).

The term "substituted amino" refers to the group —$NHR^d$ or —$NR^dR^d$ where each $R^d$ is independently chosen from: optionally substituted alkyl, optionally substituted cycloalkyl, optionally substituted acyl, optionally substituted aryl, optionally substituted heteroaryl, optionally substituted heterocycloalkyl, alkoxycarbonyl, sulfinyl and sulfonyl, wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, —O($C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$CO_2R^b$, —$CONR^bR^c$, —$NR^cCOR^b$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl;

where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylene-aryl, —$OC_1$-$C_4$ alkylene-heteroaryl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylenearyl), —N($C_1$-$C_4$ alkyl)($C_1$-$C_4$ alkyleneheteroaryl), —N($C_1$-$C_4$ alkyl)($C_1$-$C_4$ alkylheteroaryl), —NH($C_1$-$C_4$ alkylphenyl), cyano, nitro, oxo (as a substituent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(aryl), —NHC(O)(heteroaryl), —N($C_1$-$C_4$ alkyl)C(O)($C_1$-$C_4$ alkyl), —N($C_1$-$C_4$ alkyl)C(O)(aryl), —N($C_1$-$C_4$ alkyl)C(O)(heteroaryl), —C(O)$C_1$-$C_4$ alkyl, —C(O)$C_1$-$C_6$ aryl, —C(O)heteroaryl, —C(O)$C_1$-$C_4$ haloalkyl, —OC(O)$C_1$-$C_4$ alkyl, —$SO_2$($C_1$-$C_4$ alkyl), —$SO_2$(aryl), —$SO_2$(heteroaryl), —$SO_2$($C_1$-$C_4$ haloalkyl), —$SO_2NH_2$, —$SO_2$NH($C_1$-$C_4$ alkyl), —$SO_2$NH(aryl), —$SO_2$NH(heteroaryl), —$NHSO_2$($C_1$-$C_4$ alkyl), —$NHSO_2$(aryl), —$NHSO_2$(heteroaryl), and —$NHSO_2$($C_1$-$C_4$ haloalkyl).

The term "substituted amino" also refers to the group —$NR^eR^f$ wherein $R^e$ and $R^f$, together with the nitrogen to which they are bound, form an optionally substituted 5- to 7-membered nitrogen-containing, non-aromatic, heterocycle which optionally contains 1 or 2 additional heteroatoms chosen from nitrogen, oxygen, and sulfur.

"Aminocarbonyl" encompasses a group of the formula —(C=O)(optionally substituted amino) wherein substituted amino is as described herein.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. The term "isomers" refers to different compounds that have the same molecular formula. The term "stereoisomers" refers to isomers that differ only in the way the atoms are arranged in space. The term "enantiomers" refers to stereoisomers that are non-superimposable mirror images of each other. A 1:1 mixture of a pair of enantiomers is a "racemic" mixture. The symbol "(±)" may be used to designate a racemic mixture where appropriate. The term "diastereoisomers" refers to stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line.

Where compounds described herein exist in various tautomeric forms, the term "compound" includes all tautomeric forms of the compound. Such compounds also include crystal forms including polymorphs and clathrates. Similarly, the term "salt" includes all tautomeric forms and crystal forms of the compound. The term "tautomers" refers to structurally distinct isomers that interconvert by tautomerization. Tautomerization is a form of isomerization and includes prototropic or proton-shift tautomerization, which is considered a subset of acid-base chemistry. Prototropic tautomerization or proton-shift tautomerization involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Pharmaceutically acceptable forms of the compounds recited herein include pharmaceutically acceptable salts, and mixtures thereof. In some embodiments, the compounds described herein are in the form of pharmaceutically acceptable salts.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, haloalkanoate such as trifluoroacetate, and alkanoate such as acetate, HOOC—$(CH_2)$—COOH where n is 0-4, and like salts. Similarly, pharmaceutically acceptable cations include, but are not limited to sodium, potassium, calcium, aluminum, lithium, and ammonium. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

The term "administering", as used herein in conjunction with a diagnostic agent, such as, for example, a positron-emitter labeled compound described herein, means administering directly into or onto a target tissue or to administer the diagnostic agent systemically to a patient whereby the diagnostic agent is used to image the tissue or a pathology associated with the tissue to which it is targeted. "Administering" a composition may be accomplished by injection, infusion, or by either method in combination with other known techniques.

The term "Curie" (Ci) is a unit of measurement of radioactivity. One Ci refers to that amount of any radioactive material that will decay at a rate of $3.7 \times 10^{10}$ disintegrations per second. The term "milliCurie" (mCi) refers to $10^{-3}$ Curie. It is understood that the International System (SI) unit of radioactivity, the Becquerel, is equal to one disintegration/second. Thus one Becquerel=$2.7 \times 10^{-11}$ Curie.

The term "diagnostic imaging", as used herein, refers to the use of electromagnetic radiation to produce images of internal structures of the human or animal body for the purpose of diagnosis.

The term "effective amount" of a compound, as used herein, is a predetermined amount calculated to achieve a desired effect such as an amount sufficient to enable the acquisition of a desired image of the target organ of an individual. In some instances the target organ is the brain.

The term "huntingtin protein" or "HTT protein", as used herein, refers to the protein encoded by the human huntingtin gene (HTT gene) located on the short (p) arm of chromosome 4 at position 16.3. More precisely, the IT15 gene coding for the HTT protein is located from base pair 3,076,407 to base pair 3,245,686 on chromosome 4.

The term "HTT protein aggregate", as used herein refers to an insoluble fibrous amyloid comprising mis-folded HTT protein molecules.

The term "mutant huntingtin protein" or "mHTT protein" refers to polyglutamine-expanded versions of HTT protein produced due to an expansion of CAG repeats in the hutingtin gene. This mutant form of HTT protein is prone to misfolding and aggregate formation.

The term "β-amyloid aggregate", as used herein refers to an insoluble fibrous amyloid comprising mis-folded β-amyloid protein molecules.

The term "imaging agent", as used herein, refers to a compound as described herein labeled with one or more positron-emitting isotopes or radionuclides. A positron-emitter labeled compound need only be enriched with a detectable isotope to a degree that permits detection with a technique suitable for the particular application.

The term "pathologic process", as used herein, refers to an altered endogenous biological process that may be associated with the aberrant production and/or functioning of proteins, peptides, RNA and other substances associated with such biological process.

The term "PET imaging", as used herein, refers to the use of a positron-emitter labeled compound to produce images of internal structures of the human or animal body.

The term "pharmaceutical composition" refers to a composition comprising at least one imaging agent described herein, whereby the composition is amenable to investigation for a specified, efficacious outcome in a mammal (for example, without limitation, a human) Those of ordinary skill in the art will understand and appreciate the techniques appropriate for determining whether a composition has a desired efficacious outcome based upon the needs of the artisan.

The term "positron-emitting radionuclide", as used herein, refers to a radio-active isotope that exhibits particular type of radioactive decay referred to as β+ decay, in which a proton inside a radionuclide nucleus is converted into a neutron while releasing a positron and an electron neutrino ($v_e$). Some examples of positron-emitting radionuclides include $^{15}O$, $^{13}N$, $^{11}C$, $^{18}F$, $^{76}Br$, and $^{124}I$. These radionuclides have half-lives of about 2, 10, 20, 110 minutes, 16 hours, and 4.2 days respectively.

The term "tomography", as used herein, refers to a process of imaging by sections. The images may be looked at individually, as a series of two-dimensional slices or together, as a computer-generated three-dimensional representation.

Provided is an imaging agent comprising a compound of Formula I:

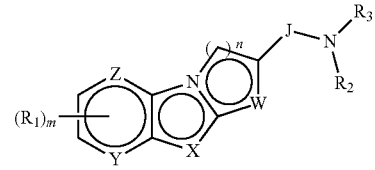

Formula I or a pharmaceutically acceptable salt thereof, wherein
m is 0, 1, or 2;
n is 1 or 2;
J is C(=O) or —$CH_2$—;
X is S or N;
Y is CH or N;
Z is CH or N;
W is N or S;
for each occurrence, $R_1$ is independently chosen from halo, lower alkoxy, hydroxy, aryl, heteroaryl, cycloalkoxy, or lower alkyl, wherein the lower alkoxy, cycloalkoxy, lower alkyl, aryl, or heteroaryl are each optionally substituted with one, two, or three groups independently selected from lower alkoxy, alkenyl, —$NR_4R_5$, halo, or heteroaryl optionally substituted with one to three lower alkoxy;

R$_2$ is hydrogen or lower alkyl; and

R$_3$ is alkyl, aryl, aralkyl, heterocycloalkyl, heterocycloalkenyl, heteroaryl, or heteroaralkyl, each of which is optionally substituted with one, two, or three groups independently chosen from hydroxy, lower alkoxy optionally substituted with lower alkoxy or halo, lower alkyl optionally substituted with halo, halo, heteroaryl, —(CH$_2$)$_t$NR$_4$R$_5$, oxo, cyano, or —C(O)—NR$_4$R$_5$, or R$_2$ and R$_3$ taken together with the nitrogen to which they are bound form a heterocycloalkyl ring, optionally substituted with one, two, or three groups independently chosen from hydroxy, lower alkoxy, lower alkyl, halo, or —C(O)—NR$_4$R$_5$;

t is 0, 1, or 2;

each R$_4$ is independently chosen from hydrogen or lower alkyl;

each R$_5$ is independently chosen from hydrogen or lower alkyl; or

R$_4$ and R$_5$ taken together with the nitrogen to which they are bound form a heterocycloalkyl ring, optionally substituted with one, two, or three groups independently chosen from hydroxy, lower alkoxy, lower alkyl, halo, or —C(O)—NR$_6$R$_7$;

each R$_6$ is independently hydrogen or lower alkyl; and each R$_7$ is independently hydrogen or lower alkyl;

wherein the compound of Formula I, or a pharmaceutically acceptable salt thereof, is labeled with one or more positron-emitting radionuclides.

Some embodiments provide an imaging agent comprising a compound of Formula I(a):

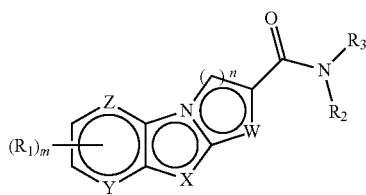

Formula I(a)

or a pharmaceutically acceptable salt thereof, wherein m is 0, 1, or 2;

n is 1 or 2;

X is S or N;

Y is CH or N;

Z is CH or N;

W is N or S;

for each occurrence, R$_1$ is independently chosen from halo, lower alkoxy, hydroxy, aryl, heteroaryl, cycloalkoxy, or lower alkyl, wherein the lower alkoxy, cycloalkoxy, lower alkyl, aryl, or heteroaryl are each optionally substituted with one, two, or three groups independently selected from lower alkoxy, alkenyl, —NR$_4$R$_5$, halo, or heteroaryl optionally substituted with one to three lower alkoxy;

R$_2$ is hydrogen or lower alkyl; and

R$_3$ is alkyl, aryl, aralkyl, heterocycloalkyl, heterocycloalkenyl, heteroaryl, or heteroaralkyl, each of which is optionally substituted with one, two, or three groups independently chosen from hydroxy, lower alkoxy optionally substituted with lower alkoxy or halo, lower alkyl optionally substituted with halo, halo, heteroaryl, —(CH$_2$)$_t$NR$_4$R$_5$, oxo, cyano, or —C(O)—NR$_4$R$_5$, or R$_2$ and R$_3$ taken together with the nitrogen to which they are bound form a heterocycloalkyl ring, optionally substituted with one, two, or three groups independently chosen from hydroxy, lower alkoxy, lower alkyl, halo, or —C(O)—NR$_4$R$_5$;

t is 0, 1, or 2;

each R$_4$ is independently chosen from hydrogen or lower alkyl;

each R$_5$ is independently chosen from hydrogen or lower alkyl; or

R$_4$ and R$_5$ taken together with the nitrogen to which they are bound form a heterocycloalkyl ring, optionally substituted with one, two, or three groups independently chosen from hydroxy, lower alkoxy, lower alkyl, halo, or —C(O)—NR$_6$R$_7$;

each R$_6$ is independently hydrogen or lower alkyl; and each R$_7$ is independently hydrogen or lower alkyl;

wherein the compound of Formula I, or a pharmaceutically acceptable salt thereof, is labeled with one or more positron-emitting radionuclides.

Provided is an imaging agent comprising a compound of Formula I(b):

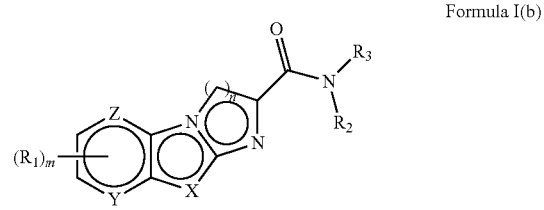

Formula I(b)

or a pharmaceutically acceptable salt thereof, wherein m is 0, 1, or 2;

n is 1 or 2;

X is S or N;

Y is CH or N;

Z is CH or N;

for each occurrence, R$_1$ is independently chosen from lower alkoxy, hydroxy, and lower alkyl;

R$_2$ is chosen from hydrogen and lower alkyl; and

R$_3$ is chosen from aryl, aralkyl, heterocycloalkyl, heteroaryl, and heteroaralkyl, each of which is optionally substituted with one, two, or three groups independently chosen from hydroxy, lower alkoxy, lower alkyl, halo, and —C(O)—NR$_4$R$_5$, or R$_2$ and R$_3$ taken together with the nitrogen to which they are bound form a heterocycloalkyl ring, optionally substituted with one, two, or three groups independently chosen from hydroxy, lower alkoxy, lower alkyl, halo, and —C(O)—NR$_4$R$_5$;

R$_4$ is chosen from hydrogen and lower alkyl;

R$_5$ is chosen from hydrogen and lower alkyl; or

R$_4$ and R$_5$ taken together with the nitrogen to which they are bound form a heterocycloalkyl ring, optionally substituted with one, two, or three groups independently chosen from hydroxy, lower alkoxy, lower alkyl, halo, and —C(O)—NR$_6$R$_7$, R$_6$ is chosen from hydrogen and lower alkyl; and R$_7$ is chosen from hydrogen and lower alkyl;

wherein the compound of Formula I, or a pharmaceutically acceptable salt thereof, is labeled with one or more positron-emitting radionuclides.

In some embodiments, X is S. In some embodiments, X is N.

In some embodiments, Y is CH. In some embodiments, Y is N.

In some embodiments, Z is CH. In some embodiments, Z is N.

In some embodiments, W is N. In some embodiments, W is S.

In some embodiments, m is 0. In some embodiments, m is 1. In some embodiments, m is 2.

In some embodiments, n is 1. In some embodiments, n is 2.

In some embodiments, t is 0. In some embodiments, t is 1. In some embodiments, t is 2.

In some embodiments, for each occurrence, $R_1$ is independently chosen from halo, lower alkoxy, hydroxy, aryl, heteroaryl, or lower alkyl, wherein the lower alkoxy, lower alkyl, aryl, or heteroaryl are each optionally substituted with one to two groups independently selected from lower alkoxy, alkenyl, —$NR_4R_5$, halo, or heteroaryl optionally substituted with one to two lower alkoxy.

In some embodiments, for each occurrence, $R_1$ is independently selected from lower alkoxy, aryl, heteroaryl or lower alkyl, each of which is optionally substituted with one, two, or three groups independently selected from selected from lower alkoxy, alkenyl, —$NR_4R_5$, halo, or heteroaryl optionally substituted with alkoxy.

In some embodiments, for each occurrence, $R_1$ is independently selected from halo, lower alkoxy, hydroxy, or lower alkyl, wherein the lower alkoxy or lower alkyl are each optionally substituted with one, two, or three groups independently selected from alkoxy, alkenyl, —$NR_4R_5$, halo, or heteroaryl optionally substituted with alkoxy.

In some embodiments, for each occurrence, $R_1$ is independently selected from hydroxy, lower alkoxy, or lower alkyl, wherein the lower alkoxy or lower alkyl are each optionally substituted with one, two, or three groups independently selected from alkoxy, alkenyl, —$NR_4R_5$, or halo.

In some embodiments, for each occurrence, $R_1$ is independently selected from lower alkoxy optionally substituted with one, two, or three groups independently selected alkenyl, halo, or heteroaryl optionally substituted with alkoxy.

In some embodiments, for each occurrence, $R_1$ is independently selected from methoxy or hydroxy.

In some embodiments, m is 1 and $R_1$ is methoxy.

In some embodiments, for each occurrence, $R_1$ is independently selected from bromo, methoxy, 2-fluoroethoxy, prop-2-en-1-yloxy, (dimethylamino)methyl, phenyl, 5-methoxypyridin-3-yl, (5-methoxypyridin-2-yl)methoxy, or hydroxy.

In some embodiments, $R_2$ is hydrogen. In some embodiments, $R_2$ is methyl.

In some embodiments, $R_3$ is alkyl, aryl, heterocycloalkyl, heterocycloalkenyl, or heteroaryl, heteroaralkyl, each of which is optionally substituted with one, two, or three groups independently chosen from hydroxy, lower alkoxy optionally substituted with lower alkoxy or halo, halo, lower alkyl optionally substituted with halo, halo, heteroaryl, —$(CH_2)_tNR_4R_5$, cyano, or —C(O)—$NR_4R_5$.

In some embodiments, $R_3$ is heterocycloalkyl, heterocycloalkenyl, or heteroaryl, each of which is optionally substituted with one, two, or three groups independently chosen from hydroxy, lower alkoxy optionally substituted with lower alkoxy, halo, lower alkyl optionally substituted with halo, halo, heteroaryl, —$(CH_2)_tNR_4R_5$, cyano, or —C(O)—$NR_4R_5$.

In some embodiments, $R_3$ is heterocycloalkyl or heteroaryl, each of which is optionally substituted with one, two, or three groups independently chosen from hydroxy, lower alkoxy optionally substituted with lower alkoxy, halo, lower alkyl optionally substituted with halo, halo, heteroaryl, —$(CH_2)_tNR_4R_5$, cyano, or —C(O)—$NR_4R_5$.

In some embodiments, $R_3$ is pyridin-3-yl, pyridin-3-ylmethyl, 1-benzofuran-5-yl, 1H-pyrazol-4-yl, or 6-oxo-1,6-dihydropyridazin-3-yl, each of which is optionally substituted with one, two, or three groups independently chosen from hydroxy, lower alkoxy, lower alkyl, halo, and —C(O)—$NR_4R_5$.

In some embodiments, $R_3$ is pyridin-3-yl, pyridin-3-ylmethyl, 1-benzofuran-5-yl, 1H-pyrazol-4-yl, 6-oxo-1,6-dihydropyridazin-3-yl, pyrimidin-5-yl, ethyl, 6-oxo-1,6-dihydropyridin-3-yl, pyridin-2-yl, pyridin-4-yl, pyrazin-2-yl, 2-oxo-1,2-dihydropyrimidin-5-yl, or phenyl, each of which is optionally substituted with one, two, or three groups independently chosen from hydroxy, lower alkoxy optionally substituted with lower alkoxy, lower alkyl optionally substituted with halo, halo, heteroaryl, —$(CH_2)_tNR_4R_5$, cyano, or —C(O)—$NR_4R_5$.

In some embodiments, $R_3$ is pyridin-3-yl, 5-methoxypyridin-3-yl, 6-methoxypyridin-3-yl, 6-fluoropyridin-3-yl, 6-methylpyridin-3-yl, 6-(methylcarbamoyl)pyridin-3-yl, pyridin-3-ylmethyl, 1-benzofuran-5-yl, 1-methyl-6-oxo-1,6-dihydropyridazin-3-yl, or 1-methyl-1H-pyrazol-4-yl.

In some embodiments, $R_3$ is pyridin-3-yl, 5-methoxypyridin-3-yl, 6-methoxypyridin-3-yl, 6-fluoropyridin-3-yl, 6-methylpyridin-3-yl, 6-(methylcarbamoyl)pyridin-3-yl, pyridin-3-ylmethyl, 1-benzofuran-5-yl, 1-methyl-6-oxo-1,6-dihydropyridazin-3-yl, 1-methyl-1H-pyrazol-4-yl, 2-methylpyrimidin-5-yl, 6-(1H-imidazol-1-yl)pyridin-3-yl, 2-(dimethylamino)ethyl, 2-methoxyethyl, 6-oxo-1,6-dihydropyridin-3-yl, 5-(pyridin-3-yl)pyridin-2-yl, 6-(methylcarbamoyl)pyridin-3-yl, 6-oxo-1,6-dihydropyridazin-3-yl, 2-methoxypyridin-4-yl, 5,6-dimethoxypyridin-3-yl, 3-cyanopyridin-4-yl, 3-cyano-2-methoxypyridin-4-yl, 5-methoxypyridin-2-yl, pyridin-4-yl, pyrazin-2-yl, 3-pyridinyl-1-oxide, 1-methyl-2-oxo-1,2-dihydropyrimidin-5-yl, 3-[(methylamino)methyl]phenyl, 5-(2-methoxyethoxy)pyridin-3-yl, 6-(2-methoxyethoxy)pyridin-3-yl, (pyridin-3-yl)methyl, 2,6-dimethoxypyridin-3-yl, 6-fluoro-5-methoxypyridin-3-yl, 5-(2-fluoroethoxy)pyridin-3-yl, 6-(2-fluoroethoxy)pyridin-3-yl, 1-(2-fluoroethyl)-6-oxo-1,6-dihydropyridazin-3-yl, or 2-methoxypyrimidin-5-yl.

In some embodiments, $R_3$ is pyridin-3-yl, 5-methoxypyridin-3-yl, 6-methoxypyridin-3-yl, 6-fluoropyridin-3-yl, 6-methylpyridin-3-yl, 6-(methylcarbamoyl)pyridin-3-yl, pyridin-3-ylmethyl, 1-benzofuran-5-yl, 1-methyl-6-oxo-1,6-dihydropyridazin-3-yl, 1-methyl-1H-pyrazol-4-yl, 2-methylpyrimidin-5-yl, 6-(1H-imidazol-1-yl)pyridin-3-yl, 2-(dimethylamino)ethyl, 2-methoxyethyl, 6-oxo-1,6-dihydropyridin-3-yl, 5-(pyridin-3-yl)pyridin-2-yl, 6-(methylcarbamoyl)pyridin-3-yl, 6-oxo-1,6-dihydropyridazin-3-yl, 2-methoxypyridin-4-yl, 5,6-dimethoxypyridin-3-yl, 3-cyanopyridin-4-yl, 3-cyano-2-methoxypyridin-4-yl, 5-methoxypyridin-2-yl, pyridin-4-yl, pyrazin-2-yl, 3-pyridinyl-1-oxide, 1-methyl-2-oxo-1,2-dihydropyrimidin-5-yl, 3-[(methylamino)methyl]phenyl, 5-(2-methoxyethoxy)pyridin-3-yl, or 6-(2-methoxyethoxy)pyridin-3-yl.

In some embodiments, $R_2$ and $R_3$ taken together with the nitrogen to which they are bound form a heterocycloalkyl ring is 2,3-dihydro-1H-pyrrolo[2,3-c]pyridin-1-yl, indolin-1-yl, 4,6-dihydropyrrolo[3,4-c]pyrazol-5(1H)-yl, or 4,6-dihydropyrrolo[3,4-b]pyrrol-5(1H)-yl, each of which is optionally substituted with one, two, or three groups independently chosen from hydroxy, lower alkoxy, lower alkyl, and halo.

In some embodiments, each R₄ is independently chosen from hydrogen or $C_{1-3}$alkyl. In some embodiments, each R₄ is independently chosen from hydrogen or methyl.

In some embodiments, each R₅ is independently chosen from hydrogen or $C_{1-3}$alkyl. In some embodiments, each R₅ is independently chosen from hydrogen or methyl.

In some embodiments, each R₆ is independently chosen from hydrogen or $C_{1-3}$alkyl. In some embodiments, each R₆ is independently chosen from hydrogen or methyl.

In some embodiments, each R₇ is independently chosen from hydrogen or $C_{1-3}$alkyl. In some embodiments, each R₇ is independently chosen from hydrogen or methyl.

Also provided is an imaging agent comprising a compound of Formula II(a):

Formula II(a)

or a pharmaceutically acceptable salt thereof, wherein R₁, R₂, R₃, m, n, and X are as described for compounds of Formula I and wherein the compound of Formula II(a), or a pharmaceutically acceptable salt thereof, is labeled with one or more positron-emitting radionuclides.

Also provided is an imaging agent comprising a compound of Formula II(b):

Formula II(b)

or a pharmaceutically acceptable salt thereof, wherein R₁, R₂, R₃, m, n, and X are as described for compounds of Formula I and wherein the compound of Formula II(b), or a pharmaceutically acceptable salt thereof, is labeled with one or more positron-emitting radionuclides.

Also provided is an imaging agent comprising a compound chosen from:
- 10-methoxy-N-(pyridin-3-yl)-7-thia-2,5-diazatricyclo[6.4.0.0$^{2,6}$]dodeca-1(12),3,5,8,10-pentaene-4-carboxamide;
- 10-methoxy-N-(6-methoxypyridin-3-yl)-7-thia-2,5-diazatricyclo[6.4.0.0$^{2,6}$]dodeca-1(12),3,5,8,10-pentaene-4-carboxamide;
- 10-methoxy-N-(pyridin-3-ylmethyl)-7-thia-2,5-diazatricyclo[6.4.0.0$^{2,6}$]dodeca-1(12),3,5,8,10-pentaene-4-carboxamide;
- 10-methoxy-N-methyl-N-(pyridin-3-yl)-7-thia-2,5-diazatricyclo[6.4.0.0$^{2,6}$]dodeca-1(12),3,5,8,10-pentaene-4-carboxamide;
- N-(1-benzofuran-5-yl)-10-methoxy-7-thia-2,5-diazatricyclo[6.4.0.0$^{2,6}$]dodeca-1(12),3,5,8,10-pentaene-4-carboxamide;
- 10-hydroxy-N-(6-methoxypyridin-3-yl)-7-thia-2,5-diazatricyclo[6.4.0.0$^{2,6}$]dodeca-1(12),3,5,8,10-pentaene-4-carboxamide;
- N-(6-methoxypyridin-3-yl)-1,8,10-triazatricyclo[7.4.0.0$^{2,7}$]trideca-2(7),3,5,8,10,12-hexaene-11-carboxamide;
- N-(6-fluoropyridin-3-yl)-1,8,10-triazatricyclo[7.4.0.0$^{2,7}$]trideca-2(7),3,5,8,10,12-hexaene-11-carboxamide;
- 10-hydroxy-N-(pyridin-3-yl)-7-thia-2,5-diazatricyclo[6.4.0.0$^{2,6}$]dodeca-1(12),3,5,8,10-pentaene-4-carboxamide;
- 10-methoxy-N-(5-methoxypyridin-3-yl)-7-thia-2,5-diazatricyclo[6.4.0.0$^{2,6}$]dodeca-1(12),3,5,8,10-pentaene-4-carboxamide;
- 10-methoxy-N-(1-methyl-1H-pyrazol-4-yl)-7-thia-2,5-diazatricyclo[6.4.0.0$^{2,6}$]dodeca-1(12),3,5,8,10-pentaene-4-carboxamide;
- N-(6-fluoropyridin-3-yl)-10-methoxy-7-thia-2,5-diazatricyclo[6.4.0.0$^{2,6}$]dodeca-1(12),3,5,8,10-pentaene-4-carboxamide;
- 10-methoxy-N-(pyridin-3-yl)-7-thia-2,5,9-triazatricyclo[6.4.0.0$^{2,6}$]dodeca-1(12),3,5,8,10-pentaene-4-carboxamide;
- 10-methoxy-N-(5-methoxypyridin-3-yl)-7-thia-2,5,9-triazatricyclo[6.4.0.0$^{2,6}$]dodeca-1(12),3,5,8,10-pentaene-4-carboxamide;
- 10-methoxy-N-[6-(methylcarbamoyl)pyridin-3-yl]-7-thia-2,5-diazatricyclo[6.4.0.0$^{2,6}$]dodeca-1(12),3,5,8,10-pentaene-4-carboxamide;
- 10-methoxy-4-{1H,2H,3H-pyrrolo[2,3-c]pyridine-1-carbonyl}-7-thia-2,5-diazatricyclo[6.4.0.0$^{2,6}$]dodeca-1(12),3,5,8,10-pentaene;
- 10-methoxy-N-(6-methylpyridin-3-yl)-7-thia-2,5-diazatricyclo[6.4.0.0$^{2,6}$]dodeca-1(12),3,5,8,10-pentaene-4-carboxamide;
- 10-methoxy-4-{1-methyl-1H,4H,5H,6H-pyrrolo[3,4-c]pyrazole-5-carbonyl}-7-thia-2,5-diazatricyclo[6.4.0.0$^{2,6}$]dodeca-1(12),3,5,8,10-pentaene; and
- 10-methoxy-N-(1-methyl-6-oxo-1,6-dihydropyridazin-3-yl)-7-thia-2,5-diazatricyclo[6.4.0.0$^{2,6}$]dodeca-1(12),3,5,8,10-pentaene-4-carboxamide, or a pharmaceutically acceptable salt thereof, wherein the compound of Formula I, or a pharmaceutically acceptable salt thereof, is labeled with one or more positron-emitting radionuclides.

Also provided is an imaging agent comprising a compound chosen from:
- 10-methoxy-N-(pyridin-3-yl)-7-thia-2,5-diazatricyclo[6.4.0.0$^{2,6}$]dodeca-1(12),3,5,8,10-pentaene-4-carboxamide;
- 10-methoxy-N-(6-methoxypyridin-3-yl)-7-thia-2,5-diazatricyclo[6.4.0.0$^{2,6}$]dodeca-1(12),3,5,8,10-pentaene-4-carboxamide;
- 10-methoxy-N-(pyridin-3-ylmethyl)-7-thia-2,5-diazatricyclo[6.4.0.0$^{2,6}$]dodeca-1(12),3,5,8,10-pentaene-4-carboxamide;
- 10-methoxy-N-methyl-N-(pyridin-3-yl)-7-thia-2,5-diazatricyclo[6.4.0.0$^{2,6}$]dodeca-1(12),3,5,8,10-pentaene-4-carboxamide;
- N-(1-benzofuran-5-yl)-10-methoxy-7-thia-2,5-diazatricyclo[6.4.0.0$^{2,6}$]dodeca-1(12),3,5,8,10-pentaene-4-carboxamide;
- 10-hydroxy-N-(6-methoxypyridin-3-yl)-7-thia-2,5-diazatricyclo[6.4.0.0$^{2,6}$]dodeca-1(12),3,5,8,10-pentaene-4-carboxamide;
- N-(6-methoxypyridin-3-yl)-1,8,10-triazatricyclo[7.4.0.0$^{2,7}$]trideca-2(7),3,5,8,10,12-hexaene-11-carboxamide;

N-(6-fluoropyridin-3-yl)-1,8,10-triazatricyclo[7.4.0.0$^{2,7}$]trideca-2(7),3,5,8,10,12-hexaene-11-carboxamide;

10-hydroxy-N-(pyridin-3-yl)-7-thia-2,5-diazatricyclo[6.4.0.0$^{2,6}$]dodeca-1(12),3,5,8,10-pentaene-4-carboxamide;

10-methoxy-N-(5-methoxypyridin-3-yl)-7-thia-2,5-diazatricyclo[6.4.0.0$^{2,6}$]dodeca-1(12),3,5,8,10-pentaene-4-carboxamide;

10-methoxy-N-(1-methyl-1H-pyrazol-4-yl)-7-thia-2,5-diazatricyclo[6.4.0.0$^{2,6}$]dodeca-1(12),3,5,8,10-pentaene-4-carboxamide;

N-(6-fluoropyridin-3-yl)-10-methoxy-7-thia-2,5-diazatricyclo[6.4.0.0$^{2,6}$]dodeca-1(12),3,5,8,10-pentaene-4-carboxamide;

10-methoxy-N-(pyridin-3-yl)-7-thia-2,5,9-triazatricyclo[6.4.0.0$^{2,6}$]dodeca-1(12),3,5,8,10-pentaene-4-carboxamide;

10-methoxy-N-(5-methoxypyridin-3-yl)-7-thia-2,5,9-triazatricyclo[6.4.0.0$^{2,6}$]dodeca-1(12),3,5,8,10-pentaene-4-carboxamide;

10-methoxy-N-[6-(methylcarbamoyl)pyridin-3-yl]-7-thia-2,5-diazatricyclo[6.4.0.0$^{2,6}$]dodeca-1(12),3,5,8,10-pentaene-4-carboxamide;

10-methoxy-4-{1H,2H,3H-pyrrolo[2,3-c]pyridine-1-carbonyl}-7-thia-2,5-diazatricyclo[6.4.0.0$^{2,6}$]dodeca-1(12),3,5,8,10-pentaene;

10-methoxy-N-(6-methylpyridin-3-yl)-7-thia-2,5-diazatricyclo[6.4.0.0$^{2,6}$]dodeca-1(12),3,5,8,10-pentaene-4-carboxamide;

10-methoxy-4-{1-methyl-1H,4H,5H,6H-pyrrolo[3,4-c]pyrazole-5-carbonyl}-7-thia-2,5-diazatricyclo[6.4.0.0$^{2,6}$]dodeca-1(12),3,5,8,10-pentaene;

10-methoxy-N-(1-methyl-6-oxo-1,6-dihydropyridazin-3-yl)-7-thia-2,5-diazatricyclo[6.4.0.0$^{2,6}$]dodeca-1(12),3,5,8,10-pentaene-4-carboxamide;

10-methoxy-N-(2-methylpyrimidin-5-yl)-7-thia-2,5-diazatricyclo[6.4.0.0$^{2,6}$]dodeca-1(12),3,5,8,10-pentaene-4-carboxamide;

N-[6-(1H-imidazol-1-yl)pyridin-3-yl]-10-methoxy-7-thia-2,5-diazatricyclo[6.4.0.0$^{2,6}$]dodeca-1(12),3,5,8,10-pentaene-4-carboxamide;

10-methoxy-N-(pyrimidin-5-yl)-7-thia-2,5-diazatricyclo[6.4.0.0$^{2,6}$]dodeca-1(12),3,5,8,10-pentaene-4-carboxamide;

N-[2-(dimethylamino)ethyl]-10-methoxy-7-thia-2,5-diazatricyclo[6.4.0.0$^{2,6}$]dodeca-1(12),3,5,8,10-pentaene-4-carboxamide;

10-methoxy-N-(2-methoxyethyl)-7-thia-2,5-diazatricyclo[6.4.0.0$^{2,6}$]dodeca-1(12),3,5,8,10-pentaene-4-carboxamide;

10-methoxy-N-(6-oxo-1,6-dihydropyridin-3-yl)-7-thia-2,5-diazatricyclo[6.4.0.0$^{2,6}$]dodeca-1(12),3,5,8,10-pentaene-4-carboxamide;

10-methoxy-N-[5-(pyridin-3-yl)pyridin-2-yl]-7-thia-2,5-diazatricyclo[6.4.0.0$^{2,6}$]dodeca-1(12),3,5,8,10-pentaene-4-carboxamide;

10-methoxy-N-(6-oxo-1,6-dihydropyridazin-3-yl)-7-thia-2,5-diazatricyclo[6.4.0.0$^{2,6}$]dodeca-1(12),3,5,8,10-pentaene-4-carboxamide;

5-methoxy-N-(pyridin-3-yl)-1,8,10-triazatricyclo[7.4.0.0$^{2,7}$]trideca-2(7),3,5,8,10,12-hexaene-11-carboxamide;

N-[6-(methylcarbamoyl)pyridin-3-yl]-1,8,10-triazatricyclo[7.4.0.0$^{2,7}$]trideca-2(7),3,5,8,10,12-hexaene-11-carboxamide;

N-(5-methoxypyridin-3-yl)-1,8,10-triazatricyclo[7.4.0.0$^{2,7}$]trideca-2(7),3,5,8,10,12-hexaene-11-carboxamide;

N-(1-methyl-6-oxo-1,6-dihydropyridazin-3-yl)-1,8,10-triazatricyclo[7.4.0.0$^{2,7}$]trideca-2(7),3,5,8,10,12-hexaene-11-carboxamide;

N-(6-oxo-1,6-dihydropyridazin-3-yl)-1,8,10-triazatricyclo[7.4.0.0$^{2,7}$]trideca-2(7),3,5,8,10,12-hexaene-11-carboxamide;

N-(pyridin-3-yl)-1,8,10-triazatricyclo[7.4.0.0$^{2,7}$]trideca-2(7),3,5,8,10,12-hexaene-11-carboxamide;

N-(3-cyanopyridin-4-yl)-1,8,10-triazatricyclo[7.4.0.0$^{2,7}$]trideca-2(7),3,5,8,10,12-hexaene-11-carboxamide;

N-(2-methoxypyridin-4-yl)-1,8,10-triazatricyclo[7.4.0.0$^{2,7}$]trideca-2(7),3,5,8,10,12-hexaene-11-carboxamide;

N-(5,6-dimethoxypyridin-3-yl)-1,8,10-triazatricyclo[7.4.0.0$^{2,7}$]trideca-2(7),3,5,8,10,12-hexaene-11-carboxamide;

5-methoxy-N-(1-methyl-6-oxo-1,6-dihydropyridazin-3-yl)-1,8,10-triazatricyclo[7.4.0.0$^{2,7}$]trideca-2(7),3,5,8,10,12-hexaene-11-carboxamide;

5-methoxy-11-{1-methyl-1H,4H,5H,6H-pyrrolo[3,4-c]pyrazole-5-carbonyl}-1,8,10-triazatricyclo[7.4.0.0$^{2,7}$]trideca-2(7),3,5,8,10,12-hexaene;

4-methoxy-N-(5-methoxypyridin-3-yl)-1,8,10-triazatricyclo[7.4.0.0$^{2,7}$]trideca-2(7),3,5,8,10,12-hexaene-11-carboxamide;

5-methoxy-N-(5-methoxypyridin-3-yl)-1,8,10-triazatricyclo[7.4.0.0$^{2,7}$]trideca-2(7),3,5,8,10,12-hexaene-11-carboxamide;

N-[6-(1H-imidazol-1-yl)pyridin-3-yl]-5-methoxy-1,8,10-triazatricyclo[7.4.0.0$^{2,7}$]trideca-2(7),3,5,8,10,12-hexaene-11-carboxamide;

N-(3-cyanopyridin-4-yl)-5-methoxy-1,8,10-triazatricyclo[7.4.0.0$^{2,7}$]trideca-2(7),3,5,8,10,12-hexaene-11-carboxamide;

N-(6-oxo-1,6-dihydropyridazin-3-yl)-1,8,10-triazatricyclo[7.4.0.0$^{2,7}$]trideca-2(7),3,5,8,10,12-hexaene-11-carboxamide;

N-(3-cyano-2-methoxypyridin-4-yl)-1,8,10-triazatricyclo[7.4.0.0$^{2,7}$]trideca-2(7),3,5,8,10,12-hexaene-11-carboxamide;

5-methoxy-N-(6-methoxypyridin-3-yl)-1,8,10-triazatricyclo[7.4.0.0$^{2,7}$]trideca-2(7),3,5,8,10,12-hexaene-11-carboxamide;

10-methoxy-N-(5-methoxypyridin-2-yl)-7-thia-2,5-diazatricyclo[6.4.0.0$^{2,6}$]dodeca-1(12),3,5,8,10-pentaene-4-carboxamide;

N-(5-methoxypyridin-3-yl)-7-thia-2,5-diazatricyclo[6.4.0.0$^{2,6}$]dodeca-1(12),3,5,8,10-pentaene-4-carboxamide;

10-methoxy-N-(pyridin-4-yl)-7-thia-2,5-diazatricyclo[6.4.0.0$^{2,6}$]dodeca-1(12),3,5,8,10-pentaene-4-carboxamide;

10-methoxy-N-(pyrazin-2-yl)-7-thia-2,5-diazatricyclo[6.4.0.0$^{2,6}$]dodeca-1(12),3,5,8,10-pentaene-4-carboxamide;

3-{10-methoxy-7-thia-2,5-diazatricyclo[6.4.0.0$^{2,6}$]dodeca-1(12),3,5,8,10-pentaene-4-amido}pyridin-1-ium-1-olate;

10-(2-fluoroethoxy)-N-(pyridin-3-yl)-7-thia-2,5-diazatricyclo[6.4.0.0$^{2,6}$]dodeca-1(8),3,5,9,11-pentaene-4-carboxamide;

N-({10-methoxy-7-thia-2,5-diazatricyclo[6.4.0.0$^{2,6}$]dodeca-1(12),3,5,8,10-pentaen-4-yl}methyl)pyridin-3-amine;

10-[(5-methoxypyridin-2-yl)methoxy]-N-(5-methoxypyridin-3-yl)-7-thia-2,5-diazatricyclo[6.4.0.0$^{2,6}$]dodeca-1(12),3,5,8,10-pentaene-4-carboxamide;

N-(1-methyl-6-oxo-1,6-dihydropyridin-3-yl)-1,8,10-triazatricyclo[7.4.0.0$^{2,7}$]trideca-2(7),3,5,8,10,12-hexaene-11-carboxamide;

11-bromo-N-(5-methoxypyridin-3-yl)-7-thia-2,5,9-triazatricyclo[6.4.0.0$^{2,6}$]dodeca-1(12),3,5,8,10-pentaene-4-carboxamide;

N-(1-methyl-6-oxo-1,6-dihydropyridazin-3-yl)-10-(prop-2-en-1-yloxy)-7-thia-2,5-diazatricyclo[6.4.0.0$^{2,6}$]dodeca-1(12),3,5,8,10-pentaene-4-carboxamide;

10-methoxy-N-(5-methoxypyridin-3-yl)-5-thia-2,7-diazatricyclo[6.4.0.0$^{2,6}$]dodeca-1(12),3,6,8,10-pentaene-4-carboxamide;

10-methoxy-N-(1-methyl-6-oxo-1,6-dihydropyridazin-3-yl)-5-thia-2,7-diazatricyclo[6.4.0.0$^{2,6}$]dodeca-1(12),3,6,8,10-pentaene-4-carboxamide;

10-methoxy-N-(2-methylpyrimidin-5-yl)-5-thia-2,7-diazatricyclo[6.4.0.0$^{2,6}$]dodeca-1(8),3,6,9,11-pentaene-4-carboxamide;

N-(1-methyl-2-oxo-1,2-dihydropyrimidin-5-yl)-1,8,10-triazatricyclo[7.4.0.0$^{2,7}$]trideca-2(7),3,5,8,10,12-hexaene-11-carboxamide;

11-methoxy-N-(5-methoxypyridin-3-yl)-7-thia-2,5,9-triazatricyclo[6.4.0.0$^{2,6}$]dodeca-1(12),3,5,8,10-pentaene-4-carboxamide;

11-methoxy-N-(1-methyl-6-oxo-1,6-dihydropyridazin-3-yl)-7-thia-2,5,9-triazatricyclo[6.4.0.0$^{2,6}$]dodeca-1(12),3,5,8,10-pentaene-4-carboxamide;

10-methoxy-N-{3-[(methylaminomethyl]phenyl}-7-thia-2,5-diazatricyclo[6.4.0.0$^{2,6}$]dodeca-1(8),3,5,9,11-pentaene-4-carboxamide;

10-[(dimethylamino)methyl]-N-(5-methoxypyridin-3-yl)-7-thia-2,5-diazatricyclo[6.4.0.0$^{2,6}$]dodeca-1(12),3,5,8,10-pentaene-4-carboxamide;

N-(5-methoxypyridin-3-yl)-10-phenyl-7-thia-2,5-diazatricyclo[6.4.0.0$^{2,6}$]dodeca-1(12),3,5,8,10-pentaene-4-carboxamide;

N,5-bis(5-methoxypyridin-3-yl)-1,8,10-triazatricyclo[7.4.0.0$^{2,7}$]trideca-2(7),3,5,8,10,12-hexaene-11-carboxamide;

N,4-bis(5-methoxypyridin-3-yl)-1,8,10-triazatricyclo[7.4.0.0$^{2,7}$]trideca-2(7),3,5,8,10,12-hexaene-11-carboxamide;

N-[5-(2-methoxyethoxy)pyridin-3-yl]-1,8,10-triazatricyclo[7.4.0.0$^{2,7}$]trideca-2(7),3,5,8,10,12-hexaene-11-carboxamide and N-[6-(2-methoxyethoxy)pyridin-3-yl]-1,8,10-triazatricyclo[7.4.0.0$^{2,7}$]trideca-2(7),3,5,8,10,12-hexaene-11-carboxamide; or or a pharmaceutically acceptable salt thereof, wherein the compound, or a pharmaceutically acceptable salt thereof, is labeled with one or more positron-emitting radionuclides.

Also provided is an imaging agent comprising a compound chosen from:

10-methoxy-N-(pyridin-3-yl)-7-thia-2,5-diazatricyclo[6.4.0.0$^{2,6}$]dodeca-1(12),3,5,8,10-pentaene-4-carboxamide;

10-methoxy-N-(6-methoxypyridin-3-yl)-7-thia-2,5-diazatricyclo[6.4.0.0$^{2,6}$]dodeca-1(12),3,5,8,10-pentaene-4-carboxamide;

10-methoxy-N-(pyridin-3-ylmethyl)-7-thia-2,5-diazatricyclo[6.4.0.0$^{2,6}$]dodeca-1(12),3,5,8,10-pentaene-4-carboxamide;

10-methoxy-N-methyl-N-(pyridin-3-yl)-7-thia-2,5-diazatricyclo[6.4.0.0$^{2,6}$]dodeca-1(12),3,5,8,10-pentaene-4-carboxamide;

N-(1-benzofuran-5-yl)-10-methoxy-7-thia-2,5-diazatricyclo[6.4.0.0$^{2,6}$]dodeca-1(12),3,5,8,10-pentaene-4-carboxamide;

10-hydroxy-N-(6-methoxypyridin-3-yl)-7-thia-2,5-diazatricyclo[6.4.0.0$^{2,6}$]dodeca-1(12),3,5,8,10-pentaene-4-carboxamide;

N-(6-methoxypyridin-3-yl)-1,8,10-triazatricyclo[7.4.0.0$^{2,7}$]trideca-2(7),3,5,8,10,12-hexaene-11-carboxamide;

N-(6-fluoropyridin-3-yl)-1,8,10-triazatricyclo[7.4.0.0$^{2,7}$]trideca-2(7),3,5,8,10,12-hexaene-11-carboxamide;

10-hydroxy-N-(pyridin-3-yl)-7-thia-2,5-diazatricyclo[6.4.0.0$^{2,6}$]dodeca-1(12),3,5,8,10-pentaene-4-carboxamide;

10-methoxy-N-(5-methoxypyridin-3-yl)-7-thia-2,5-diazatricyclo[6.4.0.0$^{2,6}$]dodeca-1(12),3,5,8,10-pentaene-4-carboxamide;

10-methoxy-N-(1-methyl-1H-pyrazol-4-yl)-7-thia-2,5-diazatricyclo[6.4.0.0$^{2,6}$]dodeca-1(12),3,5,8,10-pentaene-4-carboxamide;

N-(6-fluoropyridin-3-yl)-10-methoxy-7-thia-2,5-diazatricyclo[6.4.0.0$^{2,6}$]dodeca-1(12),3,5,8,10-pentaene-4-carboxamide;

10-methoxy-N-(pyridin-3-yl)-7-thia-2,5,9-triazatricyclo[6.4.0.0$^{2,6}$]dodeca-1(12),3,5,8,10-pentaene-4-carboxamide;

10-methoxy-N-(5-methoxypyridin-3-yl)-7-thia-2,5,9-triazatricyclo[6.4.0.0$^{2,6}$]dodeca-1(12),3,5,8,10-pentaene-4-carboxamide;

10-methoxy-N-[6-(methylcarbamoyl)pyridin-3-yl]-7-thia-2,5-diazatricyclo[6.4.0.0$^{2,6}$]dodeca-1(12),3,5,8,10-pentaene-4-carboxamide;

10-methoxy-4-{1H,2H,3H-pyrrolo[2,3-c]pyridine-1-carbonyl}-7-thia-2,5-diazatricyclo[6.4.0.0$^{2,6}$]dodeca-1(12),3,5,8,10-pentaene;

10-methoxy-N-(6-methylpyridin-3-yl)-7-thia-2,5-diazatricyclo[6.4.0.0$^{2,6}$]dodeca-1(12),3,5,8,10-pentaene-4-carboxamide;

10-methoxy-4-{1-methyl-1H,4H,5H,6H-pyrrolo[3,4-c]pyrazole-5-carbonyl}-7-thia-2,5-diazatricyclo[6.4.0.0$^{2,6}$]dodeca-1(12),3,5,8,10-pentaene;

10-methoxy-N-(1-methyl-6-oxo-1,6-dihydropyridazin-3-yl)-7-thia-2,5-diazatricyclo[6.4.0.0$^{2,6}$]dodeca-1(12),3,5,8,10-pentaene-4-carboxamide;

10-methoxy-N-(2-methylpyrimidin-5-yl)-7-thia-2,5-diazatricyclo[6.4.0.0$^{2,6}$]dodeca-1(12),3,5,8,10-pentaene-4-carboxamide;

N-[6-(1H-imidazol-1-yl)pyridin-3-yl]-10-methoxy-7-thia-2,5-diazatricyclo[6.4.0.0$^{2,6}$]dodeca-1(12),3,5,8,10-pentaene-4-carboxamide;

10-methoxy-N-(pyrimidin-5-yl)-7-thia-2,5-diazatricyclo[6.4.0.0$^{2,6}$]dodeca-1(12),3,5,8,10-pentaene-4-carboxamide;

N-[2-(dimethylamino)ethyl]-10-methoxy-7-thia-2,5-diazatricyclo[6.4.0.0$^{2,6}$]dodeca-1(12),3,5,8,10-pentaene-4-carboxamide;

10-methoxy-N-(2-methoxyethyl)-7-thia-2,5-diazatricyclo[6.4.0.0$^{2,6}$]dodeca-1(12),3,5,8,10-pentaene-4-carboxamide;

10-methoxy-N-(6-oxo-1,6-dihydropyridin-3-yl)-7-thia-2,5-diazatricyclo[6.4.0.0$^{2,6}$]dodeca-1(12),3,5,8,10-pentaene-4-carboxamide;

10-methoxy-N-[5-(pyridin-3-yl)pyridin-2-yl]-7-thia-2,5-diazatricyclo[6.4.0.0$^{2,6}$]dodeca-1(12),3,5,8,10-pentaene-4-carboxamide;

10-methoxy-N-(6-oxo-1,6-dihydropyridazin-3-yl)-7-thia-2,5-diazatricyclo[6.4.0.0$^{2,6}$]dodeca-1(12),3,5,8,10-pentaene-4-carboxamide;

5-methoxy-N-(pyridin-3-yl)-1,8,10-triazatricyclo[7.4.0.0$^{2,7}$]trideca-2(7),3,5,8,10,12-hexaene-11-carboxamide;

N-[6-(methylcarbamoyl)pyridin-3-yl]-1,8,10-triazatricyclo[7.4.0.0$^{2,7}$]trideca-2(7),3,5,8,10,12-hexaene-11-carboxamide;

N-(5-methoxypyridin-3-yl)-1,8,10-triazatricyclo[7.4.0.0$^{2,7}$]trideca-2(7),3,5,8,10,12-hexaene-11-carboxamide;

N-(1-methyl-6-oxo-1,6-dihydropyridazin-3-yl)-1,8,10-triazatricyclo[7.4.0.0$^{2,7}$]trideca-2(7),3,5,8,10,12-hexaene-11-carboxamide;

N-(6-oxo-1,6-dihydropyridin-3-yl)-1,8,10-triazatricyclo[7.4.0.0$^{2,7}$]trideca-2(7),3,5,8,10,12-hexaene-11-carboxamide;

N-(pyridin-3-yl)-1,8,10-triazatricyclo[7.4.0.0$^{2,7}$]trideca-2(7),3,5,8,10,12-hexaene-11-carboxamide;

N-(3-cyanopyridin-4-yl)-1,8,10-triazatricyclo[7.4.0.0$^{2,7}$]trideca-2(7),3,5,8,10,12-hexaene-11-carboxamide;

N-(2-methoxypyridin-4-yl)-1,8,10-triazatricyclo[7.4.0.0$^{2,7}$]trideca-2(7),3,5,8,10,12-hexaene-11-carboxamide;

N-(5,6-dimethoxypyridin-3-yl)-1,8,10-triazatricyclo[7.4.0.0$^{2,7}$]trideca-2(7),3,5,8,10,12-hexaene-11-carboxamide;

5-methoxy-N-(1-methyl-6-oxo-1,6-dihydropyridazin-3-yl)-1,8,10-triazatricyclo[7.4.0.0$^{2,7}$]trideca-2(7),3,5,8,10,12-hexaene-11-carboxamide;

5-methoxy-11-{1-methyl-1H,4H,5H,6H-pyrrolo[3,4-c]pyrazole-5-carbonyl}-1,8,10-triazatricyclo[7.4.0.0$^{2,7}$]trideca-2(7),3,5,8,10,12-hexaene;

4-methoxy-N-(5-methoxypyridin-3-yl)-1,8,10-triazatricyclo[7.4.0.0$^{2,7}$]trideca-2(7),3,5,8,10,12-hexaene-11-carboxamide;

5-methoxy-N-(5-methoxypyridin-3-yl)-1,8,10-triazatricyclo[7.4.0.0$^{2,7}$]trideca-2(7),3,5,8,10,12-hexaene-11-carboxamide;

N-[6-(1H-imidazol-1-yl)pyridin-3-yl]-5-methoxy-1,8,10-triazatricyclo[7.4.0.0$^{2,7}$]trideca-2(7),3,5,8,10,12-hexaene-11-carboxamide;

N-(3-cyanopyridin-4-yl)-5-methoxy-1,8,10-triazatricyclo[7.4.0.0$^{2,7}$]trideca-2(7),3,5,8,10,12-hexaene-11-carboxamide;

N-(6-oxo-1,6-dihydropyridazin-3-yl)-1,8,10-triazatricyclo[7.4.0.0$^{2,7}$]trideca-2(7),3,5,8,10,12-hexaene-11-carboxamide;

N-(3-cyano-2-methoxypyridin-4-yl)-1,8,10-triazatricyclo[7.4.0.0$^{2,7}$]trideca-2(7),3,5,8,10,12-hexaene-11-carboxamide;

5-methoxy-N-(6-methoxypyridin-3-yl)-1,8,10-triazatricyclo[7.4.0.0$^{2,7}$]trideca-2(7),3,5,8,10,12-hexaene-11-carboxamide;

10-methoxy-N-(5-methoxypyridin-2-yl)-7-thia-2,5-diazatricyclo[6.4.0.0$^{2,6}$]dodeca-1(12),3,5,8,10-pentaene-4-carboxamide;

N-(5-methoxypyridin-3-yl)-7-thia-2,5-diazatricyclo[6.4.0.0$^{2,6}$]dodeca-1(12),3,5,8,10-pentaene-4-carboxamide;

10-methoxy-N-(pyridin-4-yl)-7-thia-2,5-diazatricyclo[6.4.0.0$^{2,6}$]dodeca-1(12),3,5,8,10-pentaene-4-carboxamide;

10-methoxy-N-(pyrazin-2-yl)-7-thia-2,5-diazatricyclo[6.4.0.0$^{2,6}$]dodeca-1(12),3,5,8,10-pentaene-4-carboxamide;

3-{10-methoxy-7-thia-2,5-diazatricyclo[6.4.0.0$^{2,6}$]dodeca-1(12),3,5,8,10-pentaene-4-amido}pyridin-1-ium-1-olate;

10-(2-fluoroethoxy)-N-(pyridin-3-yl)-7-thia-2,5-diazatricyclo[6.4.0.0$^{2,6}$]dodeca-1(8),3,5,9,11-pentaene-4-carboxamide;

N-({10-methoxy-7-thia-2,5-diazatricyclo[6.4.0.0$^{2,6}$]dodeca-1(12),3,5,8,10-pentaen-4-yl}methyl)pyridin-3-amine;

10-[(5-methoxypyridin-2-yl)methoxy]-N-(5-methoxypyridin-3-yl)-7-thia-2,5-diazatricyclo[6.4.0.0$^{2,6}$]dodeca-1(12),3,5,8,10-pentaene-4-carboxamide;

N-(1-methyl-6-oxo-1,6-dihydropyridin-3-yl)-1,8,10-triazatricyclo[7.4.0.0$^{2,7}$]trideca-2(7),3,5,8,10,12-hexaene-11-carboxamide;

11-bromo-N-(5-methoxypyridin-3-yl)-7-thia-2,5,9-triazatricyclo[6.4.0.0$^{2,6}$]dodeca-1(12),3,5,8,10-pentaene-4-carboxamide;

N-(1-methyl-6-oxo-1,6-dihydropyridazin-3-yl)-10-(prop-2-en-1-yloxy)-7-thia-2,5-diazatricyclo[6.4.0.0$^{2,6}$]dodeca-1(12),3,5,8,10-pentaene-4-carboxamide;

10-methoxy-N-(5-methoxypyridin-3-yl)-5-thia-2,7-diazatricyclo[6.4.0.0$^{2,6}$]dodeca-1(12),3,6,8,10-pentaene-4-carboxamide;

10-methoxy-N-(1-methyl-6-oxo-1,6-dihydropyridazin-3-yl)-5-thia-2,7-diazatricyclo[6.4.0.0$^{2,6}$]dodeca-1(12),3,6,8,10-pentaene-4-carboxamide;

10-methoxy-N-(2-methylpyrimidin-5-yl)-5-thia-2,7-diazatricyclo[6.4.0.0$^{2,6}$]dodeca-1(8),3,6,9,11-pentaene-4-carboxamide;

N-(1-methyl-2-oxo-1,2-dihydropyrimidin-5-yl)-1,8,10-triazatricyclo[7.4.0.0$^{2,7}$]trideca-2(7),3,5,8,10,12-hexaene-11-carboxamide;

11-methoxy-N-(5-methoxypyridin-3-yl)-7-thia-2,5,9-triazatricyclo[6.4.0.0$^{2,6}$]dodeca-1(12),3,5,8,10-pentaene-4-carboxamide;

11-methoxy-N-(1-methyl-6-oxo-1,6-dihydropyridazin-3-yl)-7-thia-2,5,9-triazatricyclo[6.4.0.0$^{2,6}$]dodeca-1(12),3,5,8,10-pentaene-4-carboxamide;

10-methoxy-N-{3-[(methylamino)methyl]phenyl}-7-thia-2,5-diazatricyclo[6.4.0.0$^{2,6}$]dodeca-1(8),3,5,9,11-pentaene-4-carboxamide;

10-[(dimethylamino)methyl]-N-(5-methoxypyridin-3-yl)-7-thia-2,5-diazatricyclo[6.4.0.0$^{2,6}$]dodeca-1(12),3,5,8,10-pentaene-4-carboxamide;

N-(5-methoxypyridin-3-yl)-10-phenyl-7-thia-2,5-diazatricyclo[6.4.0.0$^{2,6}$]dodeca-1(12),3,5,8,10-pentaene-4-carboxamide;

N,5-bis(5-methoxypyridin-3-yl)-1,8,10-triazatricyclo[7.4.0.0$^{2,7}$]trideca-2(7),3,5,8,10,12-hexaene-11-carboxamide;

N,4-bis(5-methoxypyridin-3-yl)-1,8,10-triazatricyclo[7.4.0.0$^{2,7}$]trideca-2(7),3,5,8,10,12-hexaene-11-carboxamide;

N-[5-(2-methoxyethoxy)pyridin-3-yl]-1,8,10-triazatricyclo[7.4.0.0$^{2,7}$]trideca-2(7),3,5,8,10,12-hexaene-11-carboxamide;

N-[6-(2-methoxyethoxy)pyridin-3-yl]-1,8,10-triazatricyclo[7.4.0.0$^{2,7}$]trideca-2(7),3,5,8,10,12-hexaene-11-carboxamide;

N-(2-methylpyrimidin-5-yl)-7-thia-2,5-diazatricyclo[6.4.0.0$^{2,6}$]dodeca-1(12),3,5,8,10-pentaene-4-carboxamide;

N-[6-(1H-imidazol-1-yl)pyridin-3-yl]-7-thia-2,5-diazatricyclo[6.4.0.0$^{2,6}$]dodeca-1(12),3,5,8,10-pentaene-4-carboxamide;

N-[2-(dimethylamino)ethyl]-7-thia-2,5-diazatricyclo[6.4.0.0$^{2,6}$]dodeca-1(12),3,5,8,10-pentaene-4-carboxamide;

N-(2-methoxyethyl)-7-thia-2,5-diazatricyclo[6.4.0.0$^{2,6}$]dodeca-1(12),3,5,8,10-pentaene-4-carboxamide;

N-(6-oxo-1,6-dihydropyridin-3-yl)-7-thia-2,5-diazatricyclo[6.4.0.0$^{2,6}$]dodeca-1(12),3,5,8,10-pentaene-4-carboxamide;

N-{[3,3'-bipyridine]-6-yl}-7-thia-2,5-diazatricyclo[6.4.0.0$^{2,6}$]dodeca-1(12),3,5,8,10-pentaene-4-carboxamide;

N-(6-oxo-1,6-dihydropyridazin-3-yl)-7-thia-2,5-diazatricyclo[6.4.0.0$^{2,6}$]dodeca-1(12),3,5,8,10-pentaene-4-carboxamide;

N-(pyridin-3-yl)-1,8,10-triazatricyclo[7.4.0.0$^{2,7}$]trideca-2(7),3,5,8,10,12-hexaene-11-carboxamide;

5-methoxy-N-[6-(methylcarbamoyl)pyridin-3-yl]-1,8,10-triazatricyclo[7.4.0.0$^{2,7}$]trideca-2(7),3,5,8,10,12-hexaene-11-carboxamide;

5-methoxy-N-(5-methoxypyridin-3-yl)-1,8,10-triazatricyclo[7.4.0.0$^{2,7}$]trideca-2(7),3,5,8,10,12-hexaene-11-carboxamide;

5-methoxy-N-(6-oxo-1,6-dihydropyridin-3-yl)-1,8,10-triazatricyclo[7.4.0.0$^{2,7}$]trideca-2(7),3,5,8,10,12-hexaene-11-carboxamide;

5-methoxy-N-(pyridin-3-yl)-1,8,10-triazatricyclo[7.4.0.0$^{2,7}$]trideca-2(7),3,5,8,10,12-hexaene-11-carboxamide;

N-(3-cyanopyridin-4-yl)-5-methoxy-1,8,10-triazatricyclo[7.4.0.0$^{2,7}$]trideca-2(7),3,5,8,10,12-hexaene-11-carboxamide;

5-methoxy-N-(2-methoxypyridin-4-yl)-1,8,10-triazatricyclo[7.4.0.0$^{2,7}$]trideca-2(7),3,5,8,10,12-hexaene-11-carboxamide;

N-(5,6-dimethoxypyridin-3-yl)-5-methoxy-1,8,10-triazatricyclo[7.4.0.0$^{2,7}$]trideca-2(7),3,5,8,10,12-hexaene-11-carboxamide;

11-{1-methyl-1H,4H,5H,6H-pyrrolo[3,4-c]pyrazole-5-carbonyl}-1,8,10-triazatricyclo[7.4.0.0$^{2,7}$]trideca-2(7),3,5,8,10,12-hexaene;

N-[6-(1H-imidazol-1-yl)pyridin-3-yl]-1,8,10-triazatricyclo[7.4.0.0$^{2,7}$]trideca-2(7),3,5,8,10,12-hexaene-11-carboxamide;

5-methoxy-N-(6-oxo-1,6-dihydropyridazin-3-yl)-1,8,10-triazatricyclo[7.4.0.0$^{2,7}$]trideca-2(7),3,5,8,10,12-hexaene-11-carboxamide;

N-(3-cyano-2-methoxypyridin-4-yl)-5-methoxy-1,8,10-triazatricyclo[7.4.0.0$^{2,7}$]trideca-2(7),3,5,8,10,12-hexaene-11-carboxamide;

10-methoxy-N-(5-methoxypyridin-3-yl)-7-thia-2,5-diazatricyclo[6.4.0.0$^{2,6}$]dodeca-1(12),3,5,8,10-pentaene-4-carboxamide;

N-(pyridin-4-yl)-7-thia-2,5-diazatricyclo[6.4.0.0$^{2,6}$]dodeca-1(12),3,5,8,10-pentaene-4-carboxamide;

N-(pyrazin-2-yl)-7-thia-2,5-diazatricyclo[6.4.0.0$^{2,6}$]dodeca-1(12),3,5,8,10-pentaene-4-carboxamide;

3-{7-thia-2,5-diazatricyclo[6.4.0.0$^{2,6}$]dodeca-1(12),3,5,8,10-pentaene-4-amido}pyridin-1-ium-1-olate;

5-methoxy-N-(1-methyl-6-oxo-1,6-dihydropyridin-3-yl)-1,8,10-triazatricyclo[7.4.0.0$^{2,7}$]trideca-2(7),3,5,8,10,12-hexaene-11-carboxamide;

N-(5-methoxypyridin-3-yl)-5-thia-2,7-diazatricyclo[6.4.0.0$^{2,6}$]dodeca-1(12),3,6,8,10-pentaene-4-carboxamide;

N-(1-methyl-6-oxo-1,6-dihydropyridazin-3-yl)-5-thia-2,7-diazatricyclo[6.4.0.0$^{2,6}$]dodeca-1(12),3,6,8,10-pentaene-4-carboxamide;

N-(2-methylpyrimidin-5-yl)-5-thia-2,7-diazatricyclo[6.4.0.0$^{2,6}$]dodeca-1(8),3,6,9,11-pentaene-4-carboxamide;

5-methoxy-N-(1-methyl-2-oxo-1,2-dihydropyrimidin-5-yl)-1,8,10-triazatricyclo[7.4.0.0$^{2,7}$]trideca-2(7),3,5,8,10,12-hexaene-11-carboxamide;

N-{3-[(methylamino)methyl]phenyl}-7-thia-2,5-diazatricyclo[6.4.0.0$^{2,6}$]dodeca-1(8),3,5,9,11-pentaene-4-carboxamide;

5-methoxy-N-[5-(2-methoxyethoxy)pyridin-3-yl]-1,8,10-triazatricyclo[7.4.0.0$^{2,7}$]trideca-2(7),3,5,8,10,12-hexaene-11-carboxamide;

N-(pyridin-3-yl)-7-thia-2,5-diazatricyclo[6.4.0.0$^{2,6}$]dodeca-1(8),3,5,9,11-pentaene-4-carboxamide;

N-(6-methoxypyridin-3-yl)-7-thia-2,5-diazatricyclo[6.4.0.0$^{2,6}$]dodeca-1(8),3,5,9,11-pentaene-4-carboxamide;

N-[(pyridin-3-yl)methyl]-7-thia-2,5-diazatricyclo[6.4.0.0$^{2,6}$]dodeca-1(8),3,5,9,11-pentaene-4-carboxamide;

N-methyl-N-(pyridin-3-yl)-7-thia-2,5-diazatricyclo[6.4.0.0$^{2,6}$]dodeca-1(8),3,5,9,11-pentaene-4-carboxamide;

N-(1-benzofuran-5-yl)-7-thia-2,5-diazatricyclo[6.4.0.0$^{2,6}$]dodeca-1(8),3,5,9,11-pentaene-4-carboxamide;

N-(1-methyl-1H-pyrazol-4-yl)-7-thia-2,5-diazatricyclo[6.4.0.0$^{2,6}$]dodeca-1(8),3,5,9,11-pentaene-4-carboxamide;

N-(6-fluoropyridin-3-yl)-7-thia-2,5-diazatricyclo[6.4.0.0$^{2,6}$]dodeca-1(8),3,5,9,11-pentaene-4-carboxamide;

N-[6-(methylcarbamoyl)pyridin-3-yl]-7-thia-2,5-diazatricyclo[6.4.0.0$^{2,6}$]dodeca-1(8),3,5,9,11-pentaene-4-carboxamide;

4-{1H,2H,3H-pyrrolo[2,3-c]pyridine-1-carbonyl}-7-thia-2,5-diazatricyclo[6.4.0.0$^{2,6}$]dodeca-1(8),3,5,9,11-pentaene;

4-{1-methyl-1H,4H,5H,6H-pyrrolo[3,4-c]pyrazole-5-carbonyl}-7-thia-2,5-diazatricyclo[6.4.0.0$^{2,6}$]dodeca-1(8),3,5,9,11-pentaene;

N-(1-methyl-6-oxo-1,6-dihydropyridazin-3-yl)-7-thia-2,5-diazatricyclo[6.4.0.0$^{2,6}$]dodeca-1(12),3,5,8,10-pentaene-4-carboxamide;

5-methoxy-N-[6-(2-methoxyethoxy)pyridin-3-yl]-1,8,10-triazatricyclo[7.4.0.0$^{2,7}$]trideca-2(7),3,5,8,10,12-hexaene-11-carboxamide;

N-(2,6-dimethoxypyridin-3-yl)-5-methoxy-1,8,10-triazatricyclo[7.4.0.0$^{2,7}$]trideca-2(7),3,5,8,10,12-hexaene-11-carboxamide;

N-(6-fluoro-5-methoxypyridin-3-yl)-5-methoxy-1,8,10-triazatricyclo[7.4.0.0$^{2,7}$]trideca-2(7),3,5,8,10,12-hexaene-11-carboxamide;

N-[6-(2-fluoroethoxy)pyridin-3-yl]-1,8,10-triazatricyclo[7.4.0.0$^{2,7}$]trideca-2(7),3,5,8,10,12-hexaene-11-carboxamide;

N-[5-(2-fluoroethoxy)pyridin-3-yl]-5-methoxy-1,8,10-triazatricyclo[7.4.0.0$^{2,7}$]trideca-2(7),3,5,8,10,12-hexaene-11-carboxamide;

N-(2,6-dimethoxypyridin-3-yl)-1,8,10-triazatricyclo[7.4.0.0$^{2,7}$]trideca-2(7),3,5,8,10,12-hexaene-11-carboxamide;

N-(6-fluoro-5-methoxypyridin-3-yl)-1,8,10-triazatricyclo[7.4.0.0$^{2,7}$]trideca-2(7),3,5,8,10,12-hexaene-11-carboxamide;

N-[6-(2-fluoroethoxy)pyridin-3-yl]-5-methoxy-1,8,10-triazatricyclo[7.4.0.0$^{2,7}$]trideca-2(7),3,5,8,10,12-hexaene-11-carboxamide;

N-[5-(2-fluoroethoxy)pyridin-3-yl]-1,8,10-triazatricyclo[7.4.0.0$^{2,7}$]trideca-2(7),3,5,8,10,12-hexaene-11-carboxamide;

N-[1-(2-fluoroethyl)-6-oxo-1,6-dihydropyridazin-3-yl]-1,8,10-triazatricyclo[7.4.0.0$^{2,7}$]trideca-2(7),3,5,8,10,12-hexaene-11-carboxamide;

N-(2-methoxypyrimidin-5-yl)-7-thia-2,5-diazatricyclo[6.4.0.0$^{2,6}$]dodeca-1(8),3,5,9,11-pentaene-4-carboxamide; and 10-methoxy-N-(2-methoxypyrimidin-5-yl)-7-thia-2,5-diazatricyclo[6.4.0.0$^{2,6}$]dodeca-1(8),3,5,9,11-pentaene-4-carboxamide;

or a pharmaceutically acceptable salt thereof, wherein the compound, or a pharmaceutically acceptable salt thereof, is labeled with one or more positron-emitting radionuclides.

Also provided herein are compounds of Formula I, or a pharmaceutically acceptable salt thereof, that are not labeled with one or more positron-emitting radionuclides.

The compounds of Formula I, or a pharmaceutically acceptable salt thereof are labeled with one or more positron-emitting radionuclides. Suitable positron-emitting radionuclides that may be incorporated in the compounds of described herein, but are not limited to, $^{11}$C, $^{13}$N, $^{15}$O, $^{18}$F, $^{52}$Fe, $^{62}$Cu, $^{64}$Cu, $^{68}$Ga, $^{74}$As, $^{82}$Rb, $^{89}$Zr, $^{122}$I, and $^{124}$I. In some embodiments, the one or more positron-emitting radionuclides are selected from: $^{11}$C, $^{13}$N, $^{15}$O, $^{18}$F, $^{76}$Br, and $^{124}$I. In some embodiments the one or more positron-emitting radionuclides are selected from $^{11}$C, $^{13}$N, $^{15}$O, and $^{18}$F.

Non-metal radionuclides may be covalently linked to the compounds described herein by a reaction well known from the state of art. When the radionuclide is a metallic positron-emitter, it is understood that labeling may require the use of a chelating agent. Such chelating agents are well known from the state of the art.

A PET imaging agent may be labelled with the positron emitter $^{11}$C or $^{18}$F. Methods for the introduction of $^{11}$C may include, but are not limited to, alkylation with [$^{11}$C]iodomethane or [$^{11}$C]methyl triflate, such as described in the Examples below. Carbon-11 has a half-life of approximately 20 minutes, thus $^{11}$C needs to be generated in an on-site cyclotron, and is generally produced as [$^{11}$C]carbon dioxide. The [$^{11}$C]carbon dioxide is converted to the chemical species appropriate for the radiosynthesis (generally [$^{11}$C]iodomethane or the like), and the synthesis of the radiopharmaceutical is completed and used on-site in a PET imaging study after the appropriate radiochemical purity and specific activity have been determined. Typical methods of introducing $^{18}$F may include but are not limited to displacement of a halide, tosylate, or other leaving group with [$^{18}$F]tetrabutylamonium fluoride or [$^{18}$F]potassium fluoride kryptofix-[2.2.2]. Fluorine-18 has a half life of approximately 110 minutes, thus synthesis of [$^{18}$F]radiopharmaceuticals need not necessarily have to occur at the site of the cyclotron nor proximal to the PET imaging study center. General methods for the introduction of these positron emitters are described in the literature (Miller et al., *Angewandte Chemie International Edition*, 47 (2008), 8998-9033). Accordingly, unlabeled analogs of the compounds described herein can be synthesized as described in the synthetic examples below and labeled with positron-emitting radionuclides according to the examples below and/or methods as known in the art.

Provided are methods of generating diagnostic images in an individual comprising administering an effective amount of an imaging agent described herein to an individual, and generating an image of at least a part of the individual.

In some embodiments, generating an image of at least a part of said individual comprises generating an image to detect the presence or absence of huntingtin protein monomers or aggregates in said individual; and detecting the presence or absence of a pathologic process.

In some embodiments, generating an image of at least a part of said individual comprises generating an image to detect the presence or absence of mutant huntingtin protein (mHTT protein) or aggregates thereof in said individual; and detecting the presence or absence of a pathologic process.

Also provided are methods of generating diagnostic images in a biological sample comprising the contacting the biological sample with an effective amount of an imaging agent described herein and generating an image of the positron-emitter labeled compound associated with the biological sample. In this method both the contacting and the generating may be conducted in vitro, alternatively the contacting is in vivo and the generating in vitro.

Also provided are diagnostic methods of using the imaging agents to monitor disease progression in a patient by quantifying the change in levels of the target aggregates in the patient.

Also provided are methods for detecting the presence or absence of a neurodegenerative pathologic process associated with huntingtin protein (HTT protein) in an individual comprising: administering an effective amount of a positron-emitter labeled compound described herein; generating an image to detect the presence or absence of HTT protein aggregates in the individual; and detecting the presence or absence of the pathologic process.

Also provided are methods for detecting the presence or absence of a neurodegenerative pathologic process associated with mutant huntingtin protein (mHTT protein) in an individual comprising: administering an effective amount of a positron-emitter labeled compound described herein; generating an image to detect the presence or absence of mHTT protein or aggregates thereof in the individual; and detecting the presence or absence of the pathologic process.

In some embodiments, the HTT protein monomers or aggregates are present in the brain, liver, heart, or muscle of said individual. In some embodiments, the HTT protein monomers or aggregates are present in the brain of said individual. In some embodiments, the HTT protein monomers or aggregates are present in the basal ganglia, cortex, hippocampus, or brain stem of the brain of the individual.

In some embodiments, the mHTT protein or aggregates thereof are present in the brain, liver, heart, or muscle of said individual. In some embodiments, the mHTT protein or aggregates thereof are present in the brain of said individual. In some embodiments, the mHTT protein or aggregates thereof are present in the basal ganglia, cortex, hippocampus, or brain stem of the brain of the individual.

In some embodiments, the pathologic process is a neurodegenerative disease. In some embodiments, the neurodegenerative disease is chosen from Alzheimer's disease, amyotrphic lateral sclerosis, Huntington's disease, Parkinson's disease, Prion disease, or spinocerebellar ataxias.

In some embodiments, the pathologic process is Huntington's disease (HD).

In some embodiments, the effective amount of the imaging agent comprises from about 0.1 to about 20 mCi. In some embodiments, the effective amount of the imaging agent comprises from about 10 mCi.

In some embodiments, generating an image comprises positron emission tomography (PET) imaging, PET with concurrent computed tomography imaging (PET/CT), PET with concurrent magnetic resonance imaging (PET/MRI), or a combination thereof. In some embodiments, generating an image comprises PET imaging.

Also provided are methods for detecting the presence or absence of a neurodegenerative pathologic process associated with β-amyloid protein in an individual comprising: administering an effective amount of a positron-emitter labeled compound described herein; generating an image to detect the presence or absence of β-amyloid protein aggregates in the individual; and detecting the presence or absence of the pathologic process. In some embodiments, the β-amyloid protein monomers or aggregates are present in the brain, liver, heart, or muscle of said individual. In some embodiments, the β-amyloid protein aggregates are present in the basal ganglia, cortex, hippocampus, or brain stem of the brain of the individual. In some embodiments, the pathologic process is Alzheimer's Disease (AD). In some embodiments, the effective amount of the imaging agent comprises from about 0.1 to about 20 mCi. In some embodiments, the effective amount of the imaging agent comprises from about 10 mCi. In some embodiments, generating an image comprises positron emission tomography (PET) imaging, PET with concurrent computed tomography imaging (PET/CT), PET with concurrent magnetic resonance imaging (PET/MRI), or a combination thereof. In some embodiments, generating an image comprises PET imaging.

Provided herein are compounds having suitable HTT protein aggregate or β-amyloid protein aggregate binding kinetics to function as efficient imaging agents for HTT or protein aggregates or β-amyloid protein aggregates. The requirements of the compounds of the invention to function as efficient imaging agents for HTT protein aggregates are: 1) a high affinity for HTT protein aggregates; 2) a low affinity for nearby structures; 3) slow dissociation kinetics from HTT protein aggregates, which may conveniently be expressed as the dissociation rate constant $k_{diss}$ as defined in the following equation, wherein A and B refer to the HTT or mHTT protein aggregate and the imaging agent, and $k_{assn}$ is the association rate constant.

$$d[AB]/dt = k_{assn}[A][B] - k_{diss}[AB]$$

Provided herein are compounds having suitable mHTT protein aggregate or β-amyloid protein aggregate binding kinetics to function as efficient imaging agents for mHTT protein aggregates or β-amyloid protein aggregates. The requirements of the compounds of the invention to function as efficient imaging agents for mHTT protein aggregates are: 1) a high affinity for mHTT protein aggregates; 2) a low affinity for nearby structures; 3) slow dissociation kinetics from mHTT protein aggregates, which may conveniently be expressed as the dissociation rate constant $k_{diss}$ as defined in the following equation, wherein A and B refer to the mHTT protein aggregate and the imaging agent, and $k_{assn}$ is the association rate constant.

$$d[AB]/dt = k_{assn}[A][B] - k_{diss}[AB]$$

The part of the brain most affected by HD, and thus most likely to contain HTT protein abnormalities (i.e. mHTT protein), is a group of nerve cells at the base of the brain known collectively as the basal ganglia. The basal ganglia organize muscle-driven movements of the body, or "motor movement." The major components of the basal ganglia are the caudate and the putamen (together known as the striatum) and the globus pallidus (external and internal regions). The substantia nigra and the subthalamic nucleus are often included as part of the basal ganglia as well.

The term basal ganglia, refers to a group of subcortical nuclei responsible primarily for motor control, as well as other roles such as motor learning, executive functions and behaviors, and emotions. Disruption of the basal ganglia network forms the basis for several movement disorders. Normal function of the basal ganglia requires fine tuning of neuronal excitability within each nucleus to determine the exact degree of movement facilitation or inhibition at any given moment. This is mediated by the complex organization of the striatum, where the excitability of medium spiny neurons is controlled by several pre- and postsynaptic mechanisms as well as interneuron activity, and secured by several recurrent or internal basal ganglia circuits. The motor circuit of the basal ganglia has two entry points, the striatum and the subthalamic nucleus, and an output, the globus pallidus pars interna, which connects to the cortex via the motor thalamus.

Provided are methods for imaging part of the brain of an individual involving administering a positron-emitter labeled compound described herein to the individual, e.g. into the individual's vascular system, from where it passes through the blood-brain barrier, and then generating an image of at least the part of the individual's brain to which the compound has distributed.

Also provided are pharmaceutical compositions comprising an effective amount of a positron-emitter labeled compound described herein, or a salt thereof, together with one or more pharmaceutically-acceptable adjuvants, excipients or diluents.

Also provided are pharmaceutical compositions comprising an effective amount of a positron-emitter labeled compound described herein, or a pharmaceutically acceptable salt thereof, together with one or more pharmaceutically acceptable adjuvants, excipients or diluents.

An imaging agent or pharmaceutical composition thereof may be administered to a patient in need of treatment via any suitable route. Routes of administration may include, for example, parenteral administration (including subcutaneous, intramuscular, intravenous, by means of, for example a drip patch). Further suitable routes of administration include (but are not limited to) oral, rectal, nasal, topical (including buccal and sublingual), infusion, vaginal, intradermal, intraperitoneally, intracranially, intrathecal and epidural administration or administration via oral or nasal inhalation, by means of, for example a nebulizer or inhaler, or by an implant.

An imaging agent or pharmaceutical composition thereof may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, N. C. et al. 7th Edition ISBN 0-683305-72-7, the entire disclosures of which are herein incorporated by reference.

Also provided are uses of positron-emitter labeled compound described herein for the manufacture of an imaging agent for use in a method of diagnosis of an individual.

Provided are methods of generating diagnostic images comprising positron emission tomography (PET). PET involves the administration of a positron-emitting radionuclide tracer to an individual. Once the tracer has had sufficient time to associate with the target of interest, the individual is placed in a scanning device comprising a ring of scintillation detectors. An emitted positron travels through the individual's tissue for a short (isotope-dependent) distance, until it interacts with an electron. The interaction annihilates both the electron and the positron, producing a pair of photons moving in approximately opposite directions. These are detected when they reach a scintillator in the scanning device. Photons that do not arrive in pairs are ignored.

Also provided are methods of generating diagnostic images comprising PET with concurrent computed tomography imaging (PET/CT), or with concurrent magnetic resonance imaging (PET/MRI). Computed tomography uses X-rays to show the structure of the brain, while magnetic resonance imaging uses magnetic fields and radio waves.

Other uses of the disclosed imaging agents and methods will become apparent to those skilled in the art based upon, inter alia, a review of this disclosure.

As will be recognized, the steps of the methods described herein need not be performed any particular number of times or in any particular sequence. Additional objects, advantages and novel features of the disclosure will become apparent to those skilled in the art upon examination of the following examples thereof, which are intended to be illustrative and not intended to be limiting.

EXAMPLES

General Experimental Details

Commercially available reagents and solvents (HPLC grade) were used without further purification. $^1$H NMR spectra were recorded on a Bruker DRX 500 MHz spectrometer, a Bruker AVANCE 500 MHz spectrometer, a Bruker AVANCE 300 MHz spectrometer or a Bruker DPX 250 MHz spectrometer in deuterated solvents. Chemical shifts (δ) are in parts per million. SCX chromatography was performed with Biotage Isolute Flash SCX-2 loading the sample in methanol and eluting with methanol then 5% ammonia in methanol.

Analytical HPLC-MS (METCR1600), was performed on Hewlett Packard HPLC systems using reverse phase Phenomenex Gemini $C_{18}$ columns (2 µm, 2.0×100 mm), gradient 5-100% B (A=2 mM ammonium bicarbonate in water buffered to pH10, B=acetonitrile) over 5.9 minutes injection volume 3 µL, flow=0.5 mL/minute. UV spectra were recorded at 215 nm using a Waters photo diode array detector. Mass spectra were obtained over the range m/z 150 to 850 at a sampling rate of 2 scans per second using a Waters ZQ. Data were integrated and reported using OpenLynx software.

Analytical HPLC-MS (METCR1673), was performed on Shimadzu LCMS-2010EV systems using reverse phase Supelco Ascentis Express (2.7 µm, 2.1×30 mm), gradient 5-100% B (A=water/0.1% formic acid, B=acetonitrile/0.1% formic acid) over 1.6 minutes injection volume 3 µL, flow=1.0 mL/minute. UV spectra were recorded at 215 nm using a SPD-M20A photo diode array detector. Mass spectra were obtained over the range m/z 100 to 1000 at a sampling rate of 2 scans per second using a LCMS2010EV. Data were integrated and reported using Shimadzu LCMS-Solutions and PsiPort software.

Alternatively, (METCR1416) analytical HPLC-MS on Shimadzu LCMS-2010EV systems using reverse phase Water Atlantis dC18 columns (3 µm, 2.1×100 mm), gradient 5-100% B (A=water/0.1% formic acid, B=acetonitrile/0.1% formic acid) over 7 minutes, injection volume 3 µL, flow=0.6 mL/minute. UV spectra were recorded at 215 nm using a SPD-M20A photo diode array detector. Mass spectra were obtained over the range m/z 150 to 850 at a sampling rate of 2 scans per second using a LCMS2010EV. Data were integrated and reported using Shimadzu LCMS-Solutions and PsiPort software.

Alternatively, (MET-uHPLC-AB-101) analytical HPLC-MS were performed on a Waters Acquity UPLC system with Waters PDA and ELS detectors using a Phenomenex Kinetex-XB C-18 column, (1.7 µM, 2.1 mm×100 mm at a column temperature of 40° C., gradient 5-100% B (A=water/0.1% formic acid; B=acetonitrile/0.1% formic acid) over 5.3 minutes, then 100% B for 0.5 minutes, flow=0.6 mL/minute. UV spectra were recorded at 215 nm using a Waters Acquity photo diode array. Mass spectra were obtained over the range m/z 150 to 850 at a sampling rate of 5 scans per second using a Waters SQD. Data were integrated and reported using Waters MassLynx and OpenLynx software.

All example compounds display an LC purity of >95% unless stated otherwise.

Method 1

Scheme for Method 1

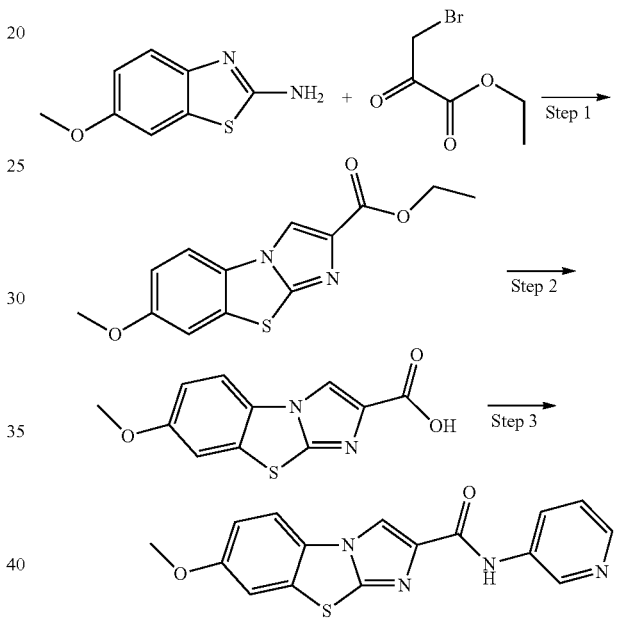

Step 1, Method 1: Ethyl 10-methoxy-7-thia-2,5-diazatricyclo[6.4.0.0$^{2,6}$]dodeca-1(12),3,5,8,10-pentaene-4-carboxylate 6-Methoxy-1,3-benzothiazol-2-amine (5 g, 27.74 mmol) was dissolved in dimethoxyethane (60 mL). Ethyl 3-bromo-2-oxopropanoate (3.5 mL, 27.74 mmol) was added and the resulting mixture heated to reflux for 18 hours. The mixture was cooled to room temperature and stood for 48 hours. The mixture was filtered and the solid washed with tert-butyl methyl ether (2×10 mL) then dried under suction. The solid was suspended in water and the mixture adjusted to pH 9 with ammonium hydroxide solution. The mixture was filtered and the solid washed with tert-butyl methyl ether (100 mL) then dried under suction to give a tan powder (4.8 g). 1.45 g was purified by column chromatography (silica, 12-100% ethyl acetate in heptane) to give the title compound 122 mg (2% yield) as a yellow powder. $^1$H NMR (500 MHz, DMSO) 8.96 (s, 1H), 8.08 (d, J=8.9 Hz, 1H), 7.69 (d, J=2.5 Hz, 1H), 7.15 (dd, J=8.9, 2.5 Hz, 1H), 4.29 (q, J=7.1 Hz, 2H), 3.83 (s, 3H), 1.31 (t, J=7.1 Hz, 3H). Tr(MET-uHPLC-AB-101)=2.8 min, m/z (ES$^+$) (M+H)$^+$ 277.

Step 2, Method 1: 10-Methoxy-7-thia-2,5-diazatricyclo[6.4.0.0$^{2,6}$]dodeca-1(12),3,5,8,10-pentaene-4-carboxylic acid Ethyl 10-methoxy-7-thia-2,5-diazatricyclo[6.4.0.0$^{2,6}$]dodeca-1(12),3,5,8,10-pentaene-4-carboxylate (250 mg, 0.9 mmol) was suspended in dioxane (10 mL), 2 M sodium hydroxide (0.45 mL, 0.91 mmol) was added and the mixture stirred at room temperature for 30 minutes. Additional 2 M sodium hydroxide (0.5 mL) was added and stirring continued overnight. The reaction mixture was acidified with 1 M hydrochloric acid (10 mL) and the precipitate collected by filtration. The precipitate was dissolved in methanol and concentrated in vacuo to give the title compound 190 mg (85% yield) as a beige solid. $^1$H NMR (500 MHz, DMSO) 12.59 (br. s, 1H), 8.88 (s, 1H), 8.06 (d, J=8.9 Hz, 1H), 7.69 (d, J=2.5 Hz, 1H), 7.15 (dd, J=8.9, 2.5 Hz, 1H), 3.83 (s, 3H). Tr(METCR1673)=0.98 min, m/z (ES$^+$) (M+H)$^+$ 249.

Step 3, Method 1: 10-Methoxy-N-(pyridin-3-yl)-7-thia-2,5-diazatricyclo[6.4.0.0$^{2,6}$]dodeca-1(12),3,5,8,10-pentaene-4-carboxamide 10-Methoxy-7-thia-2,5-diazatricyclo[6.4.0.0$^{2,6}$]dodeca-1(12),3,5,8,10-pentaene-4-carboxylic acid (190 mg, 0.77 mmol), pyridin-3-amine (79 mg, 0.84 mmol), 1-[bis(dimethylamino)methylene]-1H-1,2,3-triazolo[4,5-b]pyridinium 3-oxide hexafluorophosphate (320.1 mg, 0.84 mmol) and ethyldiisopropylamine (0.4 mL, 2.3 mmol) were dissolved in N,N-dimethylformamide (5 mL) and stirred at room temperature for 40 hours under nitrogen. The solvents were removed in vacuo and the residue partitioned between water (20 mL) and ethyl acetate (100 mL), the mixture was filtered and the precipitate dried under suction to give the title compound 136 mg (55% yield) as a white solid.

Example 1, Method 1: 10-Methoxy-N-(pyridin-3-yl)-7-thia-2,5-diazatricyclo[6.4.0.0$^{2,6}$]dodeca-1(12),3,5,8,10-pentaene-4-carboxamide $^1$H NMR (500 MHz, DMSO) 10.47 (s, 1H), 9.04 (d, J=2.3 Hz, 1H), 8.98 (s, 1H), 8.34-8.23 (m, 2H), 8.11 (d, J=8.9 Hz, 1H), 7.73 (d, J=2.5 Hz, 1H), 7.47-7.30 (m, 1H), 7.19 (dd, J=8.9, 2.5 Hz, 1H), 3.84 (s, 3H). Tr(MET-uHPLC-AB-101)=1.92 min, m/z (ES$^+$) (M+H)$^+$ 325.

The following examples were prepared using Method 1, or similar methods thereof, described above.

TABLE 1

| Ex. | Structure | Mol. Weight | IUPAC Name | LCMS data |
|---|---|---|---|---|
| 1 | 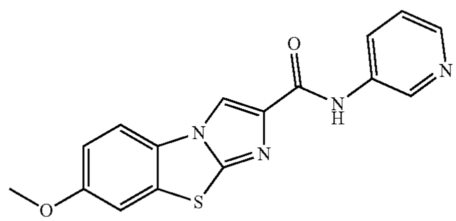 [SMILES: COc1ccc2c(c1)sc1nc(C(=O)Nc3cccnc3)cn12] | 324.36 | 10-methoxy-N-(pyridin-3-yl)-7-thia-2,5-diazatricyclo[6.4.0.0$^{2,6}$]dodeca-1(12),3,5,8,10-pentaene-4-carboxamide | Tr(MET-uHPLC-AB-101) = 1.92 min, m/z (ES$^+$) (M + H)$^+$ 325 |
| 2 | 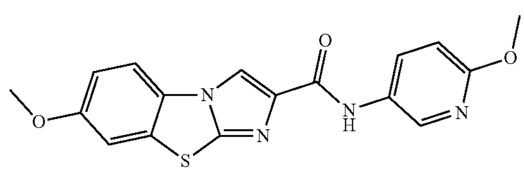 | 354.38 | 10-methoxy-N-(6-methoxypyridin-3-yl)-7-thia-2,5-diazatricyclo[6.4.0.0$^{2,6}$]dodeca-1(12),3,5,8,10-pentaene-4-carboxamide | Tr(MET-uHPLC-AB-101) = 3.08 min, m/z (ES$^+$) (M + H)$^+$ 355 |
| 3 | 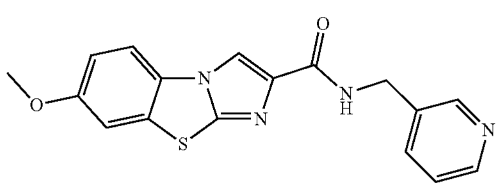 [SMILES: COc1ccc2c(c1)sc1nc(C(=O)NCc3cccnc3)cn12] | 338.38 | 10-methoxy-N-(pyridin-3-ylmethyl)-7-thia-2,5-diazatricyclo[6.4.0.0$^{2,6}$]dodeca-1(12),3,5,8,10-pentaene-4-carboxamide | Tr(METCR1416 Hi res 7 min) = 2.78 min, m/z (ES$^+$) (M + H)$^+$ 339 |
| 4 | 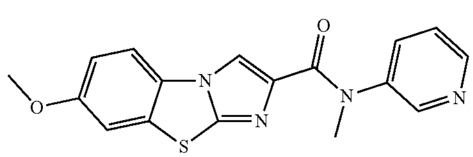 [SMILES: COc1ccc2c(c1)sc1nc(C(=O)N(C)c3cccnc3)cn12] | 338.38 | 10-methoxy-N-methyl-N-(pyridin-3-yl)-7-thia-2,5-diazatricyclo[6.4.0.0$^{2,6}$]dodeca-1(12),3,5,8,10-pentaene-4-carboxamide | Tr(MET-uHPLC-AB-101) = 1.95 min, m/z (ES$^+$) (M + H)$^+$ 339 |
| 5 | 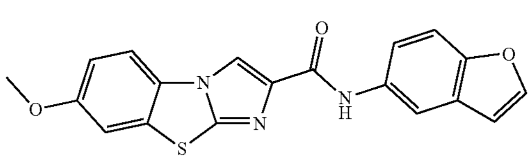 [SMILES: COc1ccc2c(c1)sc1nc(C(=O)Nc3ccc4occc4c3)cn12] | 363.39 | N-(1-benzofuran-5-yl)-10-methoxy-7-thia-2,5-diazatricyclo[6.4.0.0$^{2,6}$]dodeca-1(12),3,5,8,10-pentaene-4-carboxamide | Tr(MET-uHPLC-AB-101) = 3.63 min, m/z (ES$^+$) (M + H)$^+$ 364 |

TABLE 1-continued

| Ex. | Structure | Mol. Weight | IUPAC Name | LCMS data |
|---|---|---|---|---|
| 6 | 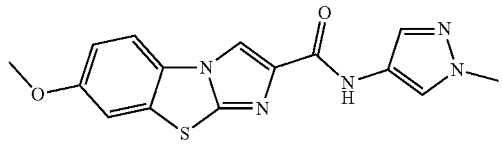 | 327.36 | 10-methoxy-N-(1-methyl-1H-pyrazol-4-yl)-7-thia-2,5-diazatricyclo[6.4.0.0$^{2,6}$]dodeca-1(12),3,5,8,10-pentaene-4-carboxamide | Tr(MET-uHPLC-AB-101) = 2.47 min, m/z (ES$^+$) (M + H)$^+$ 328 |
| 7 | 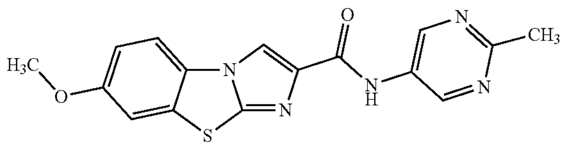 | 339.37 | 10-methoxy-N-(2-methylpyrimidin-5-yl)-7-thia-2,5-diazatricyclo[6.4.0.0$^{2,6}$]dodeca-1(12),3,5,8,10-pentaene-4-carboxamide | Tr(METCR 1600) = 3.95 min, m/z (ES$^+$) (M + H)$^+$ 340 |
| 8 | 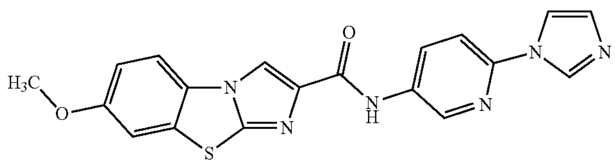 [SMILES: COc1ccc2c(c1)sc1nc(C(=O)Nc3ccc(-n4ccnc4)nc3)cn12] | 390.42 | N-[6-(1H-imidazol-1-yl)pyridin-3-yl]-10-methoxy-7-thia-2,5-diazatricyclo[6.4.0.0$^{2,6}$]dodeca-1(12),3,5,8,10-pentaene-4-carboxamide | Tr(MET-uHPLC-AB-101) = 1.92 min, m/z (ES$^+$) (M + H)$^+$ 391 |
| 9 | 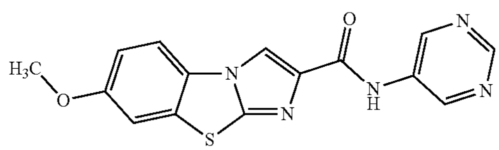 [SMILES: COc1ccc2c(c1)sc1nc(C(=O)Nc3cncnc3)cn12] | 325.35 | 10-methoxy-N-(pyrimidin-5-yl)-7-thia-2,5-diazatricyclo[6.4.0.0$^{2,6}$]dodeca-1(12),3,5,8,10-pentaene-4-carboxamide | Tr(MET-uHPLC-AB-101) = 2.42 min, m/z (ES$^+$) (M + H)$^+$ 326 |
| 10 | 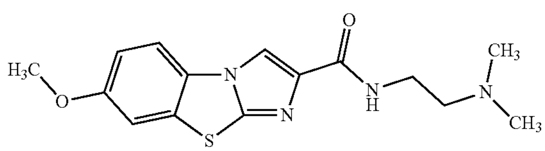 | 318.40 | N-[2-(dimethylamino)ethyl]-10-methoxy-7-thia-2,5-diazatricyclo[6.4.0.0$^{2,6}$]dodeca-1(12),3,5,8,10-pentaene-4-carboxamide | Tr(MET-uHPLC-AB-101) = 1.41 min, m/z (ES$^+$) (M + H)$^+$ 319 |
| 11 | 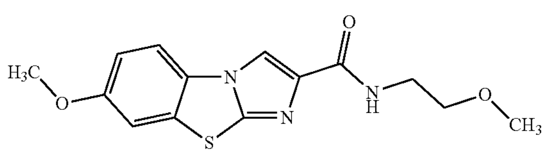 | 305.35 | 10-methoxy-N-(2-methoxyethyl)-7-thia-2,5-diazatricyclo[6.4.0.0$^{2,6}$]dodeca-1(12),3,5,8,10-pentaene-4-carboxamide | Tr(MET-uHPLC-AB-101) = 2.41 min, m/z (ES$^+$) (M + H)$^+$ 306 |
| 12 | 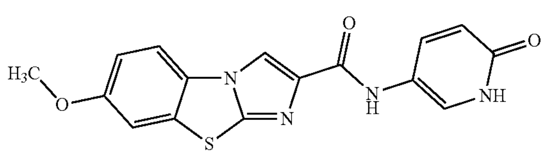 | 340.36 | 10-methoxy-N-(6-oxo-1,6-dihydropyridin-3-yl)-7-thia-2,5-diazatricyclo[6.4.0.0$^{2,6}$]dodeca-1(12),3,5,8,10-pentaene-4-carboxamide | Tr(METCR 1600) = 3.52 min, m/z (ES$^+$) (M + H)$^+$ 341 |
| 13 | 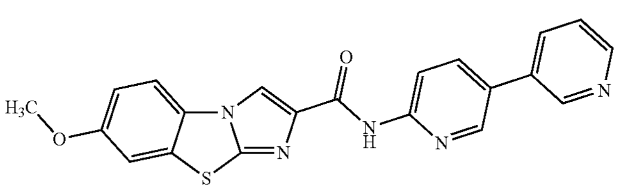 [SMILES: COc1ccc2c(c1)sc1nc(C(=O)Nc3ccc(-c4cccnc4)cn3)cn12] | 401.44 | 10-methoxy-N-[5-(pyridin-3-yl)pyridin-2-yl]-7-thia-2,5-diazatricyclo[6.4.0.0$^{2,6}$]dodeca-1(12),3,5,8,10-pentaene-4-carboxamide | Tr(MET-uHPLC-AB-101) = 2.62 min, m/z (ES$^+$) (M + H)$^+$ 402 |
| 14 | 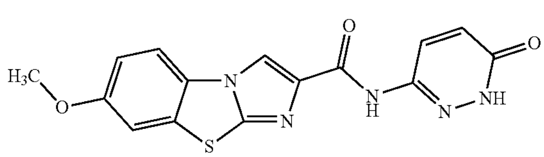 | 341.35 | 10-methoxy-N-(6-oxo-1,6-dihydropyridazin-3-yl)-7-thia-2,5-diazatricyclo[6.4.0.0$^{2,6}$]dodeca-1(12),3,5,8,10-pentaene-4-carboxamide | Tr(MET-uHPLC-AB-101) = 2.21 min, m/z (ES$^+$) (M + H)$^+$ 342 |

TABLE 1-continued

| Ex. | Structure | Mol. Weight | IUPAC Name | LCMS data |
|---|---|---|---|---|
| 15 | 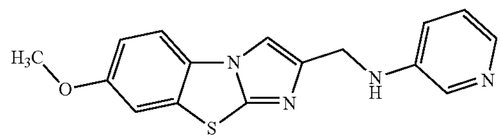 [SMILES: COc1ccc2c(c1)sc1nc(CNc3cccnc3)cn12] | 310.38 | N-({10-methoxy-7-thia-2,5-diazatricyclo[6.4.0.0²,⁶]dodeca-1(12),3,5,8,10-pentaene-4-yl}methyl)pyridin-3-amine | |

Method 2

Scheme for Method 2

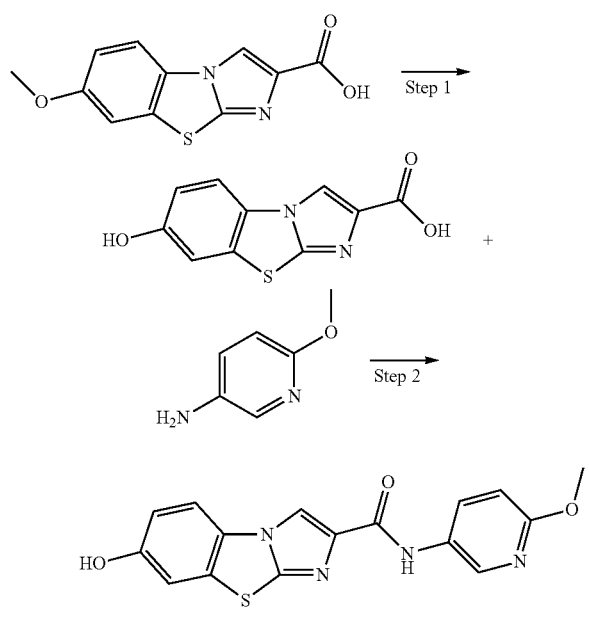

Step 1, Method 2: 10-Hydroxy-7-thia-2,5-diazatricyclo[6.4.0.0$^{2,6}$]dodeca-1(8),3,9,11-tetraene-4-carboxylic acid 10-Methoxy-7-thia-2,5-diazatricyclo[6.4.0.0$^{2,6}$]dodeca-1(8),3,9,11-tetraene-4-carboxylic acid (638 mg, 2.57 mmol, prepared by Method 1) was suspended in dichloromethane (50 mL) and stirred for five minutes. 1 M tribromoborane in dichloromethane (10 mL, 10.28 mmol) was added and the reaction was stirred for 2 hours. The reaction mixture was quenched with water (100 mL) and concentrated in vacuo. Trituration with acetonitrile (5 mL) gave the title compound 821 mg (100% yield, 74% purity) as a red solid. $^1$H NMR (500 MHz, DMSO) 9.97 (s, 1H), 8.84 (s, 1H), 7.95 (d, J=8.8 Hz, 1H), 7.40 (d, J=2.3 Hz, 1H), 6.96 (dd, J=8.8, 2.4 Hz, 1H). Tr(METCR1673)=0.77 min, m/z (ES$^+$) (M+H)$^+$ 235.

Step 2, Method 2: 10-Hydroxy-N-(6-methoxypyridin-3-yl)-7-thia-2,5-diazatricyclo[6.4.0.0$^{2,6}$]dodeca-1(8),3,9,11-tetraene-4-carboxamide 10-Hydroxy-7-thia-2,5-diazatricyclo[6.4.0.0$^{2,6}$]dodeca-1(8),3,9,11-tetraene-4-carboxylic acid (400 mg, 1.71 mmol), 6-methoxypyridin-3-amine (0.2 mL, 1.87 mmol), 1-[bis(dimethylamino)methylene]-1H-1,2,3-triazolo[4,5-b]pyridinium 3-oxide hexafluorophosphate (714 mg, 1.87 mmol) and ethyldiisopropylamine (0.9 mL, 5.12 mmol) were dissolved in N,N-dimethylformamide (15 mL) and stirred at room temperature for 18 hours. The reaction mixture was added to water (100 mL) and brine (100 mL) and extracted with ethyl acetate (3×200 mL). The extracts were combined, washed with brine (100 mL), dried over magnesium sulfate, filtered and concentrated in vacuo. Recrystallisation from 2:1 acetonitrile:water (50 mL) gave the title compound 60 mg (10% yield) as a brown solid.

Example 1, Method 2: 10-Hydroxy-N-(6-methoxypyridin-3-yl)-7-thia-2,5-diazatricyclo[6.4.0.0$^{2,6}$]dodeca-1(8),3,9,11-tetraene-4-carboxamide $^1$H NMR (500 MHz, DMSO) 10.22 (s, 1H), 10.08 (s, 1H), 8.85 (s, 1H), 8.61 (d, J=2.6 Hz, 1H), 8.15 (dd, J=8.9, 2.7 Hz, 1H), 7.97 (d, J=8.8 Hz, 1H), 7.41 (d, J=2.3 Hz, 1H), 6.97 (dd, J=8.7, 2.4 Hz, 1H), 6.82 (d, J=8.9 Hz, 1H), 3.83 (s, 3H). Tr(MET-uHPLC-AB-101)=2.48 min, m/z (ES$^+$) (M+H)$^+$ 341, 94%.

The following examples were prepared using Method 2 described above:

TABLE 2

| Ex. | Structure | Mol. Weight | IUPAC Name | LCMS data |
|---|---|---|---|---|
| 1 | 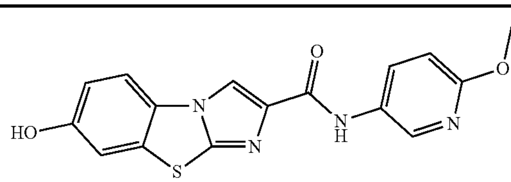 | 340.36 | 10-hydroxy-N-(6-methoxypyridin-3-yl)-7-thia-2,5-diazatricyclo[6.4.0.0$^{2,6}$]dodeca-1(12),3,5,8,10-pentaene-4-carboxamide | Tr(MET-uHPLC-AB-101) = 2.48 min, m/z (ES$^+$) (M + H)$^+$ 341 |

TABLE 2-continued

| Ex. | Structure | Mol. Weight | IUPAC Name | LCMS data |
|---|---|---|---|---|
| 2 | 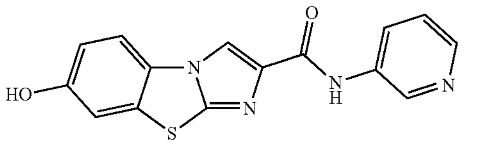 [SMILES: O=C(Nc1cccnc1)c1cn2c(n1)sc1cc(O)ccc12] | 310.33 | 10-methoxy-N-(pyridin-3-yl)-7-thia-2,5-diazatricyclo[6.4.0.0$^{2,6}$]dodeca-1(12),3,5,8,10-pentaene-4-carboxamide | Tr(MET-uHPLC-AB-101) = 1.43 min, m/z (ES$^+$) (M + H)$^+$ 311 |

Method 3

Scheme for Method 3

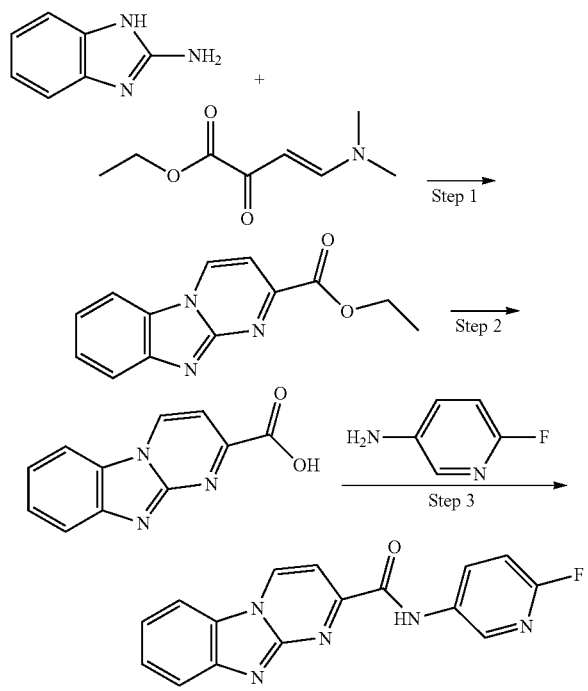

Step 1, Method 3: Ethyl 1,8,10-triazatricyclo[7.4.0.0$^{2,7}$]trideca-2(7),3,5,8,10,12-hexaene-11-carboxylate 1H-Benzimidazol-2-amine (2 g, 15.02 mmol) and ethyl (3E)-4-(dimethylamino)-2-oxobut-3-enoate (70%, 4 g, 16.36 mmol, described in US2011001121) were suspended in acetic acid (50 mL) and the reaction heated at 120° C. for 16 hours. The reaction mixture was cooled to room temperature and the solvents removed in vacuo. The residue was basified with saturated sodium bicarbonate solution (50 mL). The mixture was partitioned with ethyl acetate (150 mL) and the biphasic mixture filtered. The phases were separated and the aqueous further extracted with ethyl acetate (2×100 mL). The combined organics were dried over anhydrous magnesium sulfate, filtered and concentrated in vacuo. Purification by FCC (silica, 40-100% ethyl acetate in heptane) gave the title compound 360 mg (10% yield) as a yellow powder. $^1$H NMR (500 MHz, DMSO) 9.73 (d, J=7.0 Hz, 1H), 8.42 (d, J=8.2 Hz, 1H), 7.96 (d, J=8.3 Hz, 1H), 7.74-7.59 (m, 2H), 7.59-7.38 (m, 1H), 4.45 (q, J=7.1 Hz, 2H), 1.40 (t, J=7.1 Hz, 3H). Tr(METCR1673)=0.96 min, m/z (ES$^+$) (M+H)$^+$ 242.

Step 2, Method 3: 1,8,10-Triazatricyclo[7.4.0.0$^{2,7}$]trideca-2(7),3,5,8,10,12-hexaene-11-carboxylic acid Ethyl 1,8,10-triazatricyclo[7.4.0.0$^{2,7}$]trideca-2(7),3,5,8,10,12-hexaene-11-carboxylate (360 mg, 1.45 mmol) was suspended in tetrahydrofuran (10 mL), 2 M sodium hydroxide (1.5 mL) added and the reaction was stirred at room temperature for 2 hours. The tetrahydrofuran was removed in vacuo and the residue acidified with 1 M hydrogen chloride (2 mL), adjusting the pH to 4-5. The solvents were removed in vacuo and the product azeotroped with toluene (2×20 mL) to give the title compound 440 mg (100% yield) as a yellow powder. $^1$H NMR (500 MHz, DMSO) 9.56 (d, J=6.9 Hz, 1H), 8.34 (d, J=8.2 Hz, 1H), 7.88 (d, J=8.2 Hz, 1H), 7.59-7.52 (m, 2H), 7.44 (appt t, J=7.7 Hz, 1H). Tr(METCR1673)=0.27 min, m/z (ES$^+$) (M+H)$^+$ 214, 49%.

Step 3, Method 3: N-(6-Methoxypyridin-3-yl)-1,8,10-triazatricyclo[7.4.0.0$^{2,7}$]trideca-2(7),3,5,8,10,12-hexaene-11-carboxamide 1,8,10-Triazatricyclo[7.4.0.0$^{2,7}$]trideca-2(7),3,5,8,10,12-hexaene-11-carboxylic acid (100 mg, 0.42 mmol), 6-methoxypyridin-3-amine (63 mg, 0.51 mmol), 1-[bis(dimethylamino)methylene]-1H-1,2,3-triazolo[4,5-b]pyridinium 3-oxide hexafluorophosphate (192.62 mg, 0.51 mmol) and ethyldiisopropylamine (0.22 mL, 1.27 mmol) were dissolved in anhydrous N,N-dimethylformamide (5 mL) and the reaction stirred at room temperature for 16 hours. The reaction mixture was evaporated and the residue partitioned between ethyl acetate (20 mL) and water (20 mL). The mixture was filtered through glass fibre filter paper and the precipitate dried in vacuo to give the title compound 27 mg (20% yield) as a green solid.

Example 1, Method 3: N-(6-Methoxypyridin-3-yl)-1,8,10-triazatricyclo[7.4.0.0$^{2,7}$]trideca-2(7),3,5,8,10,12-hexaene-11-carboxamide $^1$H NMR (500 MHz, DMSO) 11.06 (s, 1H), 9.77 (d, J=7.0 Hz, 1H), 8.71 (d, J=2.6 Hz, 1H), 8.43 (d, J=8.2 Hz, 1H), 8.22 (dd, J=8.9, 2.7 Hz, 1H), 7.96 (d, J=8.2 Hz, 1H), 7.77 (d, J=7.0 Hz, 1H), 7.64 (appt t, J=7.7 Hz, 1H), 7.53 (appt t, J=7.7 Hz, 1H), 6.89 (d, J=8.9 Hz, 1H), 3.87 (s, 3H). Tr(MET-uHPLC-AB-101)=2.19 min, m/z (ES$^+$) (M+H)$^+$ 320.

The following examples were prepared using Method 3 described above:

TABLE 3

| Ex. | Structure | Mol. Weight | IUPAC Name | LCMS data |
|---|---|---|---|---|
| 1 | 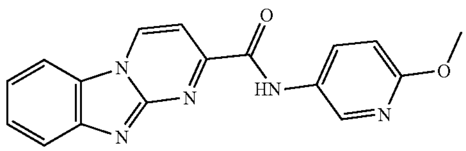 [SMILES: COc1ccc(NC(=O)c2ccn3c(n2)nc2ccccc23)cn1] | 319.32 | N-(6-methoxypyridin-3-yl)-1,8,10-triazatricyclo[7.4.0.0$^{2,7}$]trideca-2(7),3,5,8,10,12-hexaene-11-carboxamide | Tr(MET-uHPLC-AB 101) = 2.19 min, m/z (ES$^+$) (M + H)$^+$ 320 |
| 2 | 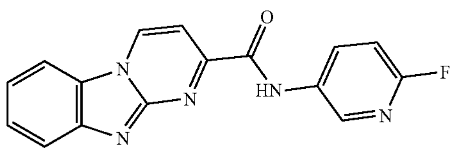 [SMILES: O=C(Nc1ccc(F)nc1)c1ccn2c(n1)nc1ccccc12] | 307.28 | N-(6-fluoropyridin-3-yl)-1,8,10-triazatricyclo[7.4.0.0$^{2,7}$]trideca-2(7),3,5,8,10,12-hexaene-11-carboxamide | Tr(MET-uHPLC-AB-101) = 2.17 min, m/z (ES$^+$) (M + H)$^+$ 308 |
| 3 | 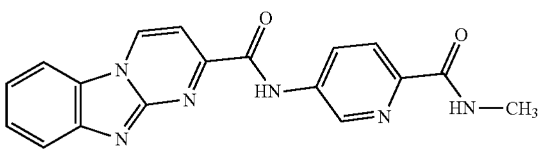 [SMILES: CNC(=O)c1ccc(NC(=O)c2ccn3c(n2)nc2ccccc23)cn1] | 346.35 | N-[6-(methylcarbamoyl)pyridin-3-yl]-1,8,10-triazatricyclo[7.4.0.0$^{2,7}$]trideca-2(7),3,5,8,10,12-hexaene-11-carboxamide | Tr(MET-uHPLC-AB-101) = 1.95 min, m/z (ES$^+$) (M + H)$^+$ 347 |
| 4 | 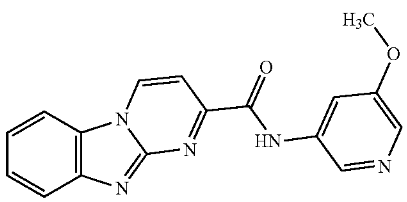 [SMILES: COc1cncc(NC(=O)c2ccn3c(n2)nc2ccccc23)c1] | 319.32 | N-(5-methoxypyridin-3-yl)-1,8,10-triazatricyclo[7.4.0.0$^{2,7}$]trideca-2(7),3,5,8,10,12-hexaene-11-carboxamide | Tr(MET-uHPLC-AB-101) = 1.76 min, m/z (ES$^+$) (M + H)$^+$ 320 |
| 5 | 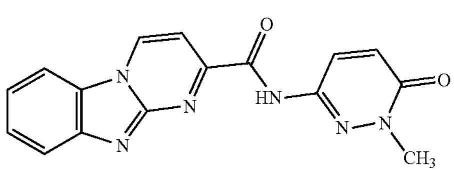 [SMILES: Cn1nc(NC(=O)c2ccn3c(n2)nc2ccccc23)ccc1=O] | 320.31 | N-(1-methyl-6-oxo-1,6-dihydropyridazin-3-yl)-1,8,10-triazatricyclo[7.4.0.0$^{2,7}$]trideca-2(7),3,5,8,10,12-hexaene-11-carboxamide | Tr(MET-uHPLC-AB-101) = 1.65 min, m/z (ES$^+$) (M + H)$^+$ 321 |
| 6 | 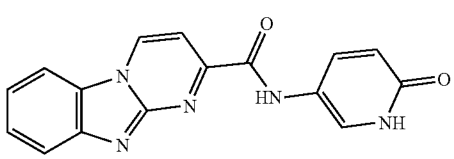 [SMILES: O=C(Nc1ccc(=O)[nH]c1)c1ccn2c(n1)nc1ccccc12] | 305.30 | N-(6-oxo-1,6-dihydropyridin-3-yl)-1,8,10-triazatricyclo[7.4.0.0$^{2,7}$]trideca-2(7),3,5,8,10,12-hexaene-11-carboxamide | Tr(MET-uHPLC-AB-101) = 1.39 min, m/z (ES$^+$) (M + H)$^+$ 306 |
| 7 | 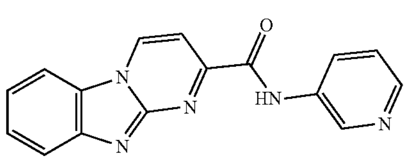 [SMILES: O=C(Nc1cccnc1)c1ccn2c(n1)nc1ccccc12] | 289.30 | N-(pyridin-3-yl)-1,8,10-triazatricyclo[7.4.0.0$^{2,7}$]trideca-2(7),3,5,8,10,12-hexaene-11-carboxamide | Tr(MET-uHPLC-AB-101) = 1.36 min, m/z (ES$^+$) (M + H)$^+$ 290 |
| 8 | 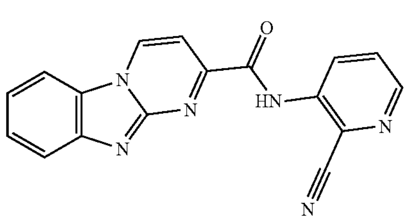 [SMILES: N#Cc1ncccc1NC(=O)c1ccn2c(n1)nc1ccccc12] | 314.31 | N-(3-cyanopyridin-4-yl)-1,8,10-triazatricyclo[7.4.0.0$^{2,7}$]trideca-2(7),3,5,8,10,12-hexaene-11-carboxamide | Tr(MET-uHPLC-AB-101) = 2.19 min, m/z (ES$^+$) (M + H)$^+$ 315 |

TABLE 3-continued

| Ex. | Structure | Mol. Weight | IUPAC Name | LCMS data |
|---|---|---|---|---|
| 9 | 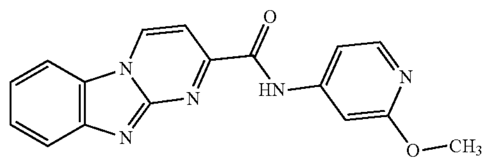 [SMILES: COc1cc(NC(=O)c2ccn3c(n2)nc2ccccc23)ccn1] | 319.32 | N-(2-methoxypyridin-4-yl)-1,8,10-triazatricyclo[7.4.0.0²,⁷]trideca-2(7),3,5,8,10,12-hexaene-11-carboxamide | Tr(MET-uHPLC-AB-101) = 2.08 min, m/z (ES⁺) (M + H)⁺ 320 |
| 10 | 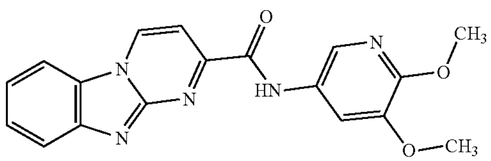 [SMILES: COc1cc(NC(=O)c2ccn3c(n2)nc2ccccc23)cnc1OC] | 349.35 | N-(5,6-dimethoxypyridin-3-yl)-1,8,10-triazatricyclo[7.4.0.0²,⁷]trideca-2(7),3,5,8,10,12-hexaene-11-carboxamide | Tr(MET-uHPLC-AB-101) = 2.2 min, m/z (ES⁺) (M + H)⁺ 350 |
| 11 | 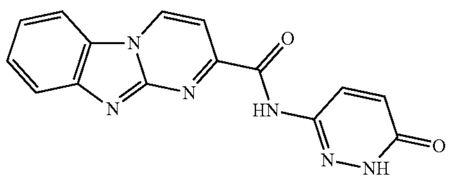 [SMILES: O=C(Nc1ccc(=O)[nH]n1)c1ccn2c(n1)nc1ccccc12] | 306.29 | N-(6-oxo-1,6-dihydropyridin-3-yl)-1,8,10-triazatricyclo[7.4.0.0²,⁷]trideca-2(7),3,5,8,10,12-hexaene-11-carboxamide | Tr(MET-uHPLC-AB-101) = 1.48 min, m/z (ES⁺) (M + H)⁺ 307 |
| 12 | 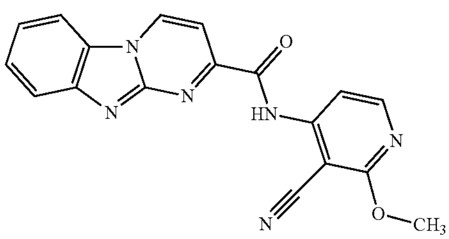 [SMILES: COc1nccc(NC(=O)c2ccn3c(n2)nc2ccccc23)c1C#N] | 344.33 | N-(3-cyano-2-methoxypyridin-4-yl)-1,8,10-triazatricyclo[7.4.0.0²,⁷]trideca-2(7),3,5,8,10,12-hexaene-11-carboxamide | Tr(METCR1603) = 3.76 min, m/z (ES⁺) (M + H)⁺ 345 |

Method 4

Scheme for Method 4

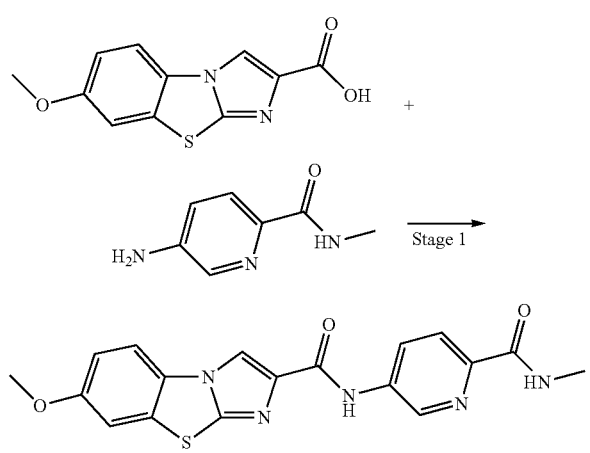

Step 1, Method 4: 10-Methoxy-N-[6-(methylcarbamoyl)pyridin-3-yl]-7-thia-2,5-diazatricyclo[6.4.0.0²,⁶]dodeca-1(12),3,5,8,10-pentaene-4-carboxamide 10-Methoxy-7-thia-2,5-diazatricyclo[6.4.0.0²,⁶]dodeca-1(12),3,5,8,10-pentaene-4-carboxylic acid (95%, 100 mg, 0.38 mmol, described in Method 1) and 5-amino-N-methylpyridine-2-carboxamide (58 mg, 0.38 mmol, as prepared described in PCT Int. Appl., 2008056150) in pyridine (2 mL) were stirred at room temperature for 20 minutes. 1-Ethyl-3-(3-dimethylaminopropyl)carbodiimide hydrochloride (88 mg, 0.46 mmol) was added and the reaction was stirred at room temperature overnight under nitrogen. 5-Amino-N-methylpyridine-2-carboxamide (27 mg, 0.19 mmol) was added and the mixture stirred at room temperature for 20 minutes. 1-Ethyl-3-(3-dimethylaminopropyl)carbodiimide hydrochloride (44 mg, 0.23 mmol) was added and the mixture stirred at room temperature for 2 days. The mixture was heated to 60° C. for 4 hours. The mixture was diluted with pyridine (2 mL) filtered, washed with water (2 mL), methanol (2 mL) and heptane (2 mL). Recrystallization from DMSO (1.5 mL and then 2.5 mL) gave the title compound 30 mg (20% yield) as a white powder.

Example 1, Method 4: 10-Methoxy-N-[6-(methylcarbamoyl)pyridin-3-yl]-7-thia-2,5-diazatricyclo[6.4.0.0$^{2,6}$]dodeca-1(12),3,5,8,10-pentaene-4-carboxamide $^1$H NMR (500 MHz, DMSO) 10.69 (s, 1H), 9.11 (d, J=2.4 Hz, 1H), 9.00 (s, 1H), 8.65 (q, J=4.6 Hz, 1H), 8.49 (dd, J=8.6, 2.5 Hz, 1H), 8.12 (d, J=8.9 Hz, 1H), 8.01 (d, J=8.5 Hz, 1H), 7.72 (d, J=2.5 Hz, 1H), 7.19 (dd, J=8.9, 2.5 Hz, 1H), 3.85 (s, 3H), 2.81 (d, J=4.8 Hz, 3H). Tr(MET-uHPLC-AB-101)=2.77 min, m/z (ES$^+$) (M+H)$^+$ 382.

The following examples were prepared using Method 4 described above:

TABLE 4

| Ex. | Structure | Mol. Weight | IUPAC Name | LCMS data |
|---|---|---|---|---|
| 1 | 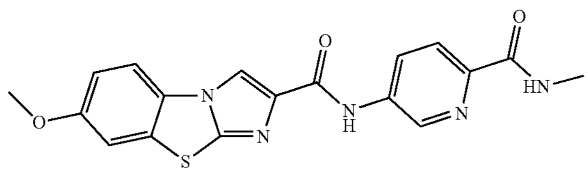 | 381.41 | 10-methoxy-N-[6-(methylcarbamoyl)pyridin-3-yl]-7-thia-2,5-diazatricyclo[6.4.0.0$^{2,6}$]dodeca-1(12),3,5,8,10-pentaene-4-carboxamide | Tr(MET-uHPLC-AB-101) = 2.77 min, m/z (ES$^+$) (M + H)$^+$ 382 |
| 2 | 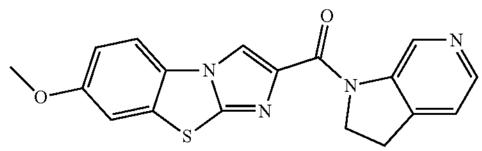 [SMILES: COc1ccc2c(c1)sc1nc(C(=O)N3CCc4ccncc43)cn12] | 350.39 | 10-methoxy-4-{1H,2H,3H-pyrrolo[2,3-c]pyridine-1-carbonyl}-7-thia-2,5-diazatricyclo[6.4.0.0$^{2,6}$]dodeca-1(12),3,5,8,10-pentaene | Tr(MET-uHPLC-AB-101) = 1.86 min, m/z (ES$^+$) (M + H)$^+$ 351 |
| 3 | 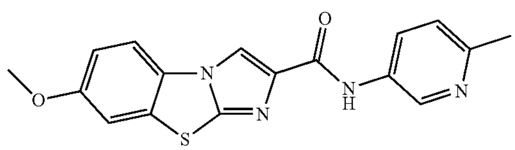 | 338.38 | 10-methoxy-N-(6-methylpyridin-3-yl)-7-thia-2,5-diazatricyclo[6.4.0.0$^{2,6}$]dodeca-1(12),3,5,8,10-pentaene-4-carboxamide | Tr(MET-uHPLC-AB-101) = 1.83 min, m/z (ES$^+$) (M + H)$^+$ 339 |
| 4 | 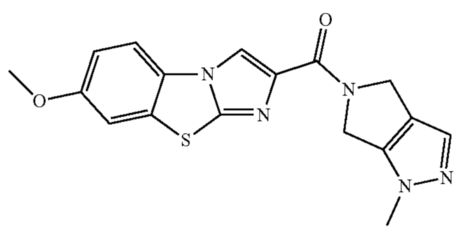 [SMILES: COc1ccc2c(c1)sc1nc(C(=O)N3Cc4cnn(C)c4C3)cn12] | 353.40 | 10-methoxy-4-{1-methyl-1H,4H,5H,6H-pyrrolo[3,4-c]pyrazole-5-carbonyl}-7-thia-2,5-diazatricyclo[6.4.0.0$^{2,6}$]dodeca-1(12),3,5,8,10-pentaene | Tr(METCR1600) = 3.64 min, m/z (ES$^+$) (M + H)$^+$ 354 |
| 5 | 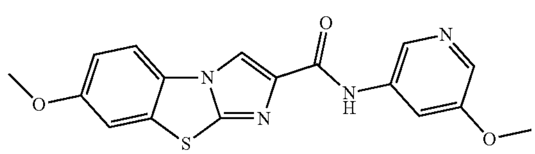 | 354.38 | 10-methoxy-N-(5-methoxypyridin-3-yl)-7-thia-2,5-diazatricyclo[6.4.0.0$^{2,6}$]dodeca-1(12),3,5,8,10-pentaene-4-carboxamide | Tr(MET-uHPLC-AB-101) = 2.43 min, m/z (ES$^+$) (M + H)$^+$ 355 |
| 6 | 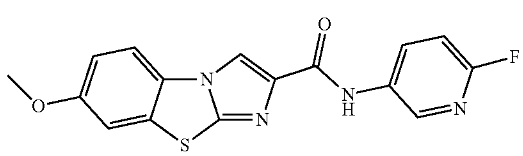 [SMILES: COc1ccc2c(c1)sc1nc(C(=O)Nc3ccc(F)nc3)cn12] | 342.35 | N-(6-fluoropyridin-3-yl)-10-methoxy-7-thia-2,5-diazatricyclo[6.4.0.0$^{2,6}$]dodeca-1(12),3,5,8,10-pentaene-4-carboxamide | Tr(MET-uHPLC-AB-101) = 3.07 min, m/z (ES$^+$) (M + H)$^+$ 343 |
| 7 | 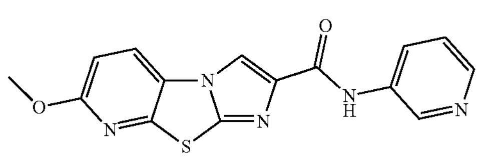 [SMILES: COc1ccc2c(n1)sc1nc(C(=O)Nc3cccnc3)cn12] | 325.35 | 10-methoxy-N-(pyridin-3-yl)-7-thia-2,5,9-triazatricyclo[6.4.0.0$^{2,6}$]dodeca-1(12),3,5,8,10-pentaene-4-carboxamide | Tr(MET-uHPLC-AB-101) = 1.85 min, m/z (ES$^+$) (M + H)$^+$ 326 |

TABLE 4-continued

| Ex. | Structure | Mol. Weight | IUPAC Name | LCMS data |
|---|---|---|---|---|
| 8 | 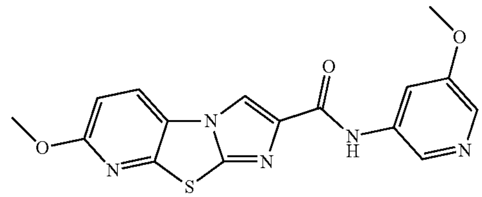 [SMILES: COc1cncc(NC(=O)c2cn3c(n2)sc2nc(OC)ccc23)c1] | 355.37 | 10-methoxy-N-(5-methoxypyridin-3-yl)-7-thia-2,5,9-triazatricyclo[6.4.0.0$^{2,6}$]dodeca-1(12),3,5,8,10-pentaene-4-carboxamide | Tr(MET-uHPLC-AB-101) = 2.34 min, m/z (ES$^+$) (M + H)$^+$ 356 |
| 9 | 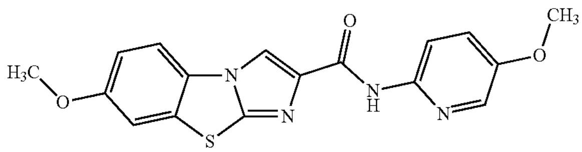 | 354.38 | 10-methoxy-N-(5-methoxypyridin-2-yl)-7-thia-2,5-diazatricyclo[6.4.0.0$^{2,6}$]dodeca-1(12),3,5,8,10-pentaene-4-carboxamide | Tr(METCR1600) = 4.72 min, m/z (ES$^+$) (M + H)$^+$ 355 |
| 10 | 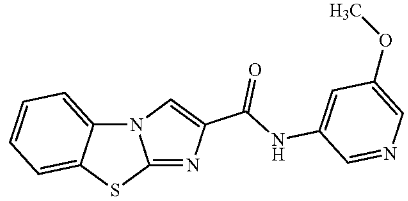 [SMILES: COc1cncc(NC(=O)c2cn3c(n2)sc2ccccc23)c1] | 324.36 | N-(5-methoxypyridin-3-yl)-7-thia-2,5-diazatricyclo[6.4.0.0$^{2,6}$]dodeca-1(12),3,5,8,10-pentaene-4-carboxamide | Tr(MET-uHPLC-AB-101) = 2.26 min, m/z (ES$^+$) (M + H)$^+$ 325 |
| 11 | 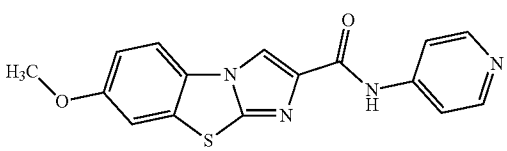 [SMILES: COc1ccc2c(c1)sc1nc(C(=O)Nc3ccncc3)cn12] | 324.36 | 10-methoxy-N-(pyridin-4-yl)-7-thia-2,5-diazatricyclo[6.4.0.0$^{2,6}$]dodeca-1(12),3,5,8,10-pentaene-4-carboxamide | Tr(MET-uHPLC-AB-101) = 1.75 min, m/z (ES$^+$) (M + H)$^+$ 325 |
| 12 | 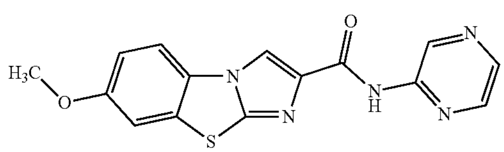 [SMILES: COc1ccc2c(c1)sc1nc(C(=O)Nc3cnccn3)cn12] | 325.35 | 10-methoxy-N-(pyrazin-2-yl)-7-thia-2,5-diazatricyclo[6.4.0.0$^{2,6}$](dodeca-1(12),3,5,8,10-pentaene-4-carboxamide | Tr(MET-uHPLC-AB-101) = 2.87 min, m/z (ES$^+$) (M + H)$^+$ 326 |

Method 5

Scheme for Method 5

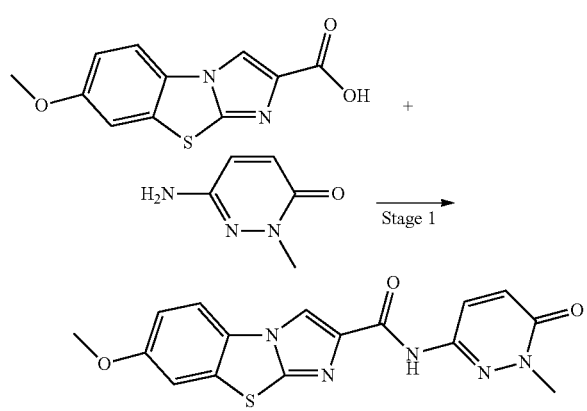

Step 1, Method 5: 10-Methoxy-N-(1-methyl-6-oxo-1,6-dihydropyridazin-3-yl)-7-thia-2,5-diazatricyclo[6.4.0.0$^{2,6}$]dodeca-1(12),3,5,8,10-pentaene-4-carboxamide 10-Methoxy-7-thia-2,5-diazatricyclo[6.4.0.0$^{2,6}$]dodeca-1(12),3,5,8,10-pentaene-4-carboxylic acid (95%, 60 mg, 0.23 mmol, described in Method 1) and 6-amino-2-methyl-2,3-dihydropyridazin-3-one (60%, 48 mg, 0.23 mmol, described in PCT Int. Appl., WO 2011/015629) in pyridine (2 mL) were stirred at room temperature for 20 minutes. 1-Ethyl-3-(3-dimethylaminopropyl)carbodiimide hydrochloride (97 mg, 0.51 mmol) was added and the reaction stirred at room temperature under nitrogen overnight. 1-Ethyl-3-(3-dimethylaminopropyl)carbodiimide hydrochloride (97 mg, 0.51 mmol) was added and the reaction stirred at room temperature under nitrogen for 2 days. The mixture was diluted with pyridine (2 mL) filtered, washed with methanol (2 mL), water (2 mL), methanol (2 mL) and heptane (2 mL). Purification by recrystallisation from 1:1 methanol:dimethylsulfoxide (5 mL) gave the title compound 24 mg (29% yield) as an off white powder.

Example 1: Method 5: 10-Methoxy-N-(1-methyl-6-oxo-1,6-dihydropyridazin-3-yl)-7-thia-2,5-diazatricyclo[6.4.0.0$^{2,6}$]dodeca-1(12),3,5,8,10-pentaene-4-carboxamide $^1$H NMR (500 MHz, DMSO) 10.04 (s, 1H), 8.99 (s, 1H), 8.08 (d, J=8.9 Hz, 1H), 8.01 (d, J=9.8 Hz, 1H), 7.71 (d, J=2.1 Hz, 1H), 7.17 (dd, J=8.9, 2.2 Hz, 1H), 7.02 (d, J=9.8 Hz, 1H), 3.84 (s, 3H), 3.61 (s, 3H). Tr(METCR1600)=3.67 min, m/z (ES$^+$) (M+H)$^+$ 356.

The following example was prepared using Method 5 described above:

TABLE 5

| Ex. | Structure | Mol. Weight | IUPAC Name | LCMS data |
|-----|-----------|-------------|------------|-----------|
| 1 | 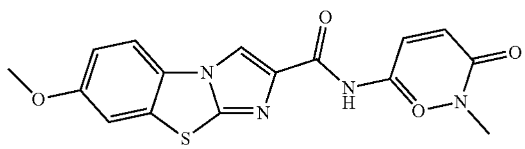 | 355.37 | 10-methoxy-N-(1-methyl-6-oxo-1,6-dihydropyridazin-3-yl)-7-thia-2,5-diazatricyclo[6.4.0.0$^{2,6}$]dodeca-1(12),3,5,8,10-pentaene-4-carboxamide | Tr(METCR 1600) = 3.67 min, m/z (ES$^+$) (M + H)$^+$ 356 |

Method 6

Scheme for Method 6

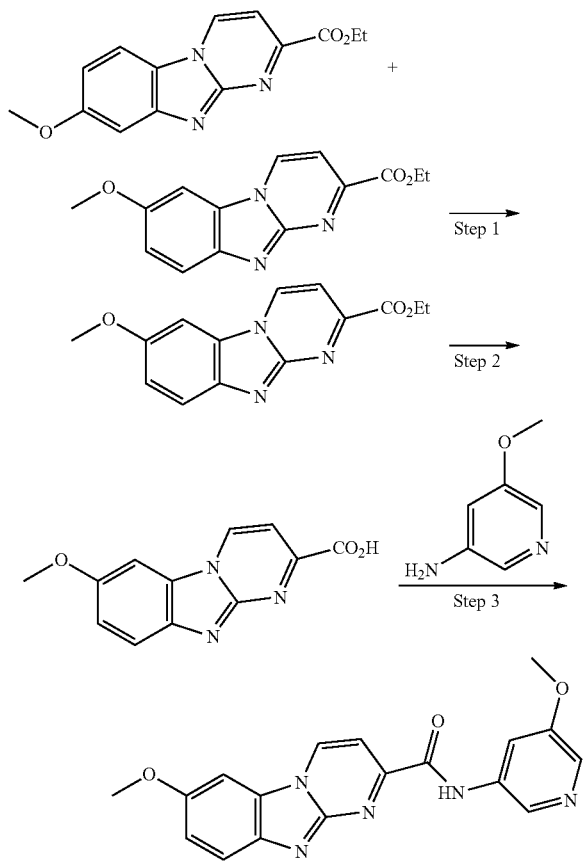

Step 1, Method 6: Ethyl 4-methoxy-1,8,10-triazatricyclo[7.4.0.0$^{2,7}$]trideca-2(7),3,5,8,10,12-hexaene-11-carboxylate A 1:4 mixture of ethyl 4-methoxy-1,8,10-triazatricyclo[7.4.0.0$^{2,7}$]trideca-2(7),3,5,8,10,12-hexaene-11-carboxylate and ethyl 5-methoxy-1,8,10-triazatricyclo[7.4.0.0$^{2,7}$]trideca-2(7),3,5,8,10,12-hexaene-11-carboxylate (356 mg, prepared by Method 19) was purified by FCC (silica, 0 to 40% dichloromethane in ethyl acetate) to give ethyl 4-methoxy-1,8,10-triazatricyclo[7.4.0.0$^{2,7}$]trideca-2(7),3,5,8,10,12-hexaene-11-carboxylate. $^1$H NMR (300 MHz, DMSO) 9.64 (d, J=5.4 Hz, 1H), 8.03 (d, J=2.4 Hz, 1H), 7.87 (d, J=9.0 Hz, 1H), 7.61 (d, J=6.9 Hz, 1H), 7.27 (dd, J=9.0, 2.4 Hz, 1H), 4.43 (q, J=6.9 Hz, 2H), 3.91 (s, 3H), 1.39 (t, J=6.9 Hz, 3H).

Step 2, Method 6: 4-Methoxy-1,8,10-triazatricyclo[7.4.0.0$^{2,7}$]trideca-2(7),3,5,8,10,12-hexaene-11-carboxylic acid dihydrate Ethyl 4-methoxy-1,8,10-triazatricyclo[7.4.0.0$^{2,7}$]trideca-2(7),3,5,8,10,12-hexaene-11-carboxylate (100 mg, 0.369 mmol) was suspended in 6 N aqueous hydrochloric acid and heated at 95° C. for 4 hours. The reaction mixture was cooled to room temperature. The resulting solid was collected by filtration, redissolved in saturated aqueous sodium bicarbonate solution (30 mL) and the aqueous solution extracted with ethyl acetate (3×30 mL). The pH of the aqueous phase was adjusted to 1 with concentrated hydrochloric acid, and the resulting solid collected by filtration, washed with water (10 mL) and dried under reduced pressure at room temperature. The solid was then suspended in water (3 mL), sonicated, isolated by filtration and dried in vacuo at room temperature for 18 hours to give the title compound. mp 256-257° C. (dec); $^1$H NMR (500 MHz, DMSO) 13.89 (br s, 1H), 9.63 (d, J=7.0 Hz, 1H), 8.03 (d, J=1.0 Hz, 1H), 7.86 (d, J=9.0 Hz, 1H), 7.61 (d, J=7.0 Hz, 1H), 7.27 (dd, J=9.0, 2.4 Hz, 1H), 3.90 (s, 3H).

Step 3, Method 6: 4-Methoxy-N-(5-methoxypyridin-3-yl)-1,8,10-triazatricyclo[7.4.0.0$^{2,7}$]trideca-2(7),3,5,8,10,12-hexaene-11-carboxamide 4-Methoxy-1,8,10-triazatricyclo[7.4.0.0$^{2,7}$]trideca-2(7),3,5,8,10,12-hexaene-11-carboxylic acid dihydrate (25 mg, 0.1 mmol), 1-[bis(dimethylamino)methylene]-1H-1,2,3-triazolo[4,5-b]pyridinium 3-oxide hexafluorophosphate (42 mg, 0.11 mmol) and ethyldiisopropylamine (39 μl, 0.22 mmol) were dissolved in anhydrous N,N-dimethylformamide (1 ml) and allowed to stir for 30 minutes. 5-Methoxypyridin-3-amine (13. mg, 0.11 mmol) was added and the reaction stirred at room temperature for 16 hours. Further portions of 1-[bis(dimethylamino)methylene]-1H-1,2,3-triazolo[4,5-b]pyridinium 3-oxide hexafluorophosphate (10 mg, 0.03 mmol), ethyldiisopropylamine (9 µl, 0.05 mmol) and 5-methoxypyridin-3-amine (5 mg, 0.04 mmol) were added and the reaction stirred at room temperature for 3 hours. The reaction mixture was concentrated in vacuo and water and ethyl acetate were added. The mixture was filtered to give the title compound.

Example 1, Method 6: 4-Methoxy-N-(5-methoxypyridin-3-yl)-1,8,10-triazatricyclo[7.4.0.0$^{2,7}$]trideca-2(7),3,5,8,10,12-hexaene-11-carboxamide 1H NMR (500 MHz, DMSO) 11.11 (s, 1H), 9.68 (d, J=6.9 Hz, 1H), 8.82 (s, 1H), 8.11 (d, J=2.0 Hz, 1H), 8.03 (m, 2H), 7.87 (d, J=8.9 Hz, 1H), 7.73 (d, J=6.9 Hz, 1H), 7.32-7.22 (m, 1H), 3.92 (s, 3H), 3.86 (s, 3H). Tr(MET-uHPLC-AB-101)=1.98 min, m/z (ES$^+$) (M+H)$^+$ 350.

The following example was prepared using Method 6 described above:

TABLE 6

| Ex. | Structure | Mol. Weight | IUPAC Name | LCMS data |
|---|---|---|---|---|
| 1 | 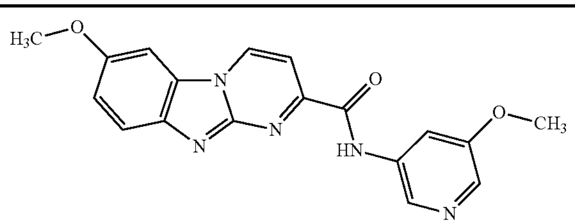 | 349.35 | 4-methoxy-N-(5-methoxypyridin-3-yl)-1,8,10-triazatricyclo[7.4.0.0$^{2,7}$]trideca-2(7),3,5,8,10,12-hexaene-11-carboxamide | Tr(MET-uHPLC-AB-101) = 1.98 min, m/z (ES$^+$) (M + H)$^+$ 350 |

Step 1, Method 7: (3-{10-Methoxy-7-thia-2,5-diazatricyclo[6.4.0.0$^{2-6}$]dodeca-1(12),3,5,8,10-pentaene-4-amido}pyridin-1-ium-1-olate A suspension of 10-methoxy-N-(pyridin-3-yl)-7-thia-2,5-diazatricyclo[6.4.0.0$^{2,6}$]dodeca-1(12),3,5,8,10-pentaene-4-carboxamide (100 mg, 0.308 mmol, prepared by Method 1) and 3-chloroperbenzoic acid (91 mg, 0.370 mmol) in chloroform (10 mL) was stirred for 2 days. Water was added and the solid collected by vacuum filtration. The solid was washed with ethyl acetate and water and dried under suction. The solid was suspended in methanol and transfered to a round bottomed flask. The volatiles were removed and the residue purified by neutral prep-HPLC to give the title compound.

Method 7

Scheme for Method 7

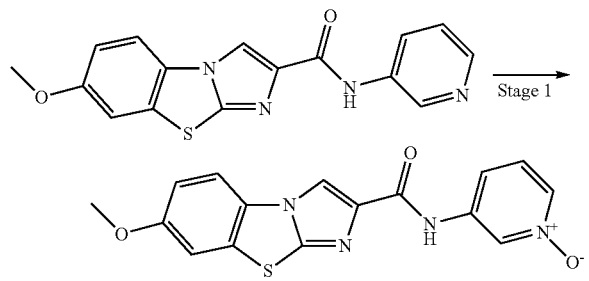

Example 1, Method 7: (3-{10-Methoxy-7-thia-2,5-diazatricyclo[6.4.0.0$^{2,6}$]dodeca-1(12),3,5,8,10-pentaene-4-amido}pyridin-1-ium-1-olate $^1$H NMR (500 MHz, DMSO) 10.60 (s, 1H), 9.01-8.95 (m, 1H), 8.51-8.44 (m, 1H), 8.11 (d, J=8.9 Hz, 1H), 7.91 (t, J=1.3 Hz, 1H), 7.81 (d, J=8.8 Hz, 1H), 7.72 (d, J=2.5 Hz, 1H), 7.19 (dd, J=8.9, 2.5 Hz, 1H), 7.14-7.09 (m, 1H), 3.85 (s, 3H). Tr(MET-uHPLC-AB-101)=1.92 min, m/z (ES$^+$) (M+H)$^+$ 341.

The following example was prepared using Method 7 described above:

TABLE 7

| Ex. | Structure | Mol. Weight | IUPAC Name | LCMS data |
|---|---|---|---|---|
| 1 | 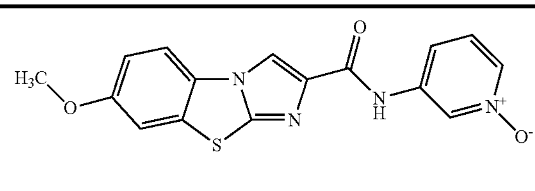 | 340.36 | 3-{10-methoxy-7-thia-2,5-diazatricyclo[6.4.0.0$^{2,6}$]dodeca-1(12),3,5,8,10-pentaene-4-amido}pyridin-1-ium-1-olate | Tr(MET-uHPLC-AB-101) = 2.13 min, m/z (ES$^+$) (M + H)$^+$ 341 |

Method 8

Scheme for Method 8

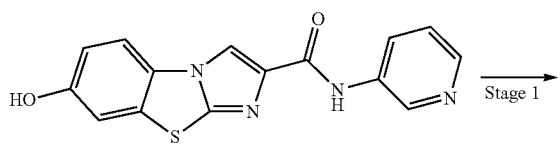

Stage 1

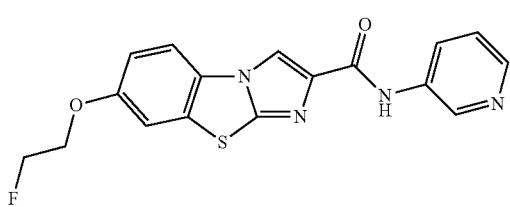

Step 1, Method 8: 10-(2-Fluoroethoxy)-N-(pyridin-3-yl)-7-thia-2,5-diazatricyclo[6.4.0.0$^{2,6}$]dodeca-1(8),3,5,9,11-pentaene-4-carboxamide 10-Hydroxy-N-(pyridin-3-yl)-7-thia-2,5-diazatricyclo[6.4.0.0$^{2,6}$]dodeca-1(8),3,5,9,11-pentaene-4-carboxamide (140 mg, 0.45 mmol, prepared by Method 2) was dissolved in toluene (3 mL) and 2-fluoroethan-1-ol (38 mg, 0.59 mmol) was added, followed by (tributyl-lambda~5~-phosphanylidene)acetonitrile (154 µl, 0.59 mmol), and the reaction mixture stirred at ambient temperature under a nitrogen atmosphere for 16 hours. The reaction mixture was poured onto water and the resulting emulsion filtered. The residual solid was triturated with ethyl acetate and the solid dried under vacuum to give the title compound.

Example 1, Method 8: 10-(2-Fluoroethoxy)-N-(pyridin-3-yl)-7-thia-2,5-diazatricyclo[6.4.0.0$^{2,6}$]dodeca-1(8),3,5,9,11-pentaene-4-carboxamide $^1$H NMR (500 MHz, DMSO) 10.42 (s, 1H), 9.04 (d, J=2.2 Hz, 1H), 8.97 (s, 1H), 8.33-8.24 (m, 2H), 8.12 (d, J=8.9 Hz, 1H), 7.75 (d, J=2.4 Hz, 1H), 7.37 (dd, J=8.2, 4.7 Hz, 1H), 7.24 (dd, J=8.9, 2.5 Hz, 1H), 4.91-4.68 (m, 2H), 4.41-4.25 (m, 2H). Tr(MET-uHPLC-AB-101)=1.96 min, m/z (ES$^+$) (M+H)$^+$ 357.

The following examples were prepared using Method 8 described above:

TABLE 8

| Ex. | Structure | Mol. Weight | IUPAC Name | LCMS data |
|---|---|---|---|---|
| 1 | 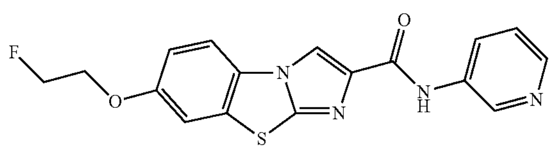 [SMILES: O=C(Nc1cccnc1)c1cn2c(n1)sc1cc(OCCF)ccc12] | 356.37 | 10-(2-fluoroethoxy)-N-(pyridin-3-yl)-7-thia-2,5-diazatricyclo[6.4.0.0$^{2,6}$]dodeca-1(8),3,5,9,11-pentaene-4-carboxamide | Tr(MET-uHPLC-AB-101) = 1.96 min, m/z (ES$^+$) (M + H)$^+$ 357 |
| 2 | 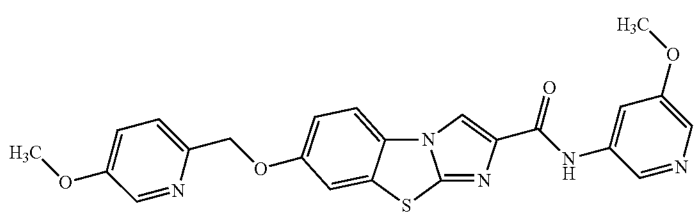 [SMILES: COc1ccc(COc2ccc3c(c2)sc2nc(C(=O)Nc4cncc(OC)c4)cn23)nc1] | 461.50 | 10-[(5-methoxypyridin-2-yl)methoxy]-N-(5-methoxypyridin-3-yl)-7-thia-2,5-diazatricyclo[6.4.0.0$^{2,6}$]dodeca-1(12),3,5,8,10-pentaene-4-carboxamide | Tr(MET-uHPLC-AB-101) = 2.57 min, m/z (ES$^+$) (M + H)$^+$ 462 |

Method 9

Scheme for Method 9

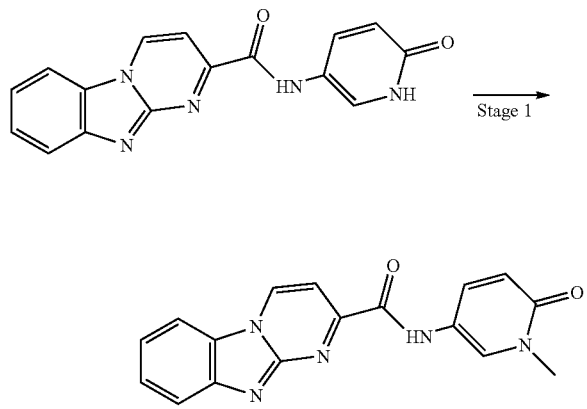

Step 1, Method 9: N-(1-Methyl-6-oxo-1,6-dihydro-pyridin-3-yl)-1,8,10-triazatricyclo[7.4.0.0²,⁷]trideca-2(7),3,5,8,10,12-hexaene-11-carboxamide N-(6-Oxo-1,6-dihydropyridin-3-yl)-1,8,10-triazatricyclo[7.4.0.0$^{2,7}$]trideca-2(7),3,5,8,10,12-hexaene-11-carboxamide (90%, 30 mg, 0.09 mmol, prepared by Method 3) and Caesium carbonate (58 mg, 0.18 mmol) were suspended in anhydrous N,N-dimethylformamide (3 mlL), methyliodide (12 µl, 0.19 mmol) was added and the reaction stirred at 60° C. for 2 hours. The solvents were removed in vacuo and the residue triturated with water (5 ml) and filtered. The residue was purified by neutral HPLC to give the title compound.

Example 1, Method 9: N-(1-methyl-6-oxo-1,6-dihydropyridin-3-yl)-1,8,10-triazatricyclo[7.4.0.0$^{2,7}$]trideca-2(7),3,5,8,10,12-hexaene-11-carboxamide $^1$H NMR (500 MHz, DMSO) 10.86 (s, 1H), 9.75 (d, J=7.0 Hz, 1H), 8.42 (d, J=8.2 Hz, 1H), 8.38 (d, J=2.8 Hz, 1H), 7.95 (d, J=8.2 Hz, 1H), 7.86 (dd, J=9.7, 2.9 Hz, 1H), 7.72 (d, J=7.0 Hz, 1H), 7.66-7.57 (m, 1H), 7.58-7.47 (m, 1H), 6.45 (d, J=9.7 Hz, 1H), 3.48 (s, 3H). Tr(MET-uHPLC-AB-101)=1.54 min, m/z (ES⁺) (M+H)⁺ 320.

The following example was prepared using Method 9 described above:

Method 10

Scheme for Method 10

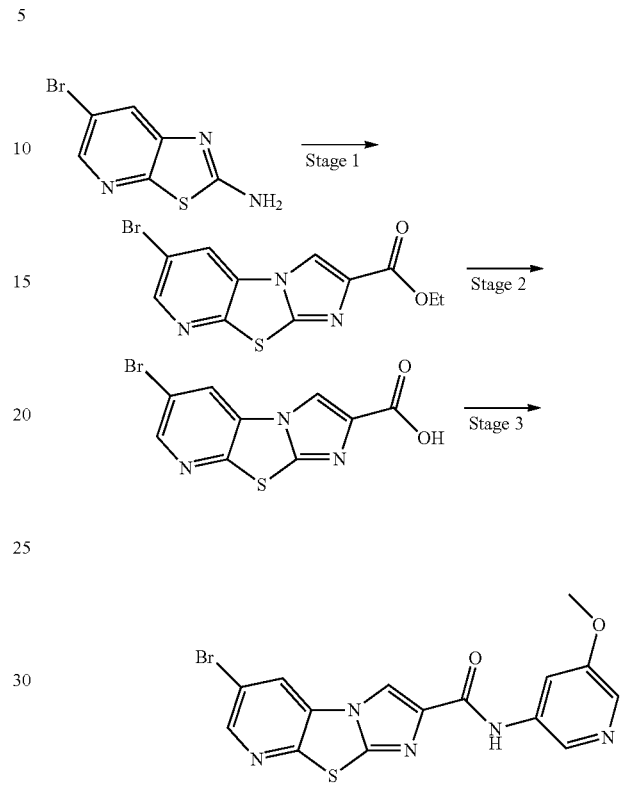

Step 1, Method 10: Ethyl 11-bromo-7-thia-2,5,9-triazatricyclo[6.4.0.0$^{2,6}$]dodeca-1(12),3,5,8,10-pentaene-4-carboxylate 6-Bromo-[1,3]thiazolo[5,4-b]pyridin-2-amine (0.1 g, 0.43 mmol) was dissolved in N-methyl-2-pyrrolidone (1.5 mL) and ethyl 3-bromo-2-oxopropanoate (64 µl, 0.43 mmol) added dropwise. The reaction was stirred at room temperature for 1 hour then heated to 60° C. overnight. The reaction was cooled then water/ice added. The resulting precipitate was isolated by vacuum filtration. The red solid was further dried in a vacuum oven to give the title compound. $^1$H NMR (500 MHz, DMSO) 9.05 (s, 1H), 8.95 (d, J=2.1 Hz, 1H), 8.74 (d, J=2.1 Hz, 1H), 4.32 (q, J=7.1 Hz, 2H), 1.33 (t, J=7.1 Hz, 3H). Tr(MS10)=1.55 min, m/z (ES⁺) (M+H)⁺ 328, 329

TABLE 9

| Ex. | Structure | Mol. Weight | IUPAC Name | LCMS data |
|---|---|---|---|---|
| 1 | 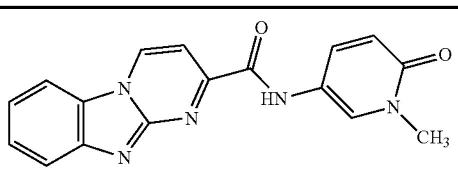 | 319.32 | N-(1-methyl-6-oxo-1,6-dihydropyridin-3-yl)-1,8,10-triazatricyclo[7.4.0.0$^{2,7}$]trideca-2(7),3,5,8,10,12-hexaene-11-carboxamide | Tr(MET-uHPLC-AB-101) = 1.54 min, m/z (ES⁺) (M + H)⁺ 320 |

Step 2, Method 10: 11-Bromo-7-thia-2,5,9-triazatricyclo[6.4.0.0²,⁶]dodeca-1(12),3,5,8,10-pentaene-4-carboxylic acid Ethyl 11-bromo-7-thia-2,5,9-triazatricyclo[6.4.0.0²,⁶]dodeca-1(12),3,5,8,10-pentaene-4-carboxylate (88%, 89 mg, 0.24 mmol) was suspended in methanol:toluene (1:1). Palladium(II) acetate (1:2) (2 mg, 0.002 mmol) and 5-(di-tert-butylphosphanyl)-1',3',5'-triphenyl-1'H-1,4'-bipyrazole (2 mg, 0.005 mmol) were added followed by caesium carbonate (117 mg, 0.36 mmol) and the reaction stirred at 80° C. overnight. The reaction mixture was allowed to cool, then concentrated in vacuo. Water and ethyl acetate were added to form a slurry. 2 N Hydrochloric acid was added until pH 1. The precipitate was isolated by filtration to give the title compound. ¹H NMR (500 MHz, DMSO) 12.85 (s, 1H), 8.96 (s, 1H), 8.93 (d, J=2.1 Hz, 1H), 8.73 (d, J=2.1 Hz, 1H). Tr(METCR1410)=0.89 min, m/z (ES⁺) (M+H)⁺ 300, 302

Step 3, Method 110: 11-Methoxy-N-(5-methoxypyridin-3-yl)-7-thia-2,5,9-triazatricyclo[6.4.0.0²,⁶]dodeca-1(12),3,5,8,10-pentaene-4-carboxamide 11-Bromo-7-thia-2,5,9-triazatricyclo[6.4.0.0²,⁶]dodeca-1(12),3,5,8,10-pentaene-4-carboxylic acid (60 mg, 0.2 mmol) and 5-methoxypyridin-3-amine (25 mg, 0.2 mmol) were combined in pyridine (3 mL) and stirred for 10 minutes. N-(3-Dimethylaminopropyl)-N'-ethylcarbodiimide hydrochloride (46 mg, 0.24 mmol) was added and the solution stirred overnight at room temperature. Water was added then the solution concentrated to dryness. The crude solid was slurried with water and isolated by filtration to give the title compound.

Example 1, Method 10: 11-Bromo-N-(5-methoxypyridin-3-yl)-7-thia-2,5,9-triazatricyclo[6.4.0.0²,⁶]dodeca-1(12),3,5,8,10-pentaene-4-carboxamide ¹H NMR (500 MHz, DMSO) 10.51 (s, 1H), 9.00 (s, 1H), 8.98 (d, J=2.0 Hz, 1H), 8.73 (m, 2H), 8.05 (d, J=2.6 Hz, 1H), 7.98 (appt t, J=2.3 Hz, 1H), 3.83 (s, 3H). Tr(MET-uHPLC-AB-101)=2.4 min, m/z (ES⁺) (M+H)⁺ 404, 406.

The following example was prepared using Method 10 described above:

Method 11

Scheme for Method 11

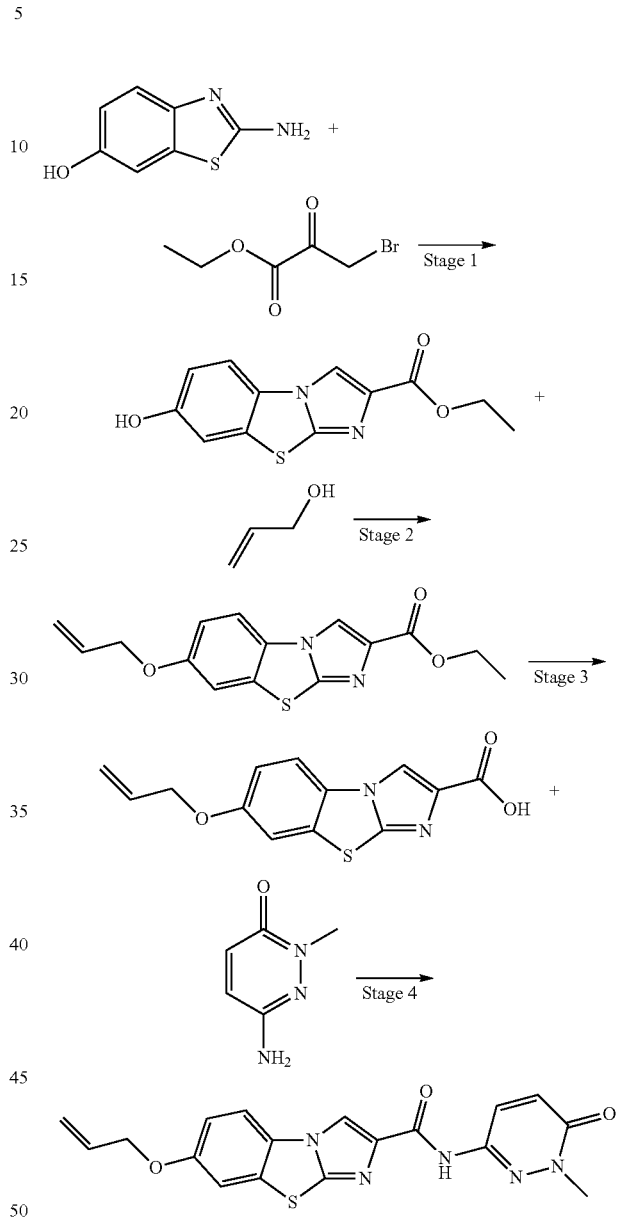

TABLE 10

| Ex. | Structure | Mol. Weight | IUPAC Name | LCMS data |
|---|---|---|---|---|
| 1 | 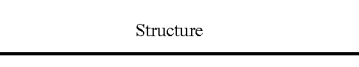 | 404.24 | 11-bromo-N-(5-methoxypyridin-3-yl)-7-thia-2,5,9-triazatricyclo[6.4.0.0²,⁶]dodeca-1(12),3,5,8,10-pentaene-4-carboxamide | Tr(MET-uHPLC-AB-101) = 2.4 min, m/z (ES⁺) (M + H)⁺ 404, 406 |

Step 1, Method 11: Ethyl 10-hydroxy-7-thia-2,5-diazatricyclo[6.4.0.0²,⁶]dodeca-1(12),3,5,8,10-pentaene-4-carboxylate Ethyl 3-bromo-2-oxopropanoate (4.2 mL, 33.1 mmol) was added dropwise to a stirred solution of 2-amino-1,3-benzothiazol-6-ol (5 g, 30.1 mmol) in N,N-dimethylacetamide (100 mL) at room temperature. The reaction mixture was heated to 100° C. for 3 hours. The reaction was cooled to room temperature and water (200 mL) added. A precipitate formed and the mixture was filtered. The collected solid was dried under vacuum to give the title compound. $^1$H NMR (500 MHz, DMSO) 10.03 (s, 1H), 8.89 (s, 1H), 7.95 (d, J=8.7 Hz, 1H), 7.38 (d, J=2.3 Hz, 1H), 6.94 (dd, J=8.8, 2.3 Hz, 1H), 4.28 (q, J=7.1 Hz, 2H), 1.30 (t, J=7.1 Hz, 3H). Tr(METCR1410)=0.91 min, m/z (ES$^+$) (M+H)$^+$ 263.

Step 2, Method 11: Ethyl 10-(prop-2-en-1-yloxy)-7-thia-2,5-diazatricyclo[6.4.0.0²,⁶]dodeca-1(12),3,5,8,10-pentaene-4-carboxylate Ethyl 10-hydroxy-7-thia-2,5-diazatricyclo[6.4.0.0²,⁶]dodeca-1(12),3,5,8,10-pentaene-4-carboxylate (500 mg, 1.91 mmol) and prop-2-en-1-ol (178 µL, 2.48 mmol) were suspended in anhydrous toluene (5 mL), cyanomethylenetributylphosphorane (650 µL, 2.48 mmol) was added and the reaction heated to 100° C. in a sealed tube for 2 hours. The reaction mixture was cooled to room temperature and the solvents removed in vacuo. The residue was triturated with 1:1 diethyl ether:heptane to give the title compound. $^1$H NMR (500 MHz, DMSO) 8.96 (s, 1H), 8.08 (d, J=8.9 Hz, 1H), 7.70 (d, J=2.5 Hz, 1H), 7.18 (dd, J=8.9, 2.5 Hz, 1H), 6.07 (ddt, J=17.2, 10.6, 5.3 Hz, 1H), 5.43 (dq, J=17.3, 1.6 Hz, 1H), 5.29 (dd, J=10.5, 1.5 Hz, 1H), 4.60-4.68 (m, 2H), 4.29 (q, J=7.1 Hz, 2H), 1.31 (t, J=7.1 Hz, 3H). Tr(METCR1410)=1.13 min, m/z (ES$^+$) (M+H)$^+$ 303.

Step 3, Method 11: 10-(Prop-2-en-1-yloxy)-7-thia-2,5-diazatricyclo[6.4.0.0²,⁶]dodeca-1(12),3,5,8,10-pentaene-4-carboxylic acid Ethyl 10-(prop-2-en-1-yloxy)-7-thia-2,5-diazatricyclo[6.4.0.0²,⁶]dodeca-1(12),3,5,8,10-pentaene-4-carboxylate (95%, 445 mg, 1.4 mmol) was suspended in 1:1 tetrahydrofuran/water (8 mL), lithium hydroxide (67 mg, 2.8 mmol) added and the reaction was stirred at room temperature for 2 days. The reaction mixture was acidified to approximately pH 4 by the addition of 2 M hydrochloric acid, a precipitate formed which was collected by filtration to give the title compound. $^1$H NMR (500 MHz, DMSO) 12.60 (s, 1H), 8.88 (s, 1H), 8.05 (d, J=8.9 Hz, 1H), 7.69 (d, J=2.5 Hz, 1H), 7.17 (dd, J=8.9, 2.5 Hz, 1H), 6.07 (ddt, J=17.2, 10.6, 5.3 Hz, 1H), 5.44 (dd, J=17.3, 1.7 Hz, 1H), 5.29 (dd, J=10.5, 1.5 Hz, 1H), 4.64 (d, J=5.3 Hz, 2H). Tr(METCR1410)=0.97 min, m/z (ES$^+$) (M+H)$^+$ 275.

Step 4, Method 11: N-(1-Methyl-6-oxo-1,6-dihydropyridazin-3-yl)-10-(prop-2-en-1-yloxy)-7-thia-2,5-diazatricyclo[6.4.0.0²,⁶]dodeca-1(12),3,5,8,10-pentaene-4-carboxamide 10-(Prop-2-en-1-yloxy)-7-thia-2,5-diazatricyclo[6.4.0.0²,⁶]dodeca-1(12),3,5,8,10-pentaene-4-carboxylic acid (275 mg, 1 mmol), 6-amino-2-methyl-2,3-dihydropyridazin-3-one (138 mg, 1.1 mmol), 1-[bis(dimethylamino)methylene]-1H-1,2,3-triazolo[4,5-b]pyridinium 3-oxide hexafluorophosphate (419 mg, 1.1 mmol) and ethyldiisopropylamine (0.52 ml, 3.01 mmol) were dissolved in N,N-dimethylformamide (10 mL) and the reaction mixture stirred at room temperature for 45 minutes. The reaction mixture was then heated to 60° C. for two days. After this time the reaction mixture was cooled to room temperature, water added and the resultant precipitate collected by filtration and triturated with methanol to give the title compound.

Example 1, Method 11: N-(1-Methyl-6-oxo-1,6-dihydropyridazin-3-yl)-10-(prop-2-en-1-yloxy)-7-thia-2,5-diazatricyclo[6.4.0.0²,⁶]dodeca-1(12),3,5,8,10-pentaene-4-carboxamide $^1$H NMR (500 MHz, DMSO) 10.08 (s, 1H), 9.00 (s, 1H), 8.08 (d, J=8.9 Hz, 1H), 8.01 (d, J=9.8 Hz, 1H), 7.73 (d, J=2.5 Hz, 1H), 7.20 (dd, J=8.9, 2.5 Hz, 1H), 7.03 (d, J=9.8 Hz, 1H), 6.16-5.97 (m, 1H), 5.44 (dd, J=17.3, 1.6 Hz, 1H), 5.30 (dd, J=10.5, 1.4 Hz, 1H), 4.65 (d, J=5.3 Hz, 2H), 3.61 (s, 3H). Tr(MET-uHPLC-AB-101)=2.97 min, m/z (ES$^+$) (M+H)$^+$ 382.

The following example was prepared using Method 11 described above:

TABLE 11

| Ex. | Structure | Mol. Weight | IUPAC Name | LCMS data |
|---|---|---|---|---|
| 1 | 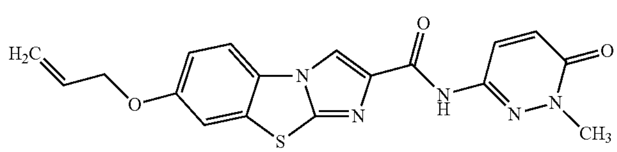 [SMILES: C=CCOc1ccc2c(c1)sc1nc(C(=O)Nc3ccc(=O)n(C)n3)cn12] | 381.41 | N-(1-methyl-6-oxo-1,6-dihydropyridazin-3-yl)-10-(prop-2-en-1-yloxy)-7-thia-2,5-diazatricyclo[6.4.0.0²,⁶]dodeca-1(12),3,5,8,10-pentaene-4-carboxamide | Tr(MET-uHPLC-AB-101) = 2.97 min, m/z (ES$^+$) (M + H)$^+$ 382 |

Method 12

Scheme for Method 12

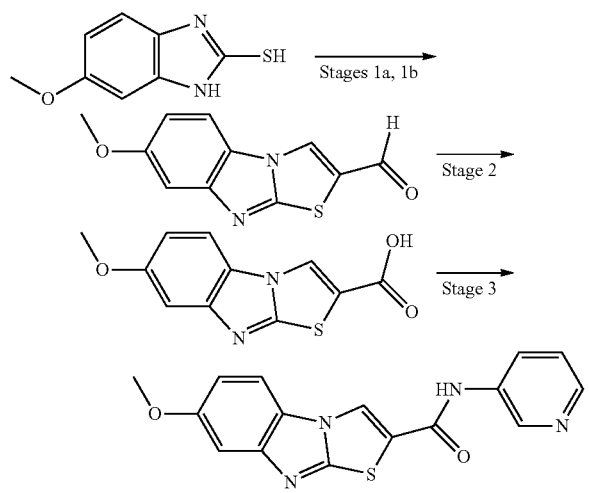

Step 1, Method 12: 10-Methoxy-5-thia-2,7-diazatricyclo[6.4.0.0$^{2,6}$]dodeca-1(12),3,6,8,10-pentaene-4-carbaldehyde Part 1

A suspension of 6-methoxy-1H-1,3-benzodiazole-2-thiol (5.00 g, 27.74 mmol), bromopropanedial (4.19 g, 27.74 mmol), and potassium carbonate (3.83 g, 27.74 mmol) in N,N-dimethylformamide was heated to 80° C. for 4 hours, cooled, the solvents removed in vacuo and the residue diluted with water (100 mL). The pH was adjusted to about 5 with 1 M hydrochloric acid, at which point a solid formed. The solid was isolated by filtration and rinsed with water to afford the crude intermediate di-aldehyde, which was used directly in the next part with no further purification.

Part 2

The solids from part 1 were dissolved in acetic acid:N,N-dimethylformamide (20 mL, 3:1) and heated to 120° C. for 40 minutes. The reaction mixture was cooled and the solvents removed in vacuo. The residue was diluted with water (100 mL) and the resulting solids filtered off to give a regioisomeric mixture of aldehydes (3:2 in favour of the desired isomer—as determined by NMR). The crude mixture was filtered through a pad of silica, then recrystallised twice from methanol-ethyl acetate to give the title compound: $^1$H NMR (250 MHz, DMSO) 9.97 (s, 1H), 9.43 (s, 1H), 7.99 (d, J=8.8 Hz, 1H), 7.26 (d, J=2.3 Hz, 1H), 6.98 (dd, J=8.9, 2.4 Hz, 1H), 3.83 (s, 3H).). Tr(METCR1410)= 1.05 min, m/z (ES$^+$) (M+H)$^+$ 231.

Step 2, Method 12: 10-Methoxy-5-thia-2,7-diazatricyclo[6.4.0.0$^{2,6}$]dodeca-1(12),3,6,8,10-pentaene-4-carboxylic acid To a suspension of 10-methoxy-5-thia-2,7-diazatricyclo[6.4.0.0$^{2,6}$]dodeca-1(12),3,6,8,10-pentaene-4-carbaldehyde (180 mg, 0.77 mmol) in water-tertiary butanol (1:3, 8 mL) was added 2-methylbut-2-ene (163 mg, 2.32 mmol), sodium dihydrogen phosphate (372 mg, 3.1 mmol) and sodium chlorite (80%, 263 mg, 2.32 mmol). The resulting orange suspension was stirred overnight at room temperature. The bulk of the solvents were removed in vacuo, the residue dissolved in water-acetonitrile and purified by acid phase preparative HPLC to afford the title compound. $^1$H NMR (250 MHz, DMSO) 9.20 (s, 1H), 8.00 (d, J=8.9 Hz, 1H), 7.23 (d, J=2.3 Hz, 1H), 6.94 (dd, J=8.9, 2.4 Hz, 1H), 3.82 (s, 3H). Tr(METCR1410)=0.88 min, m/z (ES$^+$) (M+H)$^+$ 246.

Step 3, Method 12: 10-Methoxy-N-(5-methoxypyridin-3-yl)-5-thia-2,7-diazatricyclo[6.4.0.0$^{2,6}$]dodeca-1(12),3,6,8,10-pentaene-4-carboxamide To a solution of 10-methoxy-5-thia-2,7-diazatricyclo[6.4.0.0$^{2,6}$]dodeca-1(12),3,6,8,10-pentaene-4-carboxylic acid (32 mg, 0.13 mmol) and 5-methoxypyridin-3-amine (18 mg, 0.14 mmol) in pyridine (2 mL) was added N-(3-dimethylaminopropyl)-N'-ethylcarbodiimide hydrochloride (32 mg, 0.17 mmol). The reaction was stirred at room temperature for 45 minutes before water was slowly added (5 mL) and the resulting slurry stirred for a further 15 minutes. The resulting solid was filtered off and dried to give the title compound.

Example 1, Method 12: 10-Methoxy-N-(5-methoxypyridin-3-yl)-5-thia-2,7-diazatricyclo[6.4.0.0$^{2,6}$]dodeca-1(12),3,6,8,10-pentaene-4-carboxamide $^1$H NMR (500 MHz, DMSO) 10.75 (s, 1H), 9.20 (s, 1H), 8.50 (d, J=2.0 Hz, 1H), 8.10 (d, J=2.6 Hz, 1H), 7.89 (d, J=8.8 Hz, 1H), 7.80 (appt t, J=2.3 Hz, 1H), 7.27 (d, J=2.3 Hz, 1H), 6.97 (dd, J=8.8, 2.4 Hz, 1H), 3.85 (s, 3H), 3.84 (s, 3H). Tr(METCR1600)=3.9 min, m/z (ES$^+$) (M+H)$^+$ 355.

The following examples were prepared using Method 12 described above:

TABLE 12

| Ex. | Structure | Mol. Weight | IUPAC Name | LCMS data |
|---|---|---|---|---|
| 1 | 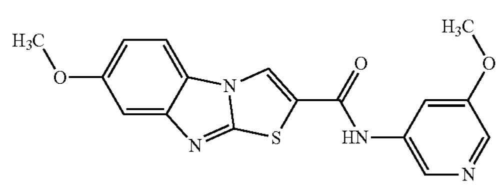 [SMILES: COc1cncc(NC(=O)c2cn3c(nc4cc(OC)ccc43)s2)c1] | 354.38 | 10-methoxy-N-(5-methoxypyridin-3-yl)-5-thia-2,7-diazatricyclo[6.4.0.0$^{2,6}$]dodeca-1(12),3,6,8,10-pentaene-4-carboxamide | Tr(METCR1600) = 3.9 min, m/z (ES$^+$) (M + H)$^+$ 355 |

TABLE 12-continued

| Ex. | Structure | Mol. Weight | IUPAC Name | LCMS data |
|---|---|---|---|---|
| 2 | 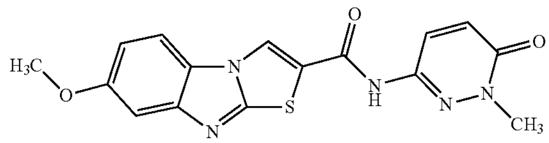 [SMILES: COc1ccc2c(c1)nc1sc(C(=O)Nc3ccc(=O)n(C)n3)cn12] | 355.37 | 10-methoxy-N-(1-methyl-6-oxo-1,6-dihydropyridazin-3-yl)-5-thia-2,7-diazatricyclo[6.4.0.0²,⁶]dodeca-1(12),3,6,8,10-pentaene-4-carboxamide | Tr(MET-uHPLC-AB-101) = 2.06 min, m/z (ES⁺) (M + H)⁺ 356 |
| 3 | 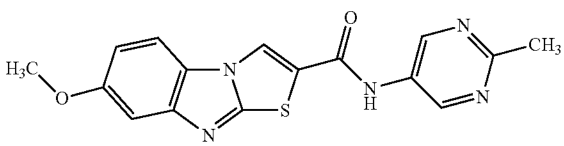 | 339.37 | 10-methoxy-N-(2-methylpyrimidin-5-yl)-5-thia-2,7-diazatricyclo[6.4.0.0²,⁶]dodeca-1(8),3,6,9,11-pentaene-4-carboxamide | Tr(MET-uHPLC-AB-101) = 2.15 min, m/z (ES⁺) (M + H)⁺ 340.1 |

Method 13

Scheme for Method 13

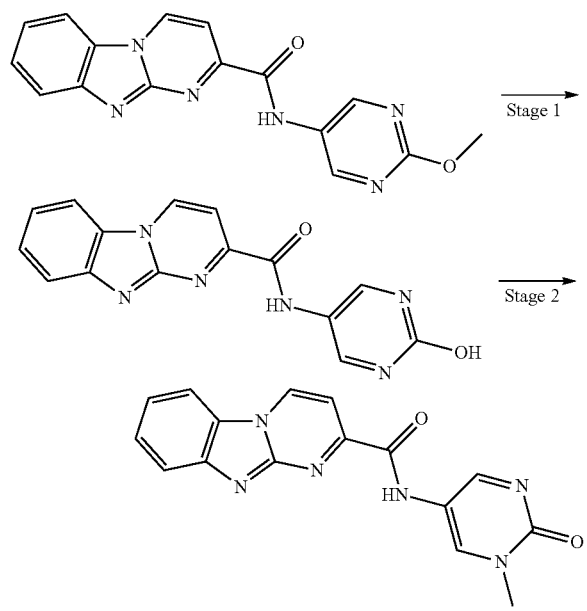

Step 1, Method 13: N-(2-Hydroxypyrimidin-5-yl)-1,8,10-triazatricyclo[7.4.0.0²,⁷]trideca-2(7),3,5,8,10,12-hexaene-11-carboxamide N-(2-Methoxypyrimidin-5-yl)-1,8,10-triazatricyclo[7.4.0.0²,⁷]trideca-2(7),3,5,8,10,12-hexaene-11-carboxamide (154 mg, 0.48 mmol, prepared by Method 3) was suspended in dichloromethane (15 mL) and 1 M tribromoborane (6.7 mL) added dropwise. The reaction mixture was stirred at room temperature under a nitrogen atmosphere for 4.5 days. The reaction mixture was quenched with water (20 mL) and the mixture concentrated in vacuo. The residue was suspended in tetrahydrofuran (40 mL) and the pH increased to 7 by the addition of saturated aqueous sodium hydrogen carbonate solution. The mixture was filtered to give the title compound. ¹H NMR (500 MHz, DMSO) 10.86 (s, 1H), 9.75 (d, J=7.0 Hz, 1H), 8.60 (s, 2H), 8.42 (d, J=8.2 Hz, 1H), 7.95 (d, J=8.2 Hz, 1H), 7.73 (d, J=7.0 Hz, 1H), 7.63 (appt t, J=7.7 Hz, 1H), 7.52 (appt t, J=7.7 Hz, 1H). Tr(METCR1410)=0.77 min, m/z (ES⁺) (M+H)⁺ 307.

Step 2, Method 13: N-(1-Methyl-2-oxo-1,2-dihydropyrimidin-5-yl)-1,8,10-triazatricyclo[7.4.0.0²,⁷]trideca-2(7),3,5,8,10,12-hexaene-11-carboxamide N-(2-Hydroxypyrimidin-5-yl)-1,8,10-triazatricyclo[7.4.0.0²,⁷]trideca-2(7),3,5,8,10,12-hexaene-11-carboxamide (50 mg, 0.16 mmol) and potassium carbonate (85 mg, 0.62 mmol) were suspended in NN-dimethylformamide (2 mL). Methyl iodide (200 µL, 10% solution in N,N-dimethylformamide) was added and the reaction mixture stirred at room temperature for 23 hours. The solvent was removed in vacuo and the residue triturated with water. Purification by FCC (silica, 0-100% 9:1 dichloromethane:methanol in dichloromethane) gave the title compound.

Example 1, Method 13: N-(1-Methyl-2-oxo-1,2-dihydropyrimidin-5-yl)-1,8,10-triazatricyclo[7.4.0.0²,⁷]trideca-2(7),3,5,8,10,12-hexaene-11-carboxamide ¹H NMR (500 MHz, DMSO) 11.09 (s, 1H), 9.78 (d, J=7.0 Hz, 1H), 8.92 (d, J=3.4 Hz, 1H), 8.74 (d, J=3.4 Hz, 1H), 8.43 (d, J=8.2 Hz, 1H), 7.96 (d, J=8.2 Hz, 1H), 7.74 (d, J=7.0 Hz, 1H), 7.68-7.61 (m, 1H), 7.58-7.49 (m, 1H), 3.50 (s, 3H). Tr(MET-uHPLC-AB-101)=1.4 min, m/z (ES⁺) (M+H)⁺ 321.

The following example was prepared using Method 13 described above:

TABLE 13

| Ex. | Structure | Mol. Weight | IUPAC Name | LCMS data |
|---|---|---|---|---|
| 1 | 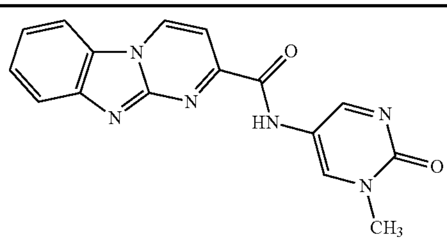 | 320.31 | N-(1-methyl-2-oxo-1,2-dihydropyrimidin-5-yl)-1,8,10-triazatricyclo[7.4.0.0$^{2,7}$]trideca-2(7),3,5,8,10,12-hexaene-11-carboxamide | Tr(MET-uHPLC-AB-101) = 1.4 min, m/z (ES$^+$) (M + H)$^+$ 321 |

Method 14

Scheme for Method 14

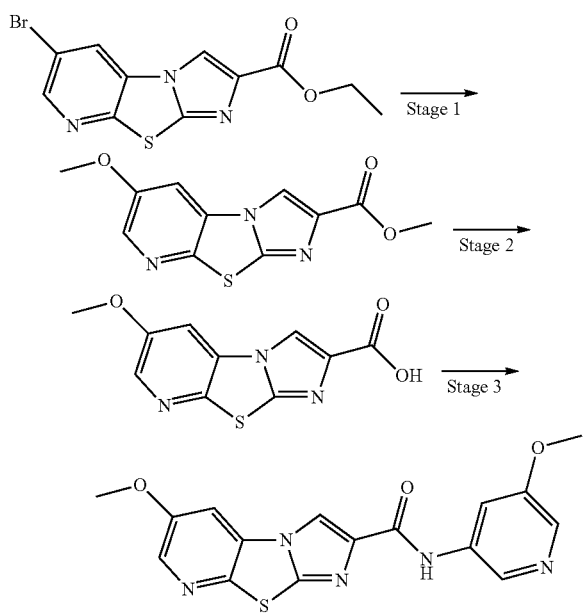

Step 1, Method 14: 11-Methoxy-7-thia-2,5,9-triazatricyclo[6.4.0.0$^{2,6}$]dodeca-1(12),3,5,8,10-pentaene-4-carboxylic acid Ethyl 11-bromo-7-thia-2,5,9-triazatricyclo[6.4.0.0$^{2,6}$]dodeca-1(12),3,5,8,10-pentaene-4-carboxylate (0.1 g, 0.31 mmol, prepared by Method 1), di-tert-butyl({3,6-dimethoxy-2-[2,4,6-tris(propan-2-yl)phenyl]phenyl})phosphane (3 mg, 0.01 mmol) and caesium carbonate (40 µL, 0.46 mmol) were added to a round bottomed flask and sealed. The flask was evacuated via a syringe needle to the vacuum line and purged with nitrogen. This process was repeated three times. Methanol (0.3 mL) was then added. In a separate flask was added methanesulfonato(2-(di-t-butylphosphino)-3,6-dimethoxy-2',4',6'-tri-i-propyl-1,1'-biphenyl)(2'-amino-1,1'-biphenyl-2-yl)palladium(II) (Strem Chemicals, Inc., cat number 46-0325) (5 mg, 0.01 mmol). The flask was sealed and evacuated via a syringe needle to the vacuum line and purged with nitrogen. This was repeated three times. Dioxane (2 mL) was added to the flask and the mixture stirred and degassed with nitrogen for 1 minute. This was transferred to the first flask via a cannula needle and heated to 50° C. for 24 hours. An additional portion of ligand was added to the reaction in tetrahydrofuran (2 mL) and heating continued at 50° C. overnight. An additional portion of ligand was added to the reaction in tetrahydrofuran (2 mL) and heating continued at 50° C. for 5 hours. The reaction was reduced to dryness then loaded directly onto silica and purified by FCC (0-100% ethyl acetate in heptane) to give the title compound. $^1$H NMR (500 MHz, DMSO) 9.08 (s, 1H), 8.36-8.37 (m, 2H), 3.95 (s, 3H), 3.85 (s, 3H). Tr(METCR1410)=0.91 min, m/z (ES$^+$) (M+1)$^+$ 264, 76%.

Step 2, Method 14: 11-Methoxy-7-thia-2,5,9-triazatricyclo[6.4.0.0$^{2,6}$]dodeca-1(12),3,5,8,10-pentaene-4-carboxylic acid Methyl 11-methoxy-7-thia-2,5,9-triazatricyclo[6.4.0.0$^{2,6}$]dodeca-1(12),3,5,8,10-pentaene-4-carboxylate (76%, 23 mg, 0.07 mmol) was suspended in tetrahydrofuran:water (4 mL:4 mL) and lithium hydroxide (8 mg, 0.33 mmol) added in one portion. The reaction was stirred at room temperature. The reaction was heated to 50° C. overnight. Potassium hydroxide (20 mg, 0.36 mmol) was added and stirring continued at 50° C. for 1 hour. The solution was allowed to cool and the tetrahydrofuran removed. The aqueous layer was slowly acidified to pH 1. Half the volume of water was removed under reduced pressure. The resultant precipitate was isolated by filtration and dried to give the title compound. $^1$H NMR (500 MHz, DMSO) 12.79 (br s, 1H), 9.01-8.86 (m, 1H), 8.34-8.35 (m, 2H), 3.95 (s, 3H). Tr(METCR1410)=0.86 min, m/z (ES$^+$) (M+H)$^+$ 250, 77%.

Step 3, Method 14: 11-Methoxy-N-(5-methoxypyridin-3-yl)-7-thia-2,5,9-triazatricyclo[6.4.0.0$^{2,6}$]dodeca-1(12),3,5,8,10-pentaene-4-carboxamide 11-Methoxy-7-thia-2,5,9-triazatricyclo[6.4.0.0$^{2,6}$]dodeca-1(12),3,5,8,10-pentaene-4-carboxylic acid (77%, 17 mg, 0.05 mmol) and 5-methoxypyridin-3-amine (7 mg, 0.05 mmol) were combined in pyridine (1 mL) and stirred for 10 minutes. N-(3-Dimethylaminopropyl)-N'-ethylcarbodiimide hydrochloride (10 mg, 0.06 mmol) was added in one portion and the reaction stirred overnight. The reaction was diluted with water then the solid isolated by filtration. The crude was purified by neutral prep-HPLC to give the title compound.

Example 1, Method 14: 11-Methoxy-N-(5-methoxypyridin-3-yl)-7-thia-2,5,9-triazatricyclo[6.4.0.0$^{2,6}$]dodeca-1(12),3,5,8,10-pentaene-4-carboxamide $^1$H NMR (500 MHz, DMSO) 10.49 (s, 1H), 9.02 (s, 1H), 8.73 (d, J=2.0 Hz, 1H), 8.40 (d, J=2.7 Hz, 1H), 8.36 (d, J=2.7

Hz, 1H), 8.05 (d, J=2.7 Hz, 1H), 7.99 (appt t, J=2.3 Hz, 1H), 3.96 (s, 3H), 3.84 (s, 3H). Tr(MET-uHPLC-AB-101)=2.16 min, m/z (ES⁺) (M+H)⁺ 356.

The following examples were prepared using Method 14 described above:

TABLE 14

| Ex. | Structure | Mol. Weight | IUPAC Name | LCMS data |
|---|---|---|---|---|
| 1 | 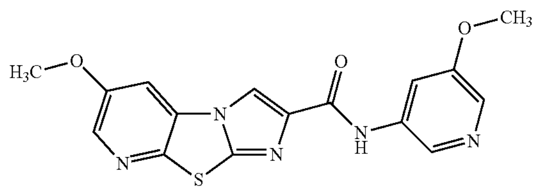 | 355.37 | 11-methoxy-N-(5-methoxypyridin-3-yl)-7-thia-2,5,9-triazatricyclo[6.4.0.0²,⁶]dodeca-1(12),3,5,8,10-pentaene-4-carboxamide | Tr(MET-uHPLC-AB-101) = 2.16 min, m/z (ES⁺) (M + H)⁺ 356 |
| 2 | 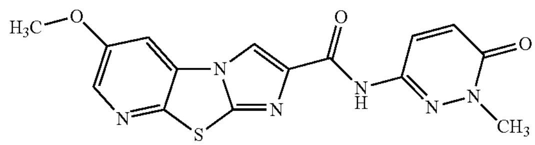 [SMILES: COc1cnc2sc3nc(C(=O)Nc4ccc(=O)n(C)n4)cn3c2c1] | 356.36 | 11-methoxy-N-(1-methyl-6-oxo-1,6-dihydropyridazin-3-yl)-7-thia-2,5,9-triazatricyclo[6.4.0.0²,⁶]dodeca-1(12),3,5,8,10-pentaene-4-carboxamide | Tr(MET-uHPLC-AB-101) = 2.29 min, m/z (ES⁺) (M + H)⁺ 357 |

Method 15

Scheme for Method 15

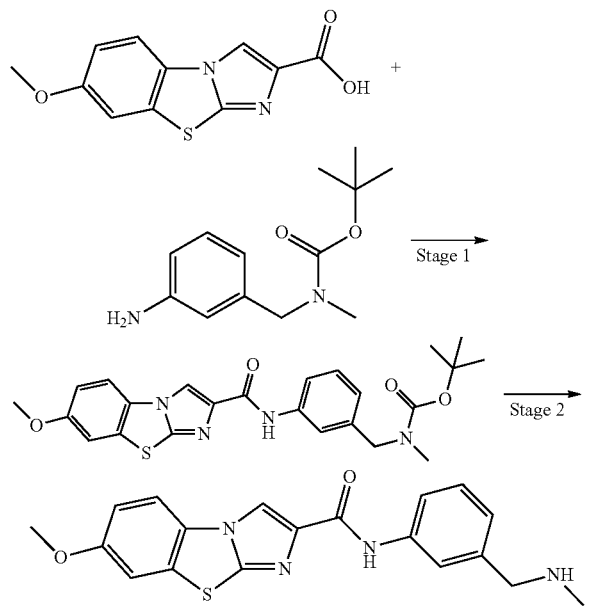

Step 1, Method 15: tert-Butyl N-[(3-{10-methoxy-7-thia-2,5-diazatricyclo[6.4.0.0²,⁶]dodeca-1(8),3,5,9,11-pentaene-4-amido}phenyl)methyl]-N-methylcarbamate 10-Methoxy-7-thia-2,5-diazatricyclo[6.4.0.0²,⁶]dodeca-1(8),3,5,9,11-pentaene-4-carboxylic acid (50 mg, 0.2 mmol, prepared by Method 1) and tert-butyl N-[(3-aminophenyl)methyl]-N-methylcarbamate (52 mg, 0.22 mmol) were dissolved in pyridine and stirred at room temperature for 5 minutes. N-(3-Dimethylaminopropyl)-N'-ethylcarbodiimide hydrochloride (42.47 mg, 0.22 mmol) was added and stirring continued at room temperature for 5 hours. Water (10 mL) was added to the reaction mixture and a precipitate formed which was collected by filtration and dried under vacuum to give the title compound. ¹H NMR (500 MHz, DMSO) 10.09 (s, 1H), 8.92 (s, 1H), 8.11 (d, J=8.9 Hz, 1H), 7.83 (d, J=50.1 Hz, 1H), 7.69-7.74 (m, 2H), 7.30 (appt t, J=7.8 Hz, 1H), 7.18 (dd, J=8.9, 2.5 Hz, 1H), 6.93 (d, J=6.9 Hz, 1H), 4.37 (s, 2H), 3.85 (s, 3H), 2.78 (s, 3H), 1.42 (s, 9H). Tr(METCR1410)=1.31 min, m/z (ES⁺) (M+H)⁺ 467.

Step 2, Method 15: 10-Methoxy-N-{3-[(methylamino)methyl]phenyl}-7-thia-2,5-diazatricyclo[6.4.0.0²,⁶]dodeca-1(8),3,5,9,11-pentaene-4-carboxamide Tert-butyl N-[(3-{10-methoxy-7-thia-2,5-diazatricyclo[6.4.0.0²,⁶]dodeca-1(8),3,5,9,11-pentaene-4-amido}phenyl)methyl]-N-methylcarbamate (59 mg, 0.15 mmol) was suspended in dichloromethane (2 mL), trifluoroacetic acid (1 mL) was added and the reaction mixture stirred at room temperature for 3 days. The reaction mixture was diluted with dichloromethane (25 mL) and water (25 mL). The layers were separated and the organic layer washed with saturated aqueous sodium carbonate solution, dried over magnesium sulphate, filtered and concentrated in vacuo to give the title compound.

Example 1, Method 15: 10-Methoxy-N-{3-[(methylamino)methyl]phenyl}-7-thia-2,5-diazatricyclo[6.4.0.0²,⁶]dodeca-1(8),3,5,9,11-pentaene-4-carboxamide ¹H NMR (500 MHz, DMSO) 10.01 (s, 1H), 8.91 (s, 1H), 8.11 (d, J=8.9 Hz, 1H), 7.88 (s, 1H), 7.74-7.66 (m, 2H), 7.29 (appt t, J=7.8 Hz, 1H), 7.18 (dd, J=8.9, 2.5 Hz, 1H), 7.07 (d, J=7.6 Hz, 1H), 3.85 (s, 3H), 3.71 (s, 2H), 2.33 (s, 3H). Tr(MET-uHPLC-AB-101)=1.91 min, m/z (ES⁺) (M+H)⁺ 367.

The following example was prepared using Method 15 described above:

TABLE 15

| Ex. | Structure | Mol. Weight | IUPAC Name | LCMS data |
|---|---|---|---|---|
| 1 | (structure shown) | 366.44 | 10-methoxy-N-{3-[(methylamino)methyl]phenyl}-7-thia-2,5-diazatricyclo[6.4.0.0²,⁶]dodeca-1(8),3,5,9,11-pentaene-4-carboxamide | Tr(MET-uHPLC-AB-101) = 1.91 min, m/z (ES⁺) (M + H)⁺ 367 |

Method 16

Scheme for Method 16

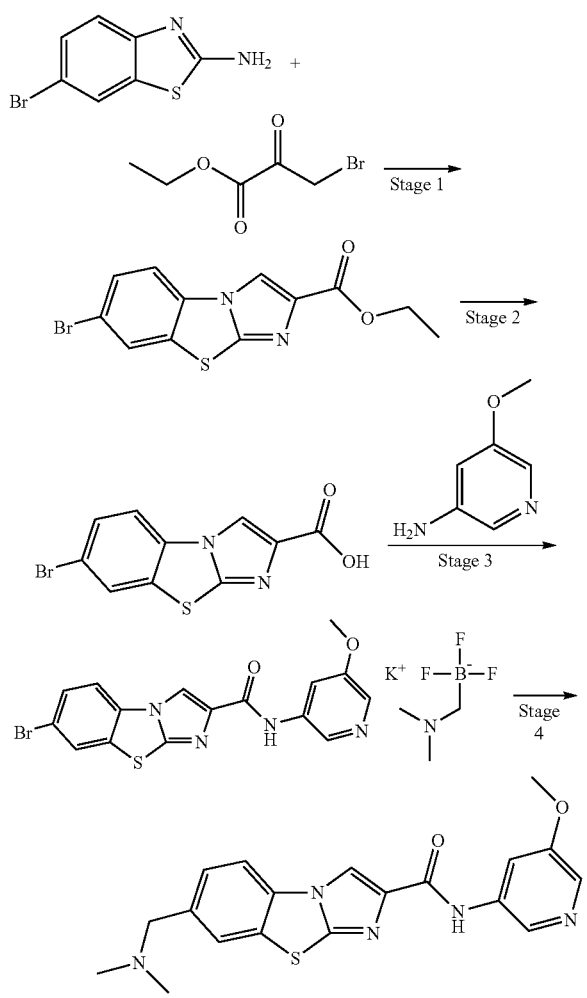

Step 1, Method 16: Ethyl 10-bromo-7-thia-2,5-diazatricyclo[6.4.0.0²,⁶]dodeca-1(12),3,5,8,10-pentaene-4-carboxylate Ethyl 3-bromo-2-oxopropanoate (1.2 ml, 9.6 mmol) was added dropwise to a stirred solution of 6-bromo-1,3-benzothiazol-2-amine (2 g, 8.73 mmol) in N,N-dimethylacetamide (50 mL) at room temperature. The reaction mixture was heated to 100° C. for 18 hours. The reaction mixture was cooled to room temperature and water was added and the mixture filtered. The collected solid was dried under vacuum for 2 hours to give the title compound. $^1$H NMR (500 MHz, DMSO) 9.04 (s, 1H), 8.36 (d, J=1.9 Hz, 1H), 8.13 (d, J=8.6 Hz, 1H), 7.77 (dd, J=8.6, 2.0 Hz, 1H), 4.30 (q, J=7.1 Hz, 2H), 1.31 (t, J=7.1 Hz, 3H); Tr(METCR1410)=1.14 min, m/z (ES⁺) (M+H)⁺ 325/327, 81%.

Step 2, Method 16: 10-Bromo-7-thia-2,5-diazatricyclo[6.4.0.0²,⁶]dodeca-1(12),3,5,8,10-pentaene-4-carboxylic acid Ethyl 10-bromo-7-thia-2,5-diazatricyclo[6.4.0.0²,⁶]dodeca-1(12),3,5,8,10-pentaene-4-carboxylate (81%, 2.03 g, 5.06 mmol) was suspended in 1:1 tetrahydrofuran/water (50 mL), lithium hydroxide (242 mg, 10.11 mmol) was added and the reaction mixture stirred at room temperature for 18 hours. The reaction mixture was acidifed with 2 M hydrochloric acid until a precipitate formed which was collected by filtration. The collected solid was dried under vacuum to give the title compound. $^1$H NMR (500 MHz, DMSO) 8.97 (s, 1H), 8.36 (d, J=1.9 Hz, 1H), 8.11 (d, J=8.6 Hz, 1H), 7.77 (dd, J=8.6, 2.0 Hz, 1H); Tr(METCR1410)=0.98 min, m/z (ES⁺) (M+H)⁺ 297/299.

Step 3, Method 16: 10-Bromo-N-(5-methoxypyridin-3-yl)-7-thia-2,5-diazatricyclo[6.4.0.0²,⁶]dodeca-1(12),3,5,8,10-pentaene-4-carboxamide 10-Bromo-7-thia-2,5-diazatricyclo[6.4.0.0²,⁶]dodeca-1(12),3,5,8,10-pentaene-4-carboxylic acid (1.5 g, 5.05 mmol) and 5-methoxypyridin-3-amine (752 mg, 6.06 mmol) were suspended in pyridine (20 mL) and the mixture stirred at room temperature for 10 minutes. N-(3-Dimethylaminopropyl)-N'-ethylcarbodiimide hydrochloride (1.16 g, 6.06 mmol) was added and the reaction mixture stirred at room temperature for 4 days. Water (15 mL) was added and the precipitate collected by filtration and dried under vacuum for 3 hours to give the title compound. $^1$H NMR (500 MHz, DMSO) 10.43 (s, 1H), 9.03 (s, 1H), 8.71 (d, J=2.0 Hz, 1H), 8.39 (d, J=1.9 Hz, 1H), 8.16 (d, J=8.6 Hz, 1H), 8.04 (d, J=2.6 Hz, 1H), 7.97 (appt t, J=2.3 Hz, 1H), 7.80 (dd, J=8.6, 2.0 Hz, 1H), 3.83 (s, 3H); Tr(METCR1410)=1.11 min, m/z (ES⁺) (M+H)⁺ 403/405.

Step 4, Method 16: 10-[(Dimethylamino)methyl]-N-(5-methoxypyridin-3-yl)-7-thia-2,5-diazatricyclo[6.4.0.0$^{2,6}$]dodeca-1(12),3,5,8,10-pentaene-4-carboxamide 10-Bromo-N-(5-methoxypyridin-3-yl)-7-thia-2,5-diazatricyclo[6.4.0.0$^{2,6}$]dodeca-1(12),3,5,8,10-pentaene-4-carboxamide (350 mg, 0.87 mmol) in dioxane (18 mL) was added to a solution of potassium Rdimethylamino)methyl-ltrifluoroborate (186 mg, 1.13 mmol) in water (4 mL), followed by the addition of palladium(II) acetate (39 mg, 0.17 mmol), SPhos (2-Dicyclohexylphosphino-2',6'-dimethoxybiphenyl, 143 mg, 0.35 mmol) and potassium phosphate (1474 mg, 6.94 mmol). The resulting mixture was stirred at 115° C. for 22 hours under a flow of nitrogen. The solvents were removed in vacuo. Purification by FCC (silica, 0-100% 9:1 dichloromethane/methanol in dichloromethane) gave the title compound.

Example 1, Method 16: 10-[(Dimethylamino)methyl]-N-(5-methoxypyridin-3-yl)-7-thia-2,5-diazatricyclo[6.4.0.0$^{2,6}$]dodeca-1(12),3,5,8,10-pentaene-4-carboxamide $^1$H NMR (500 MHz, DMSO) 10.43 (s, 1H), 9.00 (s, 1H), 8.73 (d, J=2.0 Hz, 1H), 8.15 (d, J=8.3 Hz, 1H), 8.05 (d, J=2.6 Hz, 1H), 8.00 (s, 1H), 7.99 (appt t, J=2.3 Hz, 1H), 7.51 (dd, J=8.3, 1.3 Hz, 1H), 3.84 (s, 3H), 3.52 (s, 2H), 2.19 (s, 6H). Tr(METCR1600)=4.13 min, m/z (ES$^+$) (M+H)$^+$ 382.

The following examples were prepared using Method 16 described above:

Method 17

Scheme for Method 17

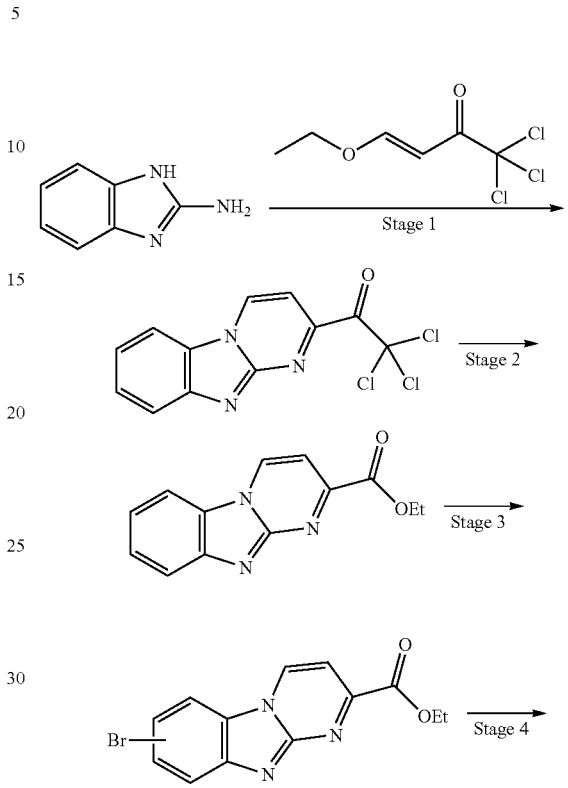

TABLE 16

| Ex. | Structure | Mol. Weight | IUPAC Name | LCMS data |
|---|---|---|---|---|
| 1 | 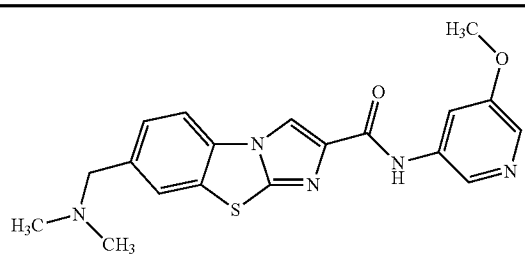 | 381.45 | 10-[(dimethylamino)methyl]-N-(5-methoxypyridin-3-yl)-7-thia-2,5-diazatricyclo[6.4.0.0$^{2,6}$]dodeca-1(12),3,5,8,10-pentaene-4-carboxamide | Tr(METCR1600) = 4.13 min, m/z (ES$^+$) (M + H)$^+$ 382 |
| 2 | 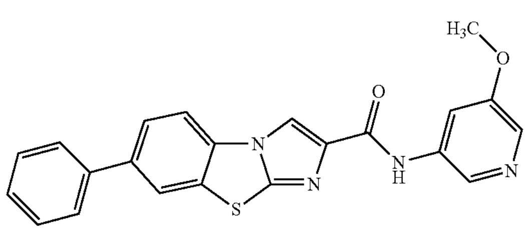 [SMILES: COc1cncc(NC(=O)c2cn3c(n2)sc2cc(-c4ccccc4)ccc23)c1] | 400.46 | N-(5-methoxypyridin-3-yl)-10-phenyl-7-thia-2,5-diazatricyclo[6.4.0.0$^{2,6}$]dodeca-1(12),3,5,8,10-pentaene-4-carboxamide | Tr(MET-uHPLC-AB-101) = 3.34 min, m/z (ES$^+$) (M + H)$^+$ 401 |

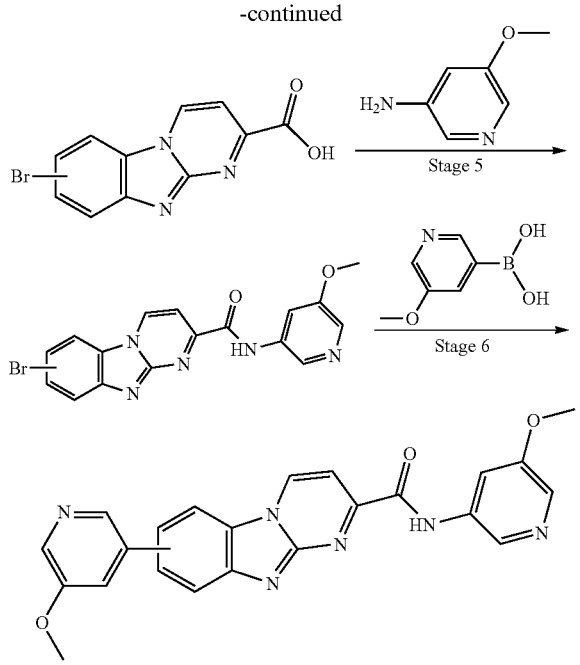

Step 1, Method 17: 11-(Trichloromethyl)-1,8,10-triazatricyclo[7.4.0.0²,⁷]trideca-2(7),3,5,8,10,12-hexaene 1H-1,3-Benzodiazol-2-amine (4 g, 30 mmol) and (3E)-1,1,1-trichloro-4-ethoxybut-3-en-2-one (6.53 g, 30 mmol) were suspended in anhydrous toluene (60 mL). Triethylamine (4.2 mL, 30 mmol) was added and the reaction was heated to 120° C. for 2.5 hours. The reaction mixture was cooled to room temperature and the solvents removed in vacuo. Water was added, and the residue sonicated and filtered. The crude material was dissolved in dichloromethane (500 mL) and washed with 2 M sodium hydroxide (300 mL), the organic layer was concentrated in vacuo to give the title compound. $^1$H NMR (500 MHz, DMSO) 9.78 (d, J=7.3 Hz, 1H), 8.42 (d, J=8.2 Hz, 1H), 7.95 (d, J=8.2 Hz, 1H), 7.76 (d, J=7.2 Hz, 1H), 7.63 (appt t, J=7.7 Hz, 1H), 7.56-7.50 (m, 1H). Tr(METCR1410)=1.09 min, m/z (ES$^+$) (M+H)$^+$ 286/288, 80%.

Step 2, Method 17: Ethyl 1,8,10-triazatricyclo[7.4.0.0²,⁷]trideca-2(7),3,5,8,10,12-hexaene-11-carboxylate 11-(Trichloromethyl)-1,8,10-triazatricyclo[7.4.0.0²,⁷]trideca-2(7),3,5,8,10,12-hexaene (5.43 g, 19 mmol) was suspended in sulphuric acid (45 mL) and heated to 140° C. for 1 hour. The reaction mixture was cooled to room temperature and ethanol (250 mL) was added. The reaction was heated to 80° C. overnight. The reaction mixture was cooled to room temperature and ethanol (100 mL) was added. The reaction mixture was stirred at 80° C. overnight. The reaction mixture was cooled to room temperature, the ethanol removed in vacuo and the acidic residue was basified by addition of solid sodium hydrogen carbonate. The basic layer was diluted with water (500 mL) and extracted with dichloromethane (3×1 L). The combined organics were dried over anhydrous magnesium sulphate, filtered and the filtrate concentrated in vacuo to give the title compound. $^1$H NMR (500 MHz, DMSO) 9.74 (d, J=7.0 Hz, 1H), 8.43 (d, J=8.2 Hz, 1H), 7.97 (d, J=8.3 Hz, 1H), 7.67-7.62 (m, 2H), 7.55-7.50 (m, 1H), 4.45 (q, J=7.1 Hz, 2H), 1.41 (t, J=7.1 Hz, 3H). Tr(METCR1410)=0.87 min, m/z (ES$^+$) (M+H)$^+$ 242.

Step 3, Method 17: Ethyl 4-bromo-1,8,10-triazatricyclo[7.4.0.0²,⁷]trideca-2(7),3,5,8,10,12-hexaene-11-carboxylate and ethyl 5-bromo-1,8,10-triazatricyclo[7.4.0.0²,⁷]trideca-2(7),3,5,8,10,12-hexaene-11-carboxylate Ethyl 1,8,10-triazatricyclo[7.4.0.0²,⁷]trideca-2(7),3,5,8,10,12-hexaene-11-carboxylate (3.99 g, 17.0 mmol) was dissolved in dichloromethane (200 mL), N-bromosuccinimide (7.35 g, 41.3 mmol) added and the reaction stirred at room temperature overnight. The reaction mixture was diluted in further dichloromethane (300 ml) and N-bromosuccinimide (7.35 g, 41.3 mmol) added. The reaction was stirred at room temperature for 3 hours. The reaction mixture was retreated with N-bromosuccinimide (14.7 g, 82.59 mmol) and the reaction mixture stirred at room temperature for 5 days. The reaction mixture was diluted with dichloromethane (1 L) and the organic was washed with 1 M sodium hydroxide (800 mL). The organics were dried over magnesium sulfate, filtered and the filtrate concentrated in vacuo to give the title compound mixture. $^1$H NMR (500 MHz, DMSO) 9.70 (d, J=7.0 Hz, 1H), 8.78 (d, J=1.9 Hz, 1H), 7.91 (d, J=8.8 Hz, 1H), 7.75 (dd, J=8.8, 2.0 Hz, 1H), 7.67 (d, J=7.0 Hz, 1H), 4.44 (q, J=7.1 Hz, 2H), 1.41-1.38 (m, 3H). Tr(METCR1410)= 1.03 min, m/z (ES$^+$) (M+H)$^+$ 320/322, 90%.

Step 4, Method 17: 4-Bromo-1,8,10-triazatricyclo[7.4.0.0²,⁷]trideca-2(7),3,5,8,10,12-hexaene-11-carboxylic acid and 5-bromo-1,8,10-triazatricyclo[7.4.0.0²,⁷]trideca-2(7),3,5,8,10,12-hexaene-11-carboxylic acid A mixture of ethyl 4-bromo-1,8,10-triazatricyclo[7.4.0.0²,⁷]trideca-2(7),3,5,8,10,12-hexaene-11-carboxylate and ethyl 5-bromo-1,8,10-triazatricyclo[7.4.0.0²,⁷]trideca-2(7),3,5,8,10,12-hexaene-11-carboxylate (1000 mg, 3.12 mmol) was suspended in methanol (50 mL), potassium carbonate (432 mg, 3.12 mmol) added and the reaction stirred at room temperature for 2 days. The reaction mixture was retreated with potassium carbonate (432 mg, 3.12 mmol) and a few drops of water added. The reaction mixture was stirred at room temperature overnight. The solvents were removed in vacuo, the residue acidified with 2 M hydrochloric acid (15 mL) and filtered. The precipitate was concentrated from methanol (30 mL) to afford the title compound mixture. $^1$H NMR (500 MHz, DMSO) 9.77 (d, J=7.0 Hz, 1H), 8.83 (d, J=1.8 Hz, 1H), 7.92 (d, J=8.8 Hz, 1H), 7.80 (dd, J=8.8, 1.9 Hz, 1H), 7.78 (d, J=7.0 Hz, 1H). Tr(METCR1410)=0.80 min, m/z (ES$^+$) (M+H)$^+$ 292/294.

Step 5, Method 17: 4-Bromo-N-(5-methoxypyridin-3-yl)-1,8,10-triazatricyclo[7.4.0.0²,⁷]trideca-2(7),3,5,8,10,12-hexaene-11-carboxamide and 5-bromo-N-(5-methoxypyridin-3-yl)-1,8,10-triazatricyclo[7.4.0.0²,⁷]trideca-2(7),3,5,8,10,12-hexaene-11-carboxamide A mixture of 4-bromo-1,8,10-triazatricyclo[7.4.0.0²,⁷]trideca-2(7),3,5,8,10,12-hexaene-11-carboxylic acid and 5-bromo-1,8,10-triazatricyclo[7.4.0.0²,⁷]trideca-2(7),3,5,8,10,12-hexaene-11-carboxylic acid (285 mg, 0.98 mmol), 1-[bis(dimethylamino)methylene]-1H-1,2,3-triazolo[4,5-b]

pyridinium 3-oxide hexafluorophosphate (408 mg, 1.07 mmol) and ethyldiisopropylamine (0.4 mL, 2.15 mmol) were dissolved in anhydrous N,N-dimethylformamide (5 mL) and stirred at room temperature for 30 minutes. 5-Methoxypyridin-3-amine (133 mg, 1.07 mmol) was added and the reaction stirred at room temperature for 16 hours. The reaction mixture was retreated with 1-[bis(dimethylamino)methylene]-1H-1,2,3-triazolo[4,5-b]pyridinium 3-oxide hexafluorophosphate (408 mg, 1.07 mmol), ethyldiisopropylamine (0.4 mL, 2.15 mmol) and N,N-dimethylformamide (2 mL) and stirred at room temperature for 72 hours. Water was added to the reaction mixture and it was filtered to give the title compound mixture. $^1$H NMR (500 MHz, DMSO) 11.19 (s, 1H), 9.81-9.73 (m, 1H), 8.81 (d, J=2.0 Hz, 1H), 8.12 (d, J=2.6 Hz, 1H), 8.04-8.00 (m, 1H), 7.97-7.90 (m, 2H), 7.84-7.78 (m, 1H), 7.77-7.74 (m, 1H), 3.86 (s, 3H). Tr(METCR1410)=1.02 min, m/z (ES$^+$) (M+H)$^+$ 398/400, 85%.

Step 6, Method 17: N,5-Bis(5-methoxypyridin-3-yl)-1,8,10-triazatricyclo[7.4.0.0$^{2,7}$]trideca-2(7),3,5,8,10,12-hexaene-11-carboxamide and N,4-Bis(5-methoxypyridin-3-yl)-1,8,10-triazatricyclo[7.4.0.0$^{2,7}$]trideca-2(7),3,5,8,10,12-hexaene-11-carboxamide A mixture of 4-bromo-N-(5-methoxypyridin-3-yl)-1,8,10-triazatricyclo[7.4.0.0$^{2,7}$]trideca-2(7),3,5,8,10,12-hexaene-11-carboxamide and 5-bromo-N-(5-methoxypyridin-3-yl)-1,8,10-triazatricyclo[7.4.0.0$^{2,7}$]trideca-2(7),3,5,8,10,12-hexaene-11-carboxamide (85%, 246 mg, 0.53 mmol), (5-methoxypyridin-3-yl)boronic acid (88 mg, 0.58 mmol), RuPhos (2-Dicyclohexylphosphino-2',6'-diisopropoxybiphenyl, 49 mg, 0.11 mmol) and tripotassium phosphate (223 mg, 1.05 mmol) in dioxane/water (2 mL/1 mL) was purged with nitrogen gas and palladium(II) acetate (12 mg, 0.05 mmol) added. The reaction was irradiated under microwave conditions at 140° C. for 3 hours. The reaction mixture was diluted with water and filtered. The precipitate was dissolved in dimethylsulfoxide and a few drops of water were added to initiate precipitation. The mixture was filtered and dried. The resulting solid was purified by acidic HPLC to give N,5-bis(5-methoxypyridin-3-yl)-1,8,10-triazatricyclo[7.4.0.0$^{2,7}$]trideca-2(7),3,5,8,10,12-hexaene-11-carboxamide and N,4-bis(5-methoxypyridin-3-yl)-1,8,10-triazatricyclo[7.4.0.0$^{2,7}$]trideca-2(7),3,5,8,10,12-hexaene-11-carboxamide. The isomers were separate according to methods known in the art.

Example 1, Method 17: N,5-Bis(5-methoxypyridin-3-yl)-1,8,10-triazatricyclo[7.4.0.0$^{2,7}$]trideca-2(7),3,5,8,10,12-hexaene-11-carboxamide $^1$H NMR (500 MHz, DMSO) 11.21 (s, 1H), 9.84 (d, J=7.0 Hz, 1H), 8.83 (d, J=2.0 Hz, 1H), 8.65 (d, J=1.8 Hz, 1H), 8.56 (d, J=8.6 Hz, 1H), 8.35 (d, J=1.3 Hz, 1H), 8.33 (d, J=2.7 Hz, 1H), 8.12 (d, J=2.6 Hz, 1H), 8.06-8.04 (m, 1H), 7.94 (dd, J=8.6, 1.7 Hz, 1H), 7.84-7.80 (m, 2H), 3.96 (s, 3H), 3.87 (s, 3H). Tr(METCR1603)=3.61 min, m/z (ES$^+$) (M+H)$^+$ 427, 92%.

Example 2, Method 17: N,4-bis(5-methoxypyridin-3-yl)-1,8,10-triazatricyclo[7.4.0.0$^{2,7}$]trideca-2(7),3,5,8,10,12-hexaene-11-carboxamide $^1$H NMR (500 MHz, DMSO) 9.83 (d, J=7.0 Hz, 1H), 8.94 (s, 1H), 8.83 (d, J=2.0 Hz, 1H), 8.69 (d, J=1.8 Hz, 1H), 8.33 (d, J=2.7 Hz, 1H), 8.13 (d, J=2.6 Hz, 1H), 8.05 (m, 3H), 7.85 (d, J=7.0 Hz, 1H), 7.80 (m, 1H), 3.97 (s, 3H), 3.87 (s, 3H).

The following examples were prepared using Method 17 described above:

TABLE 17

| Ex. | Structure | Mol. Weight | IUPAC Name | LCMS data |
| --- | --- | --- | --- | --- |
| 1 | 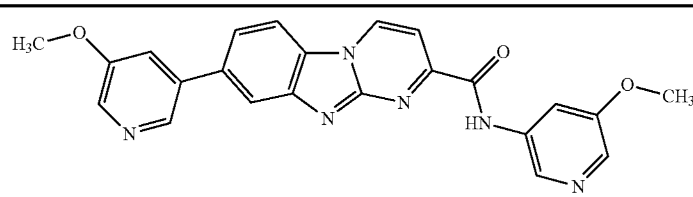 | 426.44 | N,5-bis(5-methoxypyridin-3-yl)-1,8,10-triazatricyclo[7.4.0.0$^{2,7}$]trideca-2(7),3,5,8,10,12-hexaene-11-carboxamide | Tr(METCR 1603) = 3.61 min, m/z (ES$^+$) (M + H)$^+$ 427 |
| 2 | 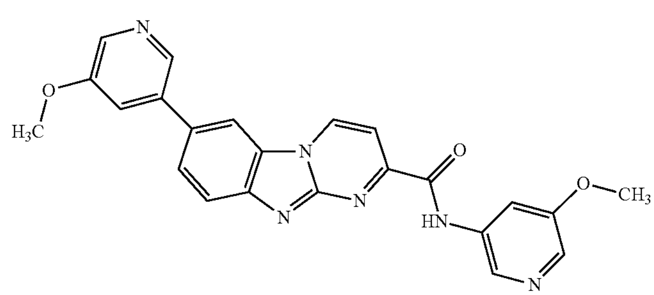 | 426.44 | N,4-bis(5-methoxypyridin-3-yl)-1,8,10-triazatricyclo[7.4.0.0$^{2,7}$]trideca-2(7),3,5,8,10,12-hexaene-11-carboxamide | Tr(METCR 1603) = 3.63 min, m/z (ES$^+$) (M + H)$^+$ 427 |

Method 18

Scheme for Method 18

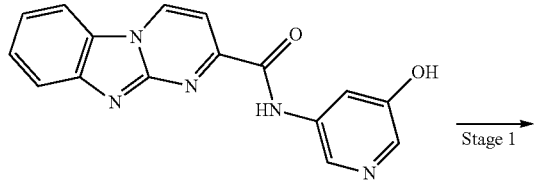

Step 1, Method 18: N-[5-(2-Methoxyethoxy)pyridin-3-yl]-1,8,10-triazatricyclo[7.4.0.0$^{2,7}$]trideca-2(7),3,5,8,10,12-hexaene-11-carboxamide N-(5-Hydroxypyridin-3-yl)-1,8,10-triazatricyclo[7.4.0.0$^{2,7}$]trideca-2(7),3,5,8,10,12-hexaene-11-carboxamide (35 mg, 0.11 mmol, prepared by Method 3) was suspended in N,N-dimethylformamide (2 mL) and sodium hydride (3 mg, 0.11 mmol) added in one portion. The reaction was stirred for 15 minutes then 1-chloro-2-methoxyethane added and the reaction stirred at 50° C. for 3 days. Water (0.5 mL) was added and the reaction concentrated. The crude product was purified by high pH preparative HPLC to give the title compound.

Example 1, Method 18: N-[5-(2-Methoxyethoxy)pyridin-3-yl]-1,8,10-triazatricyclo[7.4.0.0$^{2,7}$]trideca-2(7),3,5,8,10,12-hexaene-11-carboxamide $^1$H NMR (500 MHz, DMSO) 11.18 (s, 1H), 9.80 (d, J=7.0 Hz, 1H), 8.83 (s, 1H), 8.45 (d, J=8.2 Hz, 1H), 8.13 (s, 1H), 8.04 (d, J=2.3 Hz, 1H), 7.98 (d, J=8.3 Hz, 1H), 7.79 (d, J=7.0 Hz, 1H), 7.66 (appt t, J=7.7 Hz, 1H), 7.54 (appt t, J=7.7 Hz, 1H), 4.25-4.17 (m, 2H), 3.75-3.69 (m, 2H), 3.34 (s, 3H). Tr(MET-uHPLC-AB-101)=1.89 min, m/z (ES$^+$) (M+H)$^+$ 364.

The following example was prepared using Method 18 described above:

TABLE 18

| Ex. | Structure | Mol. Weight | IUPAC Name | LCMS data |
|---|---|---|---|---|
| 1 | 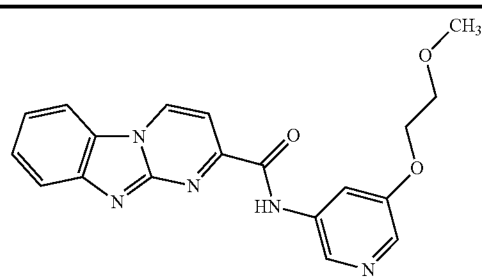 | 363.38 | N-[5-(2-methoxyethoxy)pyridin-3-yl]-1,8,10-triazatricyclo[7.4.0.0$^{2,7}$]trideca-2(7),3,5,8,10,12-hexaene-11-carboxamide | Tr(MET-uHPLC-AB-101) = 1.89 min, m/z (ES$^+$) (M + H)$^+$ 364 |

Method 19

Scheme for Method 19

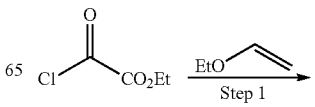

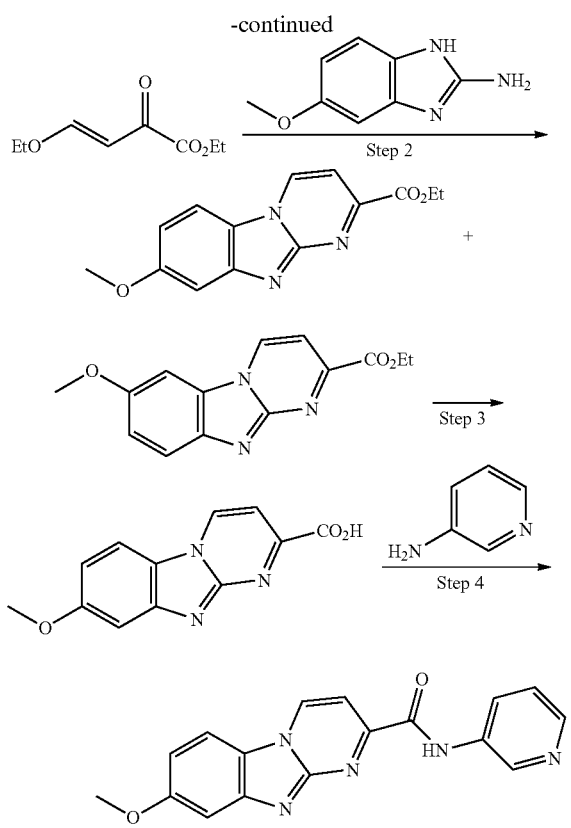

Step 1, Method 19: (E)-Ethyl 4-ethoxy-2-oxobut-3-enoate

Pyridine (8 mL, 7.8 g, 98.9 mmol) was added drop-wise over 2 minutes to a solution of ethyl 2-chloro-2-oxoacetate (11 mL, 98.5 mmol) in dichloromethane (135 mL) cooled in an ice-water bath. Ethyl vinyl ether (9.5 mL, 7.2 g, 99.2 mmol) was then added dropwise over 5 minutes, the resulting mixture was stirred with ice bath cooling for 30 minutes and warmed to room temperature. Water (100 mL) was added, the layers were separated and the organic layer washed with saturated sodium bicarbonate solution (100 mL) and brine (100 mL), dried over sodium sulfate, filtered and concentrated in vacuo to give the title compound. $^1$H NMR (500 MHz, CDCl$_3$) 7.87 (d, J=12.5 Hz, 1H), 6.19 (d, J=12.5 Hz, 1H), 4.33 (q, J=7.5 Hz, 2H), 4.07 (q, J=7.0 Hz, 2H), 1.29-1.42 (m, 6H).

Step 2, Method 19: Ethyl 8-methoxybenzo[4,5]imidazo[1,2-a]pyrimidine-2-carboxylate A mixture of 5-methoxy-1H-benzo[d]imidazol-2-amine (5.6 g, 34.3 mmol), (E)-ethyl 4-ethoxy-2-oxobut-3-enoate (5.9 g, 34.5 mmol) and triethylamine (4.8 mL, 3.5 g, 34.7 mmol) in toluene (115 mL) was heated at 80° C. for 18 hours. The mixture was cooled to room temperature. The volatiles were removed in vacuo and the residue obtained was adsorbed onto silica gel and purified by FCC (silica, dichloromethane to 95:5 dichloromethane/methanol) to give a 66:34 mixture of 8-methoxy and 7-methoxy regioisomers. The product was suspended in acetonitrile (550 mL), heated at 100° C. for 2.5 hours and then cooled to room temperature and left overnight. The solid product was isolated by filtration and dried to give an 81:19 mixture of 8-methoxy:7-methoxy. Hot trituration from acetonitrile was repeated once with 450 mL of solvent and three times with 35-40 mL of solvent to give the title compound. $^1$H NMR (500 MHz, DMSO) 9.65 (d, J=6.5 Hz, 1H), 8.31 (d, J=9.0 Hz, 1H), 7.63 (d, J=7.0 Hz, 1H), 7.42, (d, J=2.0 Hz, 1H), 7.13 (dd, J=9.0, 2.5 Hz, 1H), 4.43 (q, J=7.5 Hz, 2H), 3.90 (s, 3H), 1.40 (t, J=7.5 Hz, 3H).

Step 3, Method 19: 5-Methoxy-1,8,10-triazatricyclo[7.4.0.0$^{2,7}$]trideca-2,4,6,8,10,12-hexaene-11-carboxylic acid A suspension of ethyl 8-methoxybenzo[4,5]imidazo[1,2-a]pyrimidine-2-carboxylate (3.1 g, 11.4 mmol) in 6 N hydrochloric acid (140 mL) was heated at 95° C. for 4 hours. After this time the mixture was allowed to cool to room temperature. The resulting yellow precipitate was collected by filtration, dissolved in saturated sodium bicarbonate solution (100 mL) and the solution extracted with ethyl acetate (8×200 mL). The pH of the aqueous layer was adjusted to 1 by addition of 1 N hydrochloric acid and the precipitated product collected by filtration and dried at reduced pressure to give the title compound. mp 270-273° C., dec; $^1$H NMR (500 MHz, DMSO) 13.85 (br s, 1H), 9.63 (d, J=7.0 Hz, 1H), 8.30 (d, J=9.0 Hz, 1H), 7.62 (d, J=7.0 Hz, 1H), 7.41 (d, J=2.0 Hz, 1H), 7.12 (dd, J=9.0, 2.5 Hz, 1H), 3.90 (s, 3H).

Step 4, Method 19: 5-Methoxy-N-(pyridin-3-yl)-1,8,10-triazatricyclo[7.4.0.0$^{2,7}$]trideca-2(7),3,5,8,10,12-hexaene-11-carboxamide 5-Methoxy-1,8,10-triazatricyclo[7.4.0.0$^{2,7}$]trideca-2,4,6,8,10,12-hexaene-11-carboxylic acid (95%, 50 mg, 0.2 mmol) and pyridin-3-amine (21 mg, 0.21 mmol) were suspended in anhydrous N,N-dimethylformamide (3 ml). Ethyldiisopropylamine (0.1 ml, 0.58 mmol) and 1-[bis(dimethylamino)methylene]-1H-1,2,3-triazolo[4,5-b]pyridinium 3-oxide hexafluorophosphate (90 mg, 0.24 mmol) were added and the reaction stirred at room temperature for 16 hours. The reaction mixture was concentrated in vacuo and water (20 mL) added. The mixture was filtered through glass fibre filter paper and the precipitate purified by FCC (silica, 0-7% methanol in dichloromethane) to give the title compound.

Example 1, Method 19: 5-Methoxy-N-(pyridin-3-yl)-1,8,10-triazatricyclo[7.4.0.0$^{2,7}$]trideca-2(7),3,5,8,10,12-hexaene-11-carboxamide $^1$H NMR (500 MHz, DMSO) 11.17 (s, 1H), 9.71 (d, J=6.9 Hz, 1H), 9.13 (d, J=2.3 Hz, 1H), 8.39-8.34 (m, 2H), 8.32 (d, J=9.0 Hz, 1H), 7.77 (d, J=6.9 Hz, 1H), 7.45 (dd, J=8.3, 4.7 Hz, 1H), 7.41 (d, J=2.3 Hz, 1H), 7.14 (dd, J=9.0, 2.4 Hz, 1H), 3.91 (s, 3H). Tr(METCR1600)=3.33 min, m/z (ES$^+$) (M+H)$^+$ 320.

The following examples were prepared using Method 19 described above:

TABLE 19

| Ex. | Structure | Mol. Weight | IUPAC Name | LCMS data |
|---|---|---|---|---|
| 1 | 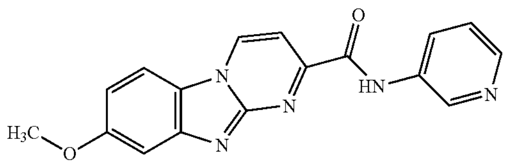 [SMILES: COc1ccc2c(c1)nc1nc(C(=O)Nc3cccnc3)ccn12] | 319.32 | 5-methoxy-N-(pyridin-3-yl)-1,8,10-triazatricyclo[7.4.0.0$^{2,7}$]trideca-2(7),3,5,8,10,12-hexaene-11-carboxamide | Tr(MET-uHPLC-AB-101) = 1.48 min, m/z (ES$^+$) (M + H)$^+$ 320 |
| 2 | 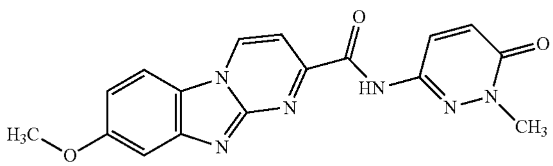 [SMILES: COc1ccc2c(c1)nc1nc(C(=O)Nc3ccc(=O)n(C)n3)ccn12] | 350.34 | 5-methoxy-N-(1-methyl-6-oxo-1,6-dihydropyridazin-3-yl)-1,8,10-triazatricyclo[7.4.0.0$^{2,7}$]trideca-2(7),3,5,8,10,12-hexaene-11-carboxamide | Tr(METCR1600) = 3.39 min, m/z (ES$^+$) (M + H)$^+$ 351 |
| 3 | 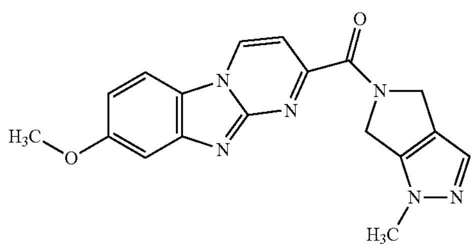 [SMILES: COc1ccc2c(c1)nc1nc(C(=O)N3Cc4cnn(C)c4C3)ccn12] | 348.37 | 5-methoxy-11-{1-methyl-1H,4H,5H,6H-pyrrolo[3,4-c]pyrazole-5-carbonyl}-1,8,10-triazatricyclo[7.4.0.0$^{2,7}$]trideca-2(7),3,5,8,10,12-hexaene | Tr(MET-uHPLC-AB-101) = 1.64 min, m/z (ES$^+$) (M + H)$^+$ 349 |
| 4 | 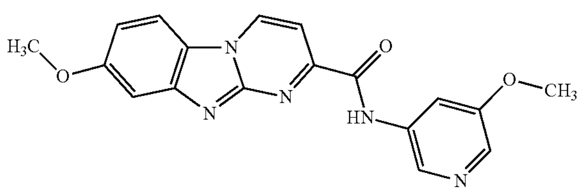 | 349.35 | 5-methoxy-N-(5-methoxypyridin-3-yl)-1,8,10-triazatricyclo[7.4.0.0$^{2,7}$]trideca-2(7),3,5,8,10,12-hexaene-11-carboxamide | Tr(MET-uHPLC-AB-101) = 1.91 min, m/z (ES$^+$) (M + H)$^+$ 350.1 |
| 5 | 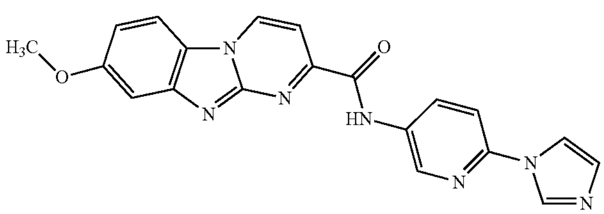 [SMILES: COc1ccc2c(c1)nc1nc(C(=O)Nc3ccc(-n4ccnc4)nc3)ccn12] | 385.39 | N-[6-(1H-imidazol-1-yl)pyridin-3-yl]-5-methoxy-1,8,10-triazatricyclo[7.4.0.0$^{2,7}$]trideca-2(7),3,5,8,10,12-hexaene-11-carboxamide | Tr(MET-uHPLC-AB-101) = 1.57 min, m/z (ES$^+$) (M + H)$^+$ 386 |
| 6 | 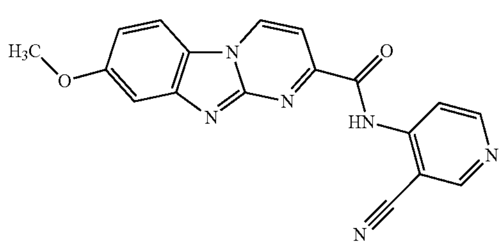 [SMILES: COc1ccc2c(c1)nc1nc(C(=O)Nc3ccncc3C#N)ccn12] | 344.33 | N-(3-cyanopyridin-4-yl)-5-methoxy-1,8,10-triazatricyclo[7.4.0.0$^{2,7}$]trideca-2(7),3,5,8,10,12-hexaene-11-carboxamide | Tr(MET-uHPLC-AB-101) = 2.3 min, m/z (ES$^+$) (M + H)$^+$ |
| 7 | 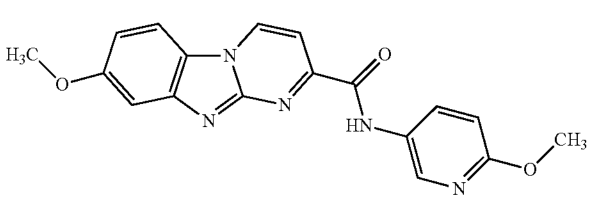 | 349.35 | 5-methoxy-N-(6-methoxypyridin-3-yl)-1,8,10-triazatricyclo[7.4.0.0$^{2,7}$]trideca-2(7),3,5,8,10,12-hexaene-11-carboxamide | Tr(METCR1600) = 3.65 min, m/z (ES$^+$) (M + H)$^+$ 350 |

Method 20

Scheme for Method 20

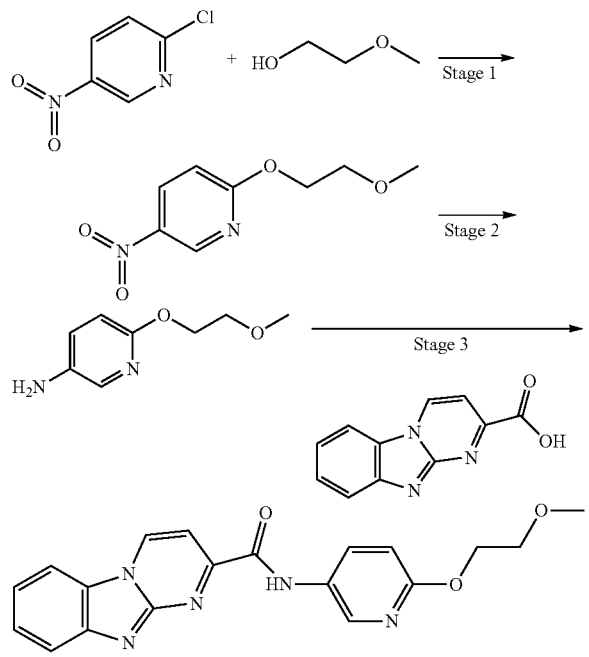

Step 1, Method 20:
2-(2-Methoxyethoxy)-5-nitropyridine

2-Methoxyethanol (5.22 mL, 66.23 mmol) was treated with sodium hydride (0.57 g, 14.2 mmol) at room temperature in several portions over 10 minutes. After stirring at room temperature for 30 minutes 2-chloro-5-nitropyridine (1.5 g, 9.5 mmol) was added in two portions and stirred for 20 minutes. The reaction was poured onto water, filtered and the solid dried in a vacuum oven overnight to give the title compound. $^1$H NMR (500 MHz, Chloroform) 9.06 (d, J=2.7 Hz, 1H), 8.35 (dd, J=9.1, 2.8 Hz, 1H), 6.89 (d, J=9.1 Hz, 1H), 4.63-4.55 (m, 2H), 3.80-3.73 (m, 2H), 3.44 (s, 3H). Tr(METCR1410)=0.94 min, m/z (ES$^+$) (M+H)$^+$ 199.

Step 2, Method 20:
6-(2-Methoxyethoxy)pyridin-3-amine

To a suspension of 2-(2-methoxyethoxy)-5-nitropyridine (500 mg, 2.52 mmol) in ethanol (20 mL) was added Palladium on charcoal (10% metal by weight) (134 mg, 0.126 mmol). The reaction vessel was flushed with nitrogen 3 times before placing under a hydrogen atmosphere (3× vacuum-hydrogen cycles) and stirred at room temperature for 6 hours. The mixture was filtered through a pad of Celite, washed with methanol and the solvent removed in vacuo to give the title compound, which was used in the next step with no further purification. Tr(METCR1410)=0.16 min, m/z (ES$^+$) (M+H)$^+$ 169.

Step 3, Method 20: N-[6-(2-Methoxyethoxy)pyridin-3-yl]-1,8,10-triazatricyclo[7.4.0.0$^{2,7}$]trideca-2(7),3,5,8,10,12-hexaene-11-carboxamide To a solution of 1,8,10-triazatricyclo[7.4.0.0$^{2,7}$]trideca-2(7),3,5,8,10,12-hexaene-11-carboxylic acid (100 mg, 0.328 mmol, prepared by Method 3) in N,N-dimethylformamide (4 ml) was added 1-[bis(dimethylamino)methylene]-1H-1,2,3-triazolo[4,5-b]pyridinium 3-oxide hexafluorophosphate (187 mg, 0.345 mmol) and N,N-diisopropylethylamine (76 μL, 0.493 mmol) at room temperature and stirred for one hour. 6-(2-Methoxyethoxy)pyridin-3-amine (66 mg, 0.394 mmol) was added and the reaction was stirred for 24 hours. The reaction mixture was concentrated in vacuo and the residue dissolved in dimethylsulfoxide and purified by preparative HPLC (high pH). The product containing fractions contained a solid which was isolated by filtration, washed with acetonitrile and dried in a vacuum oven to give the title compound.

Example 1, Method 20: N-[6-(2-Methoxyethoxy)pyridin-3-yl]-1,8,10-triazatricyclo[7.4.0.0$^{2,7}$]trideca-2(7),3,5,8,10,12-hexaene-11-carboxamide $^1$H NMR (500 MHz, DMSO) 11.06 (s, 1H), 9.77 (d, J=7.0 Hz, 1H), 8.69 (d, J=2.7 Hz, 1H), 8.43 (d, J=8.2 Hz, 1H), 8.22 (dd, J=8.9, 2.7 Hz, 1H), 7.96 (d, J=8.2 Hz, 1H), 7.77 (d, J=7.0 Hz, 1H), 7.67-7.60 (m, 1H), 7.55-7.49 (m, 1H), 6.89 (d, J=8.9 Hz, 1H), 4.38 (dd, J=5.4, 4.0 Hz, 2H), 3.68-3.65 (m, 2H), 3.31 (s, 3H). Tr(MET-uHPLC-AB-101)=2.20 min, m/z (ES$^+$) (M+H)$^+$ 364.

The following example was prepared using Method 20 described above:

TABLE 20

| Ex. | Structure | Mol. Weight | IUPAC Name | LCMS data |
|---|---|---|---|---|
| 1 | 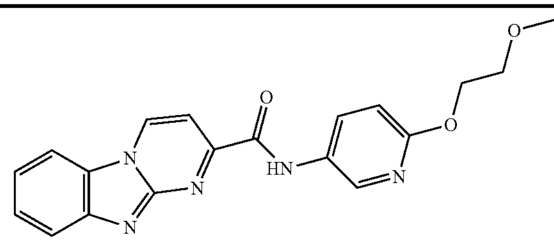 | 363.37 | N-[6-(2-methoxyethoxy)pyridin-3-yl]-1,8,10-triazatricyclo[7.4.0.0$^{2,7}$]trideca-2(7),3,5,8,10,12-hexaene-11-carbboxamide | Tr(MET-uHPLC-AB-101) = 2.20 min, m/z (ES$^+$) (M + H)$^+$ 364 |

Synthesis of 10-[$^{11}$C]-methoxy-N-(pyridin-3-yl)-7-thia-2,5-diazatricyclo[6.4.0.0$^{2,6}$]dodeca-1(12),3,5,8,10-pentaene-4-carboxamide 10-[$^{11}$C]-methoxy-N-(pyridin-3-yl)-7-thia-2,5-diazatricyclo[6.4.0.0$^{2,6}$]dodeca-1(12),3,5,8,10-pentaene-4-carboxamide was synthesized from Compound 2 of Method 2 via O-methylation, using [$^{11}$C]methyl triflate (obtained from cyclotron-produced[$^{11}$C]methane) as an alkylating agent in the presence of base according to the method of Chitneni, S. K. et al.: Synthesis and biological evaluation of carbon-11-labeled acyclic and furo[2,3-d]pyrimidine derivatives of bicyclic nucleoside analogues (BCNAs) for structurebrain uptake relationship study of BCNA tracers, Journal of Labelled Compounds and Radiopharmaceuticals 2008, 51, 159-166. The incorporation rate was >90% and the radiochemical purity was >99%. The labeled product was purified on semi-preparative HPLC column (Ascentis RP-Amide C18) using acetonitrile/aq. triethylamine (0.1%) as eluent. The product was then concentrated using solid-phase extraction procedure (on Waters tC18 Vac 1 cc SPE cartridge) and formulated in sterile saline (0.9% NaCl) with >10% ethanol. The radiochemical purity of the product was analyzed on an HPLC system using Ascentis RP-Amide C18 analytical column and acetonitrile/aq. triethylamine (0.1%) as eluent, with sequential UV absorbance and radioactivity detectors. The radiochemical purity of the formulated product was determined to be >99%.

The following compounds can be prepared according to the synthetic methods similar to those described above.

TABLE 21

| Structure | IUPAC Name |
|---|---|
| 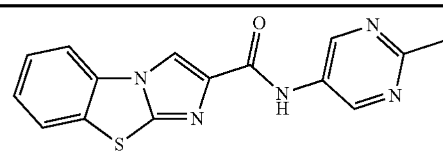 | N-(2-methylpyrimidin-5-yl)-7-thia-2,5-diazatricyclo[6.4.0.0$^{2,6}$]dodeca-1(12),3,5,8,10-pentaene-4-carboxamide |
| 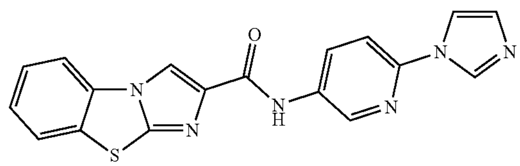 [SMILES: O=C(Nc1ccc(-n2ccnc2)nc1)c1cn2c(n1)sc1ccccc12] | N-[6-(1H-imidazol-1-yl)pyridin-3-yl]-7-thia-2,5-diazatricyclo[6.4.0.0$^{2,6}$]dodeca-1(12),3,5,8,10-pentaene-4-carboxamide |
| 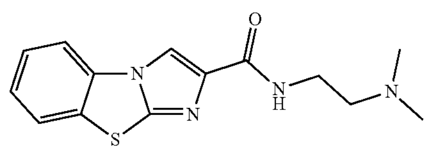 [SMILES: CN(C)CCNC(=O)c1cn2c(n1)sc1ccccc12] | N-[2-(dimethylamino)ethyl]-7-thia-2,5-diazatricyclo[6.4.0.0$^{2,6}$]dodeca-1(12),3,5,8,10-pentaene-4-carboxamide |
| 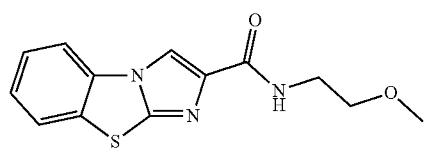 [SMILES: COCCNC(=O)c1cn2c(n1)sc1ccccc12] | N-(2-methoxyethyl)-7-thia-2,5-diazatricyclo[6.4.0.0$^{2,6}$]dodeca-1(12),3,5,8,10-pentaene-4-carboxamide |
| 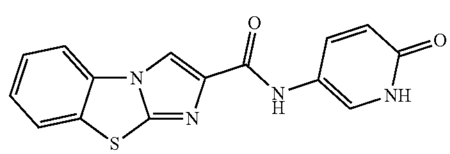 [SMILES: O=C(Nc1ccc(=O)[nH]c1)c1cn2c(n1)sc1ccccc12] | N-(6-oxo-1,6-dihydropyridin-3-yl)-7-thia-2,5-diazatricyclo[6.4.0.0$^{2,6}$]dodeca-1(12),3,5,8,10-pentaene-4-carboxamide |
| 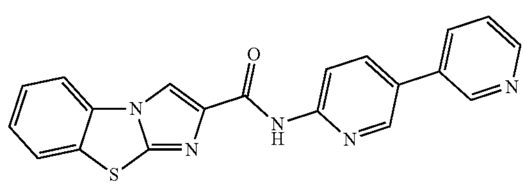 [SMILES: O=C(Nc1ccc(-c2cccnc2)cn1)c1cn2c(n1)sc1ccccc12] | N-{[3,3'-bipyridine]-6-yl}-7-thia-2,5-diazatricyclo[6.4.0.0$^{2,6}$]dodeca-1(12),3,5,8,10-pentaene-4-carboxamide |
| 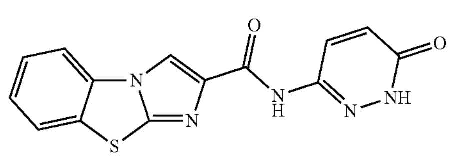 [SMILES: O=C(Nc1ccc(=O)[nH]n1)c1cn2c(n1)sc1ccccc12] | N-(6-oxo-1,6-dihydropyridazin-3-yl)-7-thia-2,5-diazatricyclo[6.4.0.0$^{2,6}$]dodeca-1(12),3,5,8,10-pentaene-4-carboxamide |
| 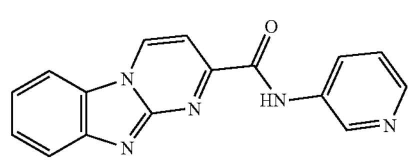 [SMILES: O=C(Nc1cccnc1)c1ccn2c(n1)nc1ccccc12] | N-(pyridin-3-yl)-1,8,10-triazatricyclo[7.4.0.0$^{2,7}$]trideca-2(7),3,5,8,10,12-hexaene-11-carboxamide |

TABLE 21-continued

| Structure | IUPAC Name |
| --- | --- |
| 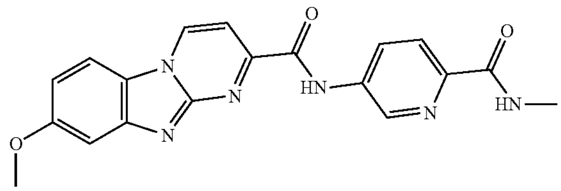 [SMILES: CNC(=O)c1ccc(NC(=O)c2ccn3c(n2)nc2cc(OC)ccc23)cn1] | 5-methoxy-N-[6-(methylcarbamoyl)pyridin-3-yl]-1,8,10-triazatricyclo[7.4.0.0$^{2,7}$]trideca-2(7),3,5,8,10,12-hexaene-11-carboxamide |
| 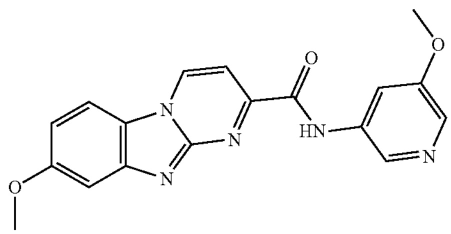 [SMILES: COc1cncc(NC(=O)c2ccn3c(n2)nc2cc(OC)ccc23)c1] | 5-methoxy-N-(5-methoxypyridin-3-yl)-1,8,10-triazatricyclo[7.4.0.0$^{2,7}$]trideca-2(7),3,5,8,10,12-hexaene-11-carboxamide |
| 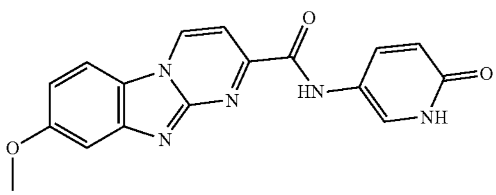 [SMILES: COc1ccc2c(c1)nc1nc(C(=O)Nc3ccc(=O)[nH]c3)ccn12] | 5-methoxy-N-(6-oxo-1,6-dihydropyridin-3-yl)-1,8,10-triazatricyclo[7.4.0.0$^{2,7}$]trideca-2(7),3,5,8,10,12-hexaene-11-carboxamide |
| 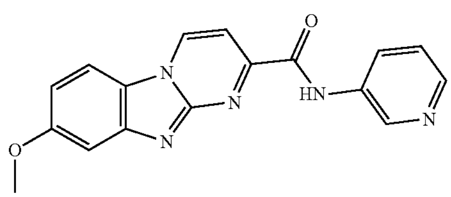 [SMILES: COc1ccc2c(c1)nc1nc(C(=O)Nc3cccnc3)ccn12] | 5-methoxy-N-(pyridin-3-yl)-1,8,10-triazatricyclo[7.4.0.0$^{2,7}$]trideca-2(7),3,5,8,10,12-hexaene-11-carboxamide |
| 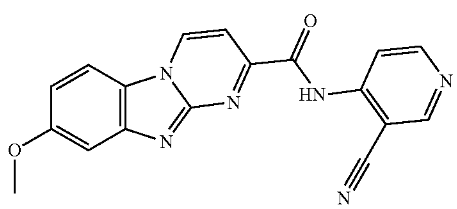 [SMILES: COc1ccc2c(c1)nc1nc(C(=O)Nc3ccncc3C#N)ccn12] | N-(3-cyanopyridin-4-yl)-5-methoxy-1,8,10-triazatricyclo[7.4.0.0$^{2,7}$]trideca-2(7),3,5,8,10,12-hexaene-11-carboxamide |
| 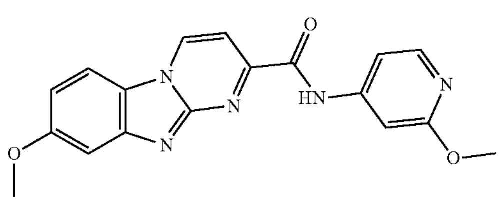 [SMILES: COc1ccc2c(c1)nc1nc(C(=O)Nc3ccnc(OC)c3)ccn12] | 5-methoxy-N-(2-methoxypyridin-4-yl)-1,8,10-triazatricyclo[7.4.0.0$^{2,7}$]trideca-2(7),3,5,8,10,12-hexaene-11-carboxamide |
| 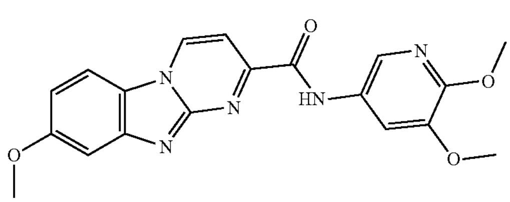 [SMILES: COc1ccc2c(c1)nc1nc(C(=O)Nc3cnc(OC)c(OC)c3)ccn12] | N-(5,6-dimethoxypyridin-3-yl)-5-methoxy-1,8,10-triazatricyclo[7.4.0.0$^{2,7}$]trideca-2(7),3,5,8,10,12-hexaene-11-carboxamide |

TABLE 21-continued

| Structure | IUPAC Name |
|---|---|
| 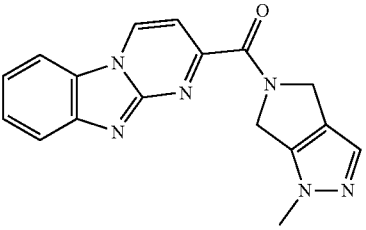 [SMILES: Cn1ncc2c1CN(C(=O)c1ccn3c(n1)nc1ccccc13)C2] | 11-{1-methyl-1H,4H,5H,6H-pyrrolo[3,4-c]pyrazole-5-carbonyl}-1,8,10-triazatricyclo[7.4.0.0²,⁷]trideca-2(7),3,5,8,10,12-hexaene |
| 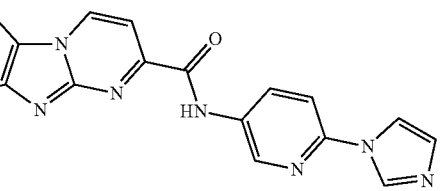 | N-[6-(1H-imidazol-1-yl)pyridin-3-yl]-1,8,10-triazatricyclo[7.4.0.0²,⁷]trideca-2(7),3,5,8,10,12-hexaene-11-carboxamide |
| 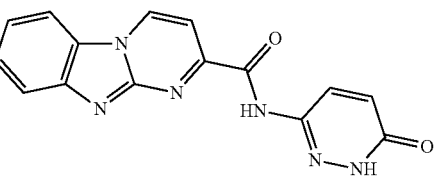 | 5-methoxy-N-(6-oxo-1,6-dihydropyridazin-3-yl)-1,8,10-triazatricyclo[7.4.0.0²,⁷]trideca-2(7),3,5,8,10,12-hexaene-11-carboxamide |
| 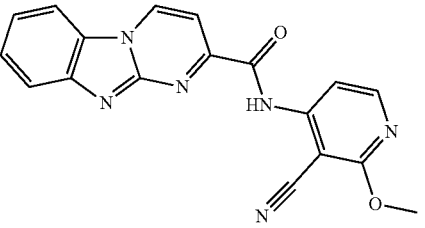 | N-(3-cyano-2-methoxypyridin-4-yl)-5-methoxy-1,8,10-triazatricyclo[7.4.0.0²,⁷]trideca-2(7),3,5,8,10,12-hexaene-11-carboxamide |
| 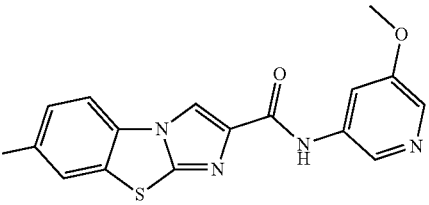 | 10-methoxy-N-(5-methoxypyridin-3-yl)-7-thia-2,5-diazatricyclo[6.4.0.0²,⁶]dodeca-1(12),3,5,8,10-pentaene-4-carboxamide |
| 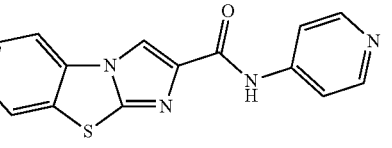 | N-(pyridin-4-yl)-7-thia-2,5-diazatricyclo[6.4.0.0²,⁶]dodeca-1(12),3,5,8,10-pentaene-4-carboxamide |
| 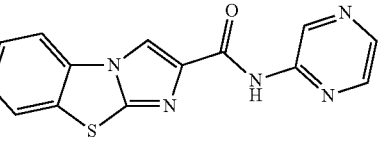 | N-(pyrazin-2-yl)-7-thia-2,5-diazatricyclo[6.4.0.0²,⁶]dodeca-1(12),3,5,8,10-pentaene-4-carboxamide |
| 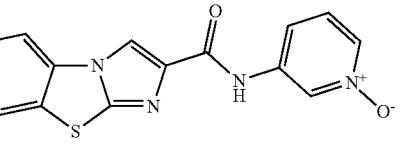 | 3-{7-thia-2,5-diazatricyclo[6.4.0.0²,⁶]dodeca-1(12),3,5,8,10-pentaene-4-amido}pyridin-1-ium-1-olate |

TABLE 21-continued

| Structure | IUPAC Name |
|---|---|
| | 5-methoxy-N-(1-methyl-6-oxo-1,6-dihydropyridin-3-yl)-1,8,10-triazatricyclo[7.4.0.0²,⁷]trideca-2(7),3,5,8,10,12-hexaene-11-carboxamide |
| | N-(5-methoxypyridin-3-yl)-5-thia-2,7-diazatricyclo[6.4.0.0²,⁶]dodeca-1(12),3,6,8,10-pentaene-4-carboxamide |
| | N-(1-methyl-6-oxo-1,6-dihydropyridazin-3-yl)-5-thia-2,7-diazatricyclo[6.4.0.0²,⁶]dodeca-1(12),3,6,8,10-pentaene-4-carboxamide |
| | N-(2-methylpyrimidin-5-yl)-5-thia-2,7-diazatricyclo[6.4.0.0²,⁶]dodeca-1(8),3,6,9,11-pentaene-4-carboxamide |
| | 5-methoxy-N-(1-methyl-2-oxo-1,2-dihydropyrimidin-5-yl)-1,8,10-triazatricyclo[7.4.0.0²,⁷]trideca-2(7),3,5,8,10,12-hexaene-11-carboxamide |
| | N-{3-[(methylamino)methyl]phenyl}-7-thia-2,5-diazatricyclo[6.4.0.0²,⁶]dodeca-1(8),3,5,9,11-pentaene-4-carboxamide |
| | 5-methoxy-N-[5-(2-methoxyethoxy)pyridin-3-yl]-1,8,10-triazatricyclo[7.4.0.0²,⁷]trideca-2(7),3,5,8,10,12-hexaene-11-carboxamide |
| | N-(pyridin-3-yl)-7-thia-2,5-diazatricyclo[6.4.0.0²,⁶]dodeca-1(8),3,5,9,11-pentaene-4-carboxamide |

TABLE 21-continued

| Structure | IUPAC Name |
|---|---|
| | N-(6-methoxypyridin-3-yl)-7-thia-2,5-diazatricyclo[6.4.0.0²,⁶]dodeca-1(8),3,5,9,11-pentaene-4-carboxamide |
| | N-[(pyridin-3-yl)methyl]-7-thia-2,5-diazatricyclo[6.4.0.0²,⁶]dodeca-1(8),3,5,9,11-pentaene-4-carboxamide |
| | N-methyl-N-(pyridin-3-yl)-7-thia-2,5-diazatricyclo[6.4.0.0²,⁶]dodeca-1(8),3,5,9,11-pentaene-4-carboxamide |
| | N-(1-benzofuran-5-yl)-7-thia-2,5-diazatricyclo[6.4.0.0²,⁶]dodeca-1(8),3,5,9,11-pentaene-4-carboxamide |
| | N-(1-methyl-1H-pyrazol-4-yl)-7-thia-2,5-diazatricyclo[6.4.0.0²,⁶]dodeca-1(8),3,5,9,11-pentaene-4-carboxamide |
| | N-(6-fluoropyridin-3-yl)-7-thia-2,5-diazatricyclo[6.4.0.0²,⁶]dodeca-1(8),3,5,9,11-pentaene-4-carboxamide |
| | N-[6-(methylcarbamoyl)pyridin-3-yl]-7-thia-2,5-diazatricyclo[6.4.0.0²,⁶]dodeca-1(8),3,5,9,11-pentaene-4-carboxamide |
| | 4-{1H,2H,3H-pyrrolo[2,3-c]pyridine-1-carbonyl}-7-thia-2,5-diazatricyclo[6.4.0.0²,⁶]dodeca-1(8),3,5,9,11-pentaene |
| | 4-{1-methyl-1H,4H,5H,6H-pyrrolo[3,4-c]pyrazole-5-carbonyl}-7-thia-2,5-diazatricyclo[6.4.0.0²,⁶]dodeca-1(8),3,5,9,11-pentaene |

TABLE 21-continued

| Structure | IUPAC Name |
|---|---|
| 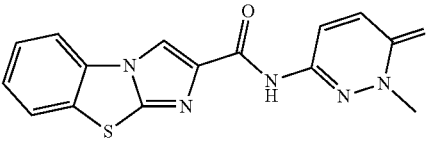 | N-(1-methyl-6-oxo-1,6-dihydropyridazin-3-yl)-7-thia-2,5-diazatricyclo[6.4.0.0²,⁶]dodeca-1(12),3,5,8,10-pentaene-4-carboxamide |
| 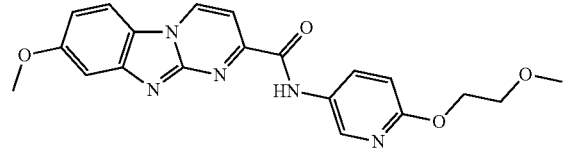 | 5-methoxy-N-[6-(2-methoxyethoxy)pyridin-3-yl]-1,8,10-triazatricyclo[7.4.0.0²,⁷]trideca-2(7),3,5,8,10,12-hexaene-11-carboxamide |
| 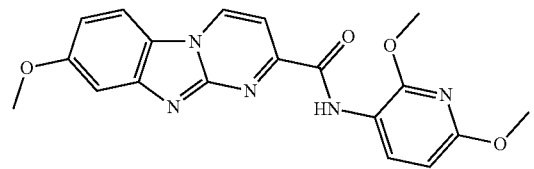 | N-(2,6-dimethoxypyridin-3-yl)-5-methoxy-1,8,10-triazatricyclo[7.4.0.0²,⁷]trideca-2(7),3,5,8,10,12-hexaene-11-carboxamide |
| 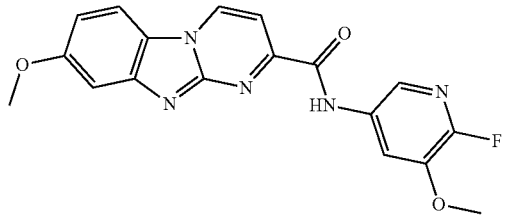 [SMILES: COc1ccc2c(c1)nc1nc(C(=O)Nc3cnc(F)c(OC)c3)ccn12] | N-(6-fluoro-5-methoxypyridin-3-yl)-5-methoxy-1,8,10-triazatricyclo[7.4.0.0²,⁷]trideca-2(7),3,5,8,10,12-hexaene-11-carboxamide |
| 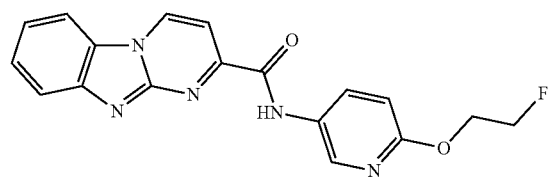 [SMILES: O=C(Nc1ccc(OCCF)nc1)c1ccn2c(n1)nc1ccccc12] | N-[6-(2-fluoroethoxy)pyridin-3-yl]-1,8,10-triazatricyclo[7.4.0.0²,⁷]trideca-2(7),3,5,8,10,12-hexaene-11-carboxamide |
| 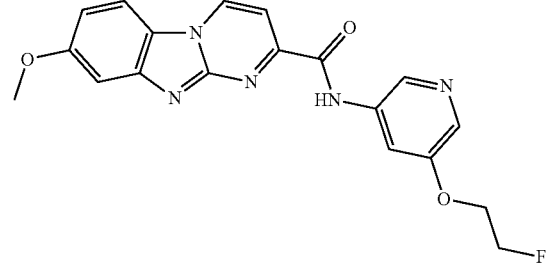 [SMILES: COc1ccc2c(c1)nc1nc(C(=O)Nc3cncc(OCCF)c3)ccn12] | N-[5-(2-fluoroethoxy)pyridin-3-yl]-5-methoxy-1,8,10-triazatricyclo[7.4.0.0²,⁷]trideca-2(7),3,5,8,10,12-hexaene-11-carboxamide |
| 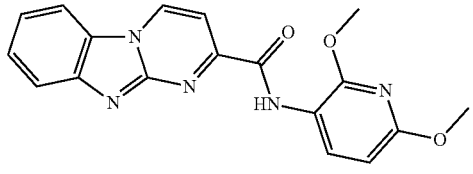 [SMILES: COc1ccc(NC(=O)c2ccn3c(n2)nc2ccccc23)c(OC)n1] | N-(2,6-dimethoxypyridin-3-yl)-1,8,10-triazatricyclo[7.4.0.0²,⁷]trideca-2(7),3,5,8,10,12-hexaene-11-carboxamide |
| 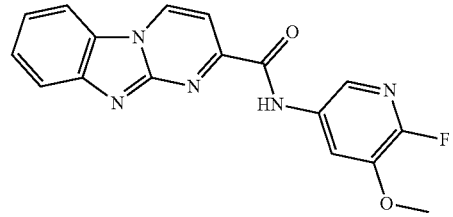 [SMILES: COc1cc(NC(=O)c2ccn3c(n2)nc2ccccc23)cnc1F] | N-(6-fluoro-5-methoxypyridin-3-yl)-1,8,10-triazatricyclo[7.4.0.0²,⁷]trideca-2(7),3,5,8,10,12-hexaene-11-carboxamide |

TABLE 21-continued

| Structure | IUPAC Name |
|---|---|
| 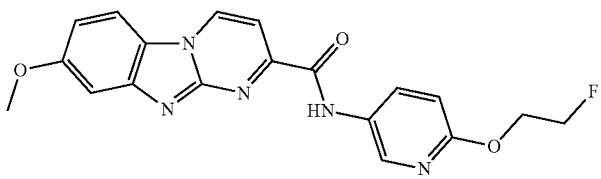 [SMILES: COc1ccc2c(c1)nc1nc(C(=O)Nc3ccc(OCCF)nc3)ccn12] | N-[6-(2-fluoroethoxy)pyridin-3-yl]-5-methoxy-1,8,10-triazatricyclo[7.4.0.0$^{2,7}$]trideca-2(7),3,5,8,10,12-hexaene-11-carboxamide |
| 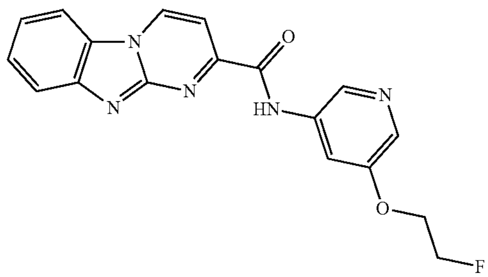 [SMILES: O=C(Nc1cncc(OCCF)c1)c1ccn2c(n1)nc1ccccc12] | N-[5-(2-fluoroethoxy)pyridin-3-yl]-1,8,10-triazatricyclo[7.4.0.0$^{2,7}$]trideca-2(7),3,5,8,10,12-hexaene-11-carboxamide |
| 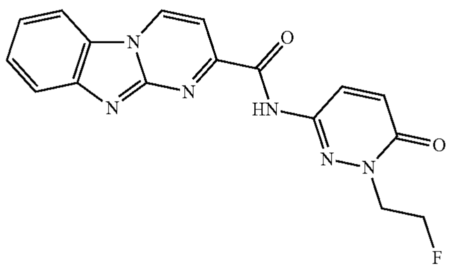 [SMILES: O=C(Nc1ccc(=O)n(CCF)n1)c1ccn2c(n1)nc1ccccc12] | N-[1-(2-fluoroethyl)-6-oxo-1,6-dihydropyridazin-3-yl]-1,8,10-triazatricyclo[7.4.0.0$^{2,7}$]trideca-2(7),3,5,8,10,12-hexaene-11-carboxamide |
| 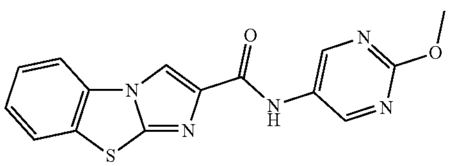 [SMILES: COc1ncc(NC(=O)c2cn3c(n2)sc2ccccc23)cn1] | N-(2-methoxypyrimidin-5-yl)-7-thia-2,5-diazatricyclo[6.4.0.0$^{2,6}$]dodeca-1(8),3,5,9,11-pentaene-4-carboxamide |
| 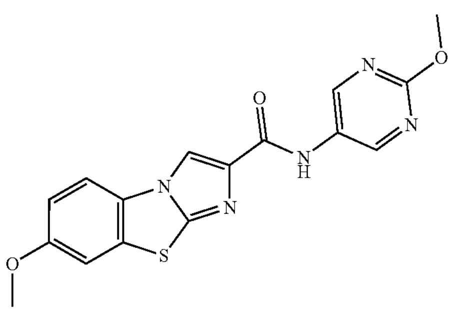 [SMILES: COc1ccc2c(c1)sc1nc(C(=O)Nc3cnc(OC)nc3)cn12] | 10-methoxy-N-(2-methoxypyrimidin-5-yl)-7-thia-2,5-diazatricyclo[6.4.0.0$^{2,6}$]dodeca-1(8),3,5,9,11-pentaene-4-carboxamide |

BIOLOGY EXAMPLES

Example A

Q46 Radioligand Binding Assay

For radioligand binding assays (RBA) GST-Q46 protein was generated based on a previous publication (Scherzinger et al. Cell, Vol. 90, 549-558, Aug. 8, 1997). For experiments 33 μM GST-Q46 was incubated with 150 μg/mL thrombin in assay buffer (150 mM NaCl, 50 mM Tris pH 8.0) and 2 mM CaCl$_2$ for 16 hours at 37° C. Aggregated Q46 was pelleted by centrifugation for 5 minutes at 13,000 rpm in a bench top centrifuge and re-dissolved in the same volume of assay buffer. Test compounds were prepared by titration in DMSO at 11 concentrations from 33 μM to 1 nM. For the RBA, Q46 protein aggregates and test compounds were pre-incubated in assay buffer for 20 minutes at room temperature, in 140 μL/well in a 96-well plate (pp, round bottom). Then, ligand was added in 10 μL/well and incubated for 60 minutes at 37° C. Final assay concentrations were 1 μM to 30 pM test compound, 5 μM Q46 protein (equivalent monomer concentration) and 10 nM ligand [$^3$H$_3$]MK-3328 (Harrision et al., ACS Med. Chem. Lett., 2 (2011), pp 498-502). Samples were transferred onto GF/B filter plates and washed 2× with 200 μL PBS using a Filtermate Harvester. After drying filter plates for 1 hour at 37° C., the back of the plates was sealed with foil and 30 µl/well scintillation fluid (Packard MicroScint 40) was added, incubated for incubated for 15 minutes in the dark and counted in a TopCount reader. For analysis, replicate data from independent assay plates were normalized towards 0% and 100% inhibition using control wells of vehicle (0% inhibition) and 3 µM unlabelled MK-3328 (100% inhibition). $IC_{50}$ values were determined with a sigmoidal inhibition model with four variables (top, bottom, slope, $IC_{50}$) in a global fit using the normalized replicate data.

RBA $IC_{50}$ activity summary <100 nM+++, 100-500 nM++, >500 nM+

TABLE 22

| Structure | IUPAC Name | Activity |
|---|---|---|
| 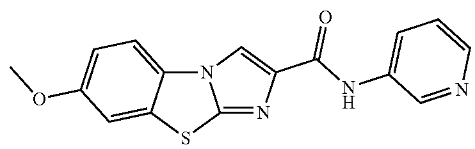 [SMILES: COc1ccc2c(c1)sc1nc(C(=O)Nc3cccnc3)cn12] | 10-methoxy-N-(pyridin-3-yl)-7-thia-2,5-diazatricyclo[6.4.0.0$^{2,6}$]dodeca-1(12),3,5,8,10-pentaene-4-carboxamide | +++ |
| 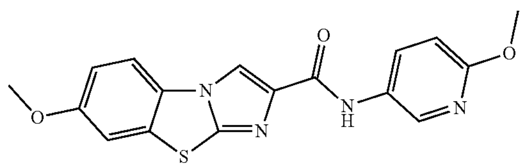 | 10-methoxy-N-(6-methoxypyridin-3-yl)-7-thia-2,5-diazatricyclo[6.4.0.0$^{2,6}$]dodeca-1(12),3,5,8,10-pentaene-4-carboxamide | +++ |
| 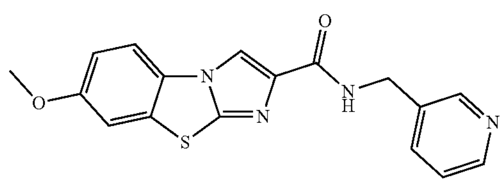 [SMILES: COc1ccc2c(c1)sc1nc(C(=O)NCc3cccnc3)cn12] | 10-methoxy-N-(pyridin-3-ylmethyl)-7-thia-2,5-diazatricyclo[6.4.0.0$^{2,6}$]dodeca-1(12),3,5,8,10-pentaene-4-carboxamide | + |
| 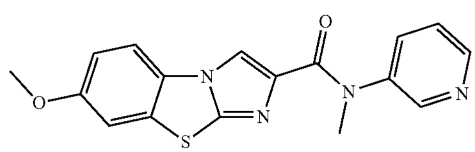 [SMILES: COc1ccc2c(c1)sc1nc(C(=O)N(C)c3cccnc3)cn12] | 10-methoxy-N-methyl-N-(pyridin-3-yl)-7-thia-2,5-diazatricyclo[6.4.0.0$^{2,6}$]dodeca-1(12),3,5,8,10-pentaene-4-carboxamide | ++ |
| 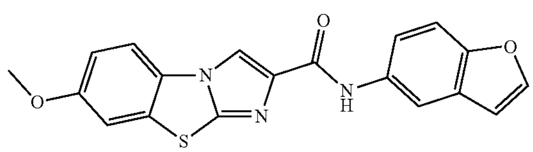 [SMILES: COc1ccc2c(c1)sc1nc(C(=O)Nc3ccc4occc4c3)cn12] | N-(1-benzofuran-5-yl)-10-methoxy-7-thia-2,5-diazatricyclo[6.4.0.0$^{2,6}$]dodeca-1(12),3,5,8,10-pentaene-4-carboxamide | +++ |
| 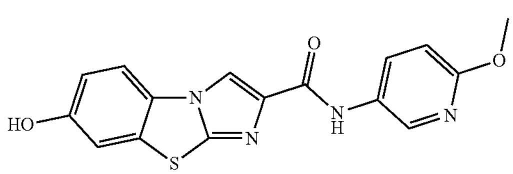 [SMILES: COc1ccc(NC(=O)c2cn3c(n2)sc2cc(O)ccc23)cn1] | 10-hydroxy-N-(6-methoxypyridin-3-yl)-7-thia-2,5-diazatricyclo[6.4.0.0$^{2,6}$]dodeca-1(12),3,5,8,10-pentaene-4-carboxamide | +++ |
| 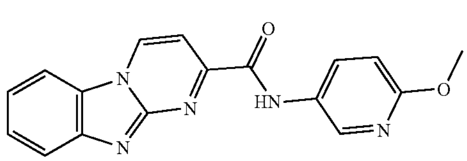 [SMILES: COc1ccc(NC(=O)c2ccn3c(n2)nc2ccccc23)cn1] | N-(6-methoxypyridin-3-yl)-1,8,10-triazatricyclo[7.4.0.0$^{2,7}$]trideca-2(7),3,5,8,10,12-hexaene-11-carboxamide | +++ |
| 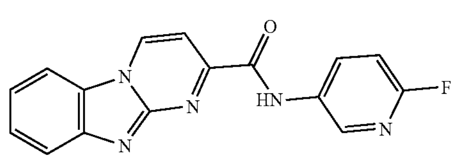 [SMILES: O=C(Nc1ccc(F)nc1)c1ccn2c(n1)nc1ccccc12] | N-(6-fluoropyridin-3-yl)-1,8,10-triazatricyclo[7.4.0.0$^{2,7}$]trideca-2(7),3,5,8,10,12-hexaene-11-carboxamide | +++ |

TABLE 22-continued

| Structure | IUPAC Name | Activity |
|---|---|---|
|  | 10-hydroxy-N-(pyridin-3-yl)-7-thia-2,5-diazatricyclo[6.4.0.0²,⁶]dodeca-1(12),3,5,8,10-pentaene-4-carboxamide | +++ |
|  | 10-methoxy-N-(5-methoxypyridin-3-yl)-7-thia-2,5-diazatricyclo[6.4.0.0²,⁶]dodeca-1(12),3,5,8,10-pentaene-4-carboxamide | +++ |
|  | 10-methoxy-N-(1-methyl-1H-pyrazol-4-yl)-7-thia-2,5-diazatricyclo[6.4.0.0²,⁶]dodeca-1(12),3,5,8,10-pentaene-4-carboxamide | ++ |
|  | N-(6-fluoropyridin-3-yl)-10-methoxy-7-thia-2,5-diazatricyclo[6.4.0.0²,⁶]dodeca-1(12),3,5,8,10-pentaene-4-carboxamide | +++ |
|  | 10-methoxy-N-(pyridin-3-yl)-7-thia-2,5,9-triazatricyclo[6.4.0.0²,⁶]dodeca-1(12),3,5,8,10-pentaene-4-carboxamide | +++ |
|  | 10-methoxy-N-(5-methoxypyridin-3-yl)-7-thia-2,5,9-triazatricyclo[6.4.0.0²,⁶]dodeca-1(12),3,5,8,10-pentaene-4-carboxamide | +++ |
|  | 10-methoxy-N-[6-(methylcarbamoyl)pyridin-3-yl]-7-thia-2,5-diazatricyclo[6.4.0.0²,⁶]dodeca-1(12),3,5,8,10-pentaene-4-carboxamide | +++ |
|  | 10-methoxy-4-{1H,2H,3H-pyrrolo[2,3-c]pyridine-1-carbonyl}-7-thia-2,5-diazatricyclo[6.4.0.0²,⁶]dodeca-1(12),3,5,8,10-pentaene | + |
|  | 10-methoxy-N-(6-methylpyridin-3-yl)-7-thia-2,5-diazatricyclo[6.4.0.0²,⁶]dodeca-1(12),3,5,8,10-pentaene-4-carboxamide | +++ |

TABLE 22-continued

| Structure | IUPAC Name | Activity |
|---|---|---|
| 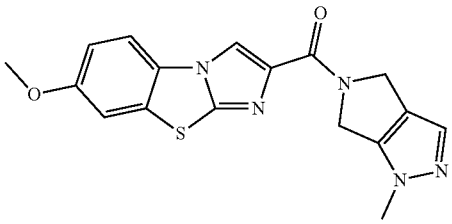 [SMILES: COc1ccc2c(c1)sc1nc(C(=O)N3Cc4cnn(C)c4C3)cn12] | 10-methoxy-4-{1-methyl-1H,4H,5H,6H-pyrrolo[3,4-c]pyrazole-5-carbonyl}-7-thia-2,5-diazatricyclo[6.4.0.0$^{2,6}$]dodeca-1(12),3,5,8,10-pentaene | +++ |
| 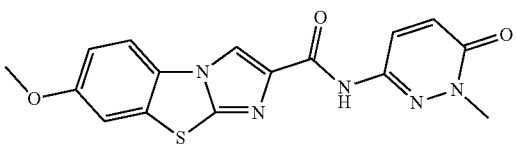 [SMILES: COc1ccc2c(c1)sc1nc(C(=O)Nc3ccc(=O)n(C)n3)cn12] | 10-methoxy-N-(1-methyl-6-oxo-1,6-dihydropyridazin-3-yl)-7-thia-2,5-diazatricyclo[6.4.0.0$^{2,6}$]dodeca-1(12),3,5,8,10-pentaene-4-carboxamide | +++ |
| 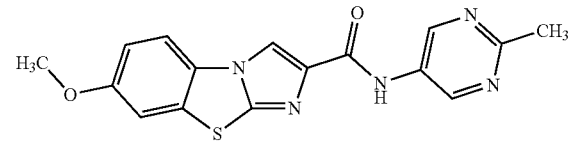 | 10-methoxy-N-(2-methylpyrimidin-5-yl)-7-thia-2,5-diazatricyclo[6.4.0.0$^{2,6}$]dodeca-1(12),3,5,8,10-pentaene-4-carboxamide | +++ |
| 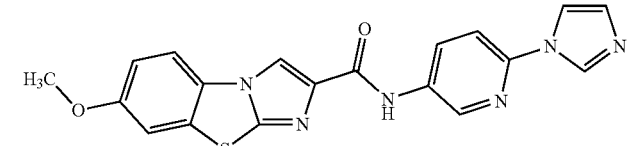 | N-[6-(1H-imidazol-1-yl)pyridin-3-yl]-10-methoxy-7-thia-2,5-diazatricyclo[6.4.0.0$^{2,6}$]dodeca-1(12),3,5,8,10-pentaene-4-carboxamide | +++ |
| 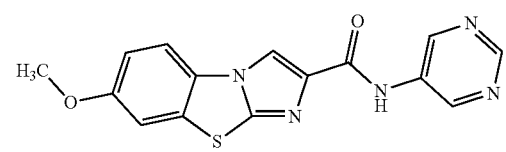 [SMILES: COc1ccc2c(c1)sc1nc(C(=O)Nc3cncnc3)cn12] | 10-methoxy-N-(pyrimidin-5-yl)-7-thia-2,5-diazatricyclo[6.4.0.0$^{2,6}$]dodeca-1(12),3,5,8,10-pentaene-4-carboxamide | +++ |
| 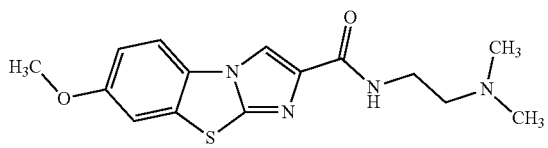 | N-[2-(dimethylamino)ethyl]-10-methoxy-7-thia-2,5-diazatricyclo[6.4.0.0$^{2,6}$]dodeca-1(12),3,5,8,10-pentaene-4-carboxamide | ++ |
| 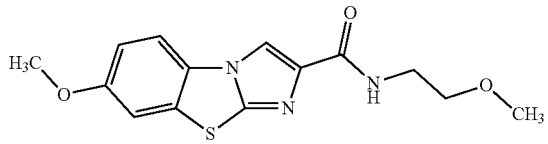 | 10-methoxy-N-(2-methoxyethyl)-7-thia-2,5-diazatricyclo[6.4.0.0$^{2,6}$]dodeca-1(12),3,5,8,10-pentaene-4-carboxamide | ++ |
| 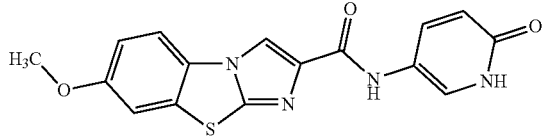 [SMILES: COc1ccc2c(c1)sc1nc(C(=O)Nc3ccc(=O)[nH]c3)cn12] | 10-methoxy-N-(6-oxo-1,6-dihydropyridin-3-yl)-7-thia-2,5-diazatricyclo[6.4.0.0$^{2,6}$]dodeca-1(12),3,5,8,10-pentaene-4-carboxamide | +++ |
| 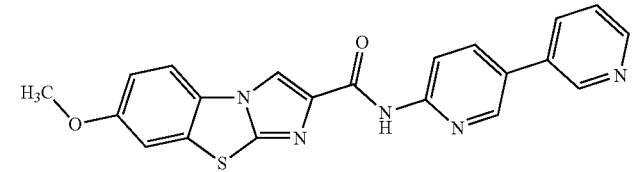 [SMILES: COc1ccc2c(c1)sc1nc(C(=O)Nc3ccc(-c4cccnc4)cn3)cn12] | 10-methoxy-N-[5-(pyridin-3-yl)pyridin-2-yl]-7-thia-2,5-diazatricyclo[6.4.0.0$^{2,6}$]dodeca-1(12),3,5,8,10-pentaene-4-carboxamide | +++ |

TABLE 22-continued

| Structure | IUPAC Name | Activity |
|---|---|---|
| | 10-methoxy-N-(6-oxo-1,6-dihydropyridazin-3-yl)-7-thia-2,5-diazatricyclo[6.4.0.0²,⁶]dodeca-1(12),3,5,8,10-pentaene-4-carboxamide | +++ |
| | 5-methoxy-N-(pyridin-3-yl)-1,8,10-triazatricyclo[7.4.0.0²,⁷]trideca-2(7),3,5,8,10,12-hexaene-11-carboxamide | +++ |
| | N-[6-(methylcarbamoyl)pyridin-3-yl]-1,8,10-triazatricyclo[7.4.0.0²,⁷]trideca-2(7),3,5,8,10,12-hexaene-11-carboxamide | +++ |
| | N-(5-methoxypyridin-3-yl)-1,8,10-triazatricyclo[7.4.0.0²,⁷]trideca-2(7),3,5,8,10,12-hexaene-11-carboxamide | +++ |
| | N-(1-methyl-6-oxo-1,6-dihydropyridazin-3-yl)-1,8,10-triazatricyclo[7.4.0.0²,⁷]trideca-2(7),3,5,8,10,12-hexaene-11-carboxamide | +++ |
| | N-(6-oxo-1,6-dihydropyridin-3-yl)-1,8,10-triazatricyclo[7.4.0.0²,⁷]trideca-2(7),3,5,8,10,12-hexaene-11-carboxamide | +++ |
| | N-(pyridin-3-yl)-1,8,10-triazatricyclo[7.4.0.0²,⁷]trideca-2(7),3,5,8,10,12-hexaene-11-carboxamide | + |
| | N-(3-cyanopyridin-4-yl)-1,8,10-triazatricyclo[7.4.0.0²,⁷]trideca-2(7),3,5,8,10,12-hexaene-11-carboxamide | +++ |
| | N-(2-methoxypyridin-4-yl)-1,8,10-triazatricyclo[7.4.0.0²,⁷]trideca-2(7),3,5,8,10,12-hexaene-11-carboxamide | +++ |

TABLE 22-continued

| Structure | IUPAC Name | Activity |
|---|---|---|
| | N-(5,6-dimethoxypyridin-3-yl)-1,8,10-triazatricyclo[7.4.0.0²,⁷]trideca-2(7),3,5,8,10,12-hexaene-11-carboxamide | +++ |
| | 5-methoxy-N-(1-methyl-6-oxo-1,6-dihydropyridazin-3-yl)-1,8,10-triazatricyclo[7.4.0.0²,⁷]trideca-2(7),3,5,8,10,12-hexaene-11-carboxamide | +++ |
| | 5-methoxy-11-{1-methyl-1H,4H,5H,6H-pyrrolo[3,4-c]pyrazole-5-carbonyl}-1,8,10-triazatricyclo[7.4.0.0²,⁷]trideca-2(7),3,5,8,10,12-hexaene | +++ |
| | 4-methoxy-N-(5-methoxypyridin-3-yl)-1,8,10-triazatricyclo[7.4.0.0²,⁷]trideca-2(7),3,5,8,10,12-hexaene-11-carboxamide | +++ |
| | 5-methoxy-N-(5-methoxypyridin-3-yl)-1,8,10-triazatricyclo[7.4.0.0²,⁷]trideca-2(7),3,5,8,10,12-hexaene-11-carboxamide | +++ |
| | N-[6-(1H-imidazol-1-yl)pyridin-3-yl]-5-methoxy-1,8,10-triazatricyclo[7.4.0.0²,⁷]trideca-2(7),3,5,8,10,12-hexaene-11-carboxamide | +++ |
| | N-(3-cyanopyridin-4-yl)-5-methoxy-1,8,10-triazatricyclo[7.4.0.0²,⁷]trideca-2(7),3,5,8,10,12-hexaene-11-carboxamide | +++ |

TABLE 22-continued

| Structure | IUPAC Name | Activity |
|---|---|---|
| 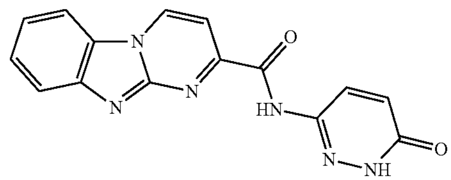 [SMILES: O=C(Nc1ccc(=O)[nH]n1)c1ccn2c(n1)nc1ccccc12] | N-(6-oxo-1,6-dihydropyridazin-3-yl)-1,8,10-triazatricyclo[7.4.0.0$^{2,7}$]trideca-2(7),3,5,8,10,12-hexaene-11-carboxamide | +++ |
| 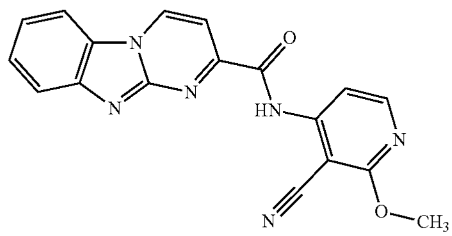 [SMILES: COc1nccc(NC(=O)c2ccn3c(n2)nc2ccccc23)c1C#N] | N-(3-cyano-2-methoxypyridin-4-yl)-1,8,10-triazatricyclo[7.4.0.0$^{2,7}$]trideca-2(7),3,5,8,10,12-hexaene-11-carboxamide | +++ |
| 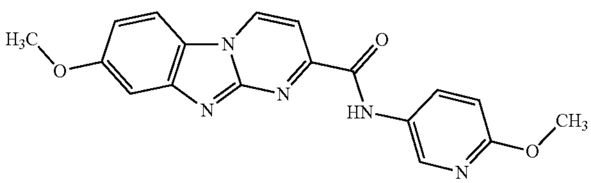 | 5-methoxy-N-(6-methoxypyridin-3-yl)-1,8,10-triazatricyclo[7.4.0.0$^{2,7}$]trideca-2(7),3,5,8,10,12-hexaene-11-carboxamide | +++ |
| 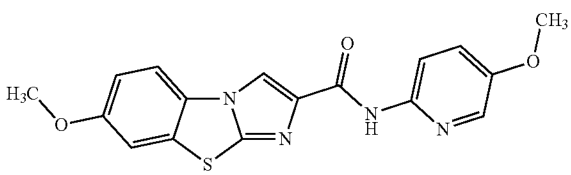 | 10-methoxy-N-(5-methoxypyridin-2-yl)-7-thia-2,5-diazatricyclo[6.4.0.0$^{2,6}$]dodeca-1(12),3,5,8,10-pentaene-4-carboxamide | +++ |
| 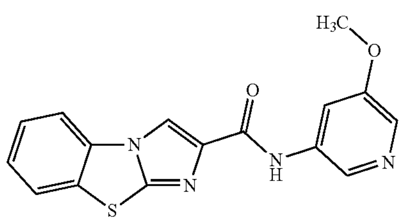 [SMILES: COc1cncc(NC(=O)c2cn3c(n2)sc2ccccc23)c1] | N-(5-methoxypyridin-3-yl)-7-thia-2,5-diazatricyclo[6.4.0.0$^{2,6}$]dodeca-1(12),3,5,8,10-pentaene-4-carboxamide | +++ |
| 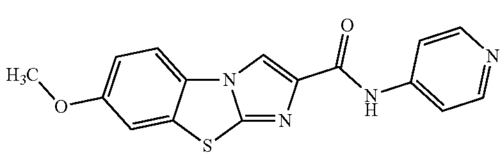 [SMILES: COc1ccc2c(c1)sc1nc(C(=O)Nc3ccncc3)cn12] | 10-methoxy-N-(pyridin-4-yl)-7-thia-2,5-diazatricyclo[6.4.0.0$^{2,6}$]dodeca-1(12),3,5,8,10-pentaene-4-carboxamide | +++ |
| 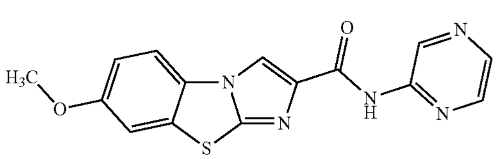 [SMILES: COc1ccc2c(c1)sc1nc(C(=O)Nc3cnccn3)cn12] | 10-methoxy-N-(pyrazin-2-yl)-7-thia-2,5-diazatricyclo[6.4.0.0$^{2,6}$]dodeca-1(12),3,5,8,10-pentaene-4-carboxamide | +++ |
| 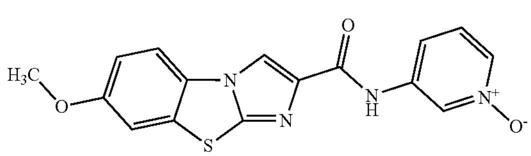 [SMILES: COc1ccc2c(c1)sc1nc(C(=O)Nc3ccc[n+]([O-])c3)cn12] | 3-{10-methoxy-7-thia-2,5-diazatricyclo[6.4.0.0$^{2,6}$]dodeca-1(12),3,5,8,10-pentaene-4-amido}pyridin-1-ium-1-olate | ++ |

TABLE 22-continued

| Structure | IUPAC Name | Activity |
|---|---|---|
| | 10-(2-fluoroethoxy)-N-(pyridin-3-yl)-7-thia-2,5-diazatricyclo[6.4.0.0²,⁶]dodeca-1(8),3,5,9,11-pentaene-4-carboxamide | +++ |
| | N-({10-methoxy-7-thia-2,5-diazatricyclo[6.4.0.0²,⁶]dodeca-1(12),3,5,8,10-pentaen-4-yl}methyl)pyridin-3-amine | + |
| | 10-[(5-methoxypyridin-2-yl)methoxy]-N-(5-methoxypyridin-3-yl)-7-thia-2,5-diazatricyclo[6.4.0.0²,⁶]dodeca-1(12),3,5,8,10-pentaene-4-carboxamide | +++ |
| | N-(1-methyl-6-oxo-1,6-dihydropyridin-3-yl)-1,8,10-triazatricyclo[7.4.0.0²,⁷]trideca-2(7),3,5,8,10,12-hexaene-11-carboxamide | ++ |
| | 11-bromo-N-(5-methoxypyridin-3-yl)-7-thia-2,5,9-triazatricyclo[6.4.0.0²,⁶]dodeca-1(12),3,5,8,10-pentaene-4-carboxamide | +++ |
| | N-(1-methyl-6-oxo-1,6-dihydropyridazin-3-yl)-10-(prop-2-en-1-yloxy)-7-thia-2,5-diazatricyclo[6.4.0.0²,⁶]dodeca-1(12),3,5,8,10-pentaene-4-carboxamide | +++ |
| | 10-methoxy-N-(5-methoxypyridin-3-yl)-5-thia-2,7-diazatricyclo[6.4.0.0²,⁶]dodeca-1(12),3,6,8,10-pentaene-4-carboxamide | +++ |
| | 10-methoxy-N-(1-methyl-6-oxo-1,6-dihydropyridazin-3-yl)-5-thia-2,7-diazatricyclo[6.4.0.0²,⁶]dodeca-1(12),3,6,8,10-pentaene-4-carboxamide | +++ |
| | 10-methoxy-N-(2-methylpyrimidin-5-yl)-5-thia-2,7-diazatricyclo[6.4.0.0²,⁶]dodeca-1(8),3,6,9,11-pentaene-4-carboxamide | +++ |

TABLE 22-continued

| Structure | IUPAC Name | Activity |
|---|---|---|
| | N-(1-methyl-2-oxo-1,2-dihydropyrimidin-5-yl)-1,8,10-triazatricyclo[7.4.0.0²,⁷]trideca-2(7),3,5,8,10,12-hexaene-11-carboxamide | +++ |
| | 11-methoxy-N-(5-methoxypyridin-3-yl)-7-thia-2,5,9-triazatricyclo[6.4.0.0²,⁶]dodeca-1(12),3,5,8,10-pentaene-4-carboxamide | +++ |
| | 11-methoxy-N-(1-methyl-6-oxo-1,6-dihydropyridazin-3-yl)-7-thia-2,5,9-triazatricyclo[6.4.0.0²,⁶]dodeca-1(12),3,5,8,10-pentaene-4-carboxamide | +++ |
| | 10-methoxy-N-{3-[(methylamino)methyl]phenyl}-7-thia-2,5-diazatricyclo[6.4.0.0²,⁶]dodeca-1(8),3,5,9,11-pentaene-4-carboxamide | +++ |
| | 10-[(dimethylamino)methyl]-N-(5-methoxypyridin-3-yl)-7-thia-2,5-diazatricyclo[6.4.0.0²,⁶]dodeca-1(12),3,5,8,10-pentaene-4-carboxamide | ++ |
| | N-(5-methoxypyridin-3-yl)-10-phenyl-7-thia-2,5-diazatricyclo[6.4.0.0²,⁶]dodeca-1(12),3,5,8,10-pentaene-4-carboxamide | +++ |
| | N,5-bis(5-methoxypyridin-3-yl)-1,8,10-triazatricyclo[7.4.0.0²,⁷]trideca-2(7),3,5,8,10,12-hexaene-11-carboxamide | +++ |

TABLE 22-continued

| Structure | IUPAC Name | Activity |
|---|---|---|
| 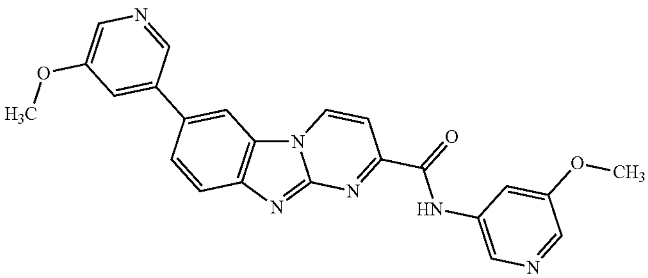 | N,4-bis(5-methoxypyridin-3-yl)-1,8,10-triazatricyclo[7.4.0.0$^{2,7}$]trideca-2(7),3,5,8,10,12-hexaene-11-carboxamide | +++ |
| 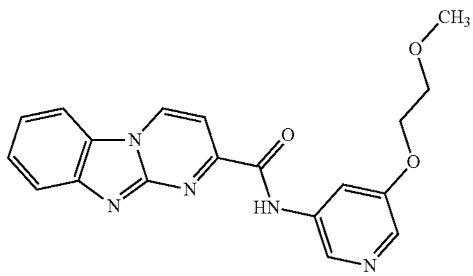 [SMILES: COCCOc1cncc(NC(=O)c2ccn3c(n2)nc2ccccc23)c1] | N-[5-(2-methoxyethoxy)pyridin-3-yl]-1,8,10-triazatricyclo[7.4.0.0$^{2,7}$]trideca-2(7),3,5,8,10,12-hexaene-11-carboxamide | +++ |
| 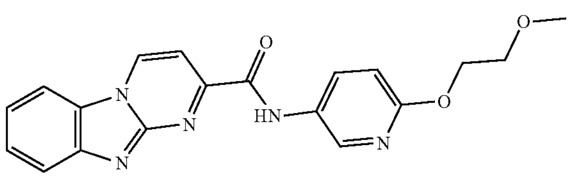 [SMILES: COCCOc1ccc(NC(=O)c2ccn3c(n2)nc2ccccc23)cn1] | N-[6-(2-methoxyethoxy)pyridin-3-yl]-1,8,10-triazatricyclo[7.4.0.0$^{2,7}$]trideca-2(7),3,5,8,10,12-hexaene-11-carboxamide | +++ |

Example B

Binding of tritiated Compound 1 of Method 1 (10-[$^{3}$H]-methoxy-N-(pyridin-3-yl)-7-thia-2,5-diazatricyclo[6.4.0.0$^{2,6}$]dodeca-1(12),3,5,8,10-pentaene-4-carboxamide) to Aβ Aggregates Generation of tritiated compound 1, Method 1, for autoradiography studies was achieved by treating phenolic Compound 2 of Method 2 with tritiated methyl nosylate and a suitable base in N,N-dimethylformamide Purification by HPLC gave the tritiated compound in high radiochemical purity.

Brains were extracted from 12 month old heterozygous APP/PS1 animals (J. Neurochemistry 2009, 108, 1177-1186) and quickly frozen on dry ice in small weigh boats, wrapped with tin foil and stored in zip-lock bags at −80° C. for sectioning. Using a Leica CM3050S cryostat, 20 μm thick sections were generated representing the hippocampus (Bregma −1.34/−3.80) and the cortex/striatum (Bregma 1.54/−0.94). Sections were mounted on poly-Lysine coated slides and instantly dried with a slide warmer.

10-[$^{3}$H]-methoxy-N-(pyridin-3-yl)-7-thia-2,5-diazatricyclo[6.4.0.0$^{2,6}$]dodeca-1(12),3,5,8,10-pentaene-4-carboxamide binding was determined in brain sections of a 12 month old APP/PS1 mouse and a WT littermate. The Aβ aggregate-specific radioligand, $^{3}$H-PiB, was used as a positive control. One slide was used to determine total binding and one slide was used to determine non-specific binding at each radioligand concentration. Non-specific binding was determined for each radioligand in the presence of 1 μM of respective, cold ligand equivalent.

After washing, brain sections were dipped in ice-cold deionized water, and then dried under a stream of cool air. Slides were loaded into the cassette of a Beta-imager 2000, and the images of the brain sections were acquired for 48 hours in zoom mode setting.

Quantification and Analysis: Signal intensity (cpm/mm$^{2}$) was measured for each brain section using Beta Vision+ software. Specific (displaceable) binding, expressed in cpm/mm$^{2}$, was defined by the difference between total and non-specific binding and calculated as follows:

(Total non-specific)/Total×100%.

Statistical Analysis: Statistical significance determined by 2way ANOVA with Tukey's multiple comparisons test (*p<0.05).

Figure 1B:
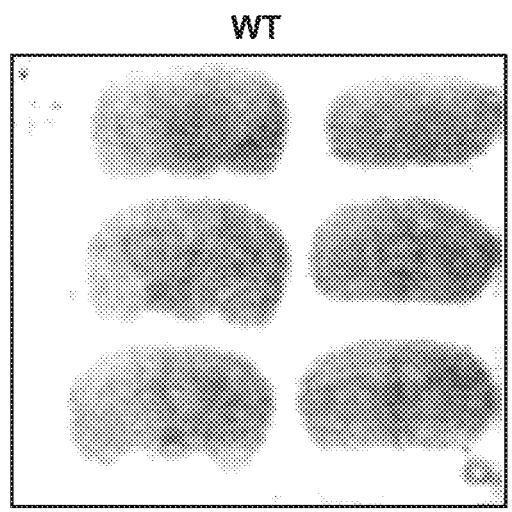
FIG. 1B shows the binding of the same compound in wild type mouse brain.
Figure 2:
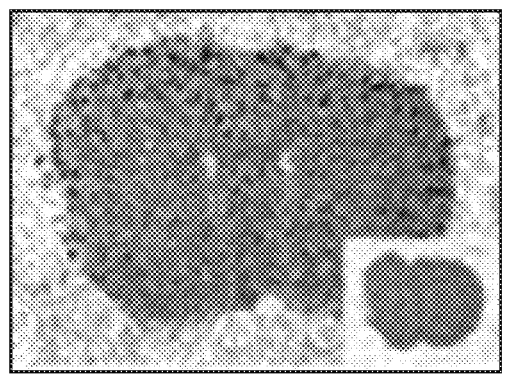
FIG. 2 shows binding of the positive control compound $^3$H-PiB to 18-month old heterozygous APP/PS1 mouse brain.
Figure 4A:
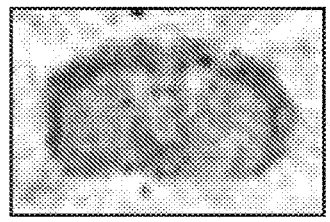
FIG. 4A and FIG. 4B show mHTT aggregates are visible in the 10 week old R6/2 mouse brain after incubation with 0.5 nM 7-methoxy-N-(1-methyl-6-oxo-1,6-dihydro-pyridazin-3-yl)benzo[d]imidazo[2,1-b]thiazole-2-carboxamide (as shown in FIG. 4A) as compared with a wild-type littermate (as shown in FIG. 4B).
Figure 4A:
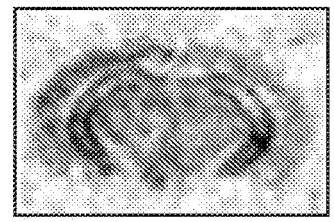
Figure 4A:
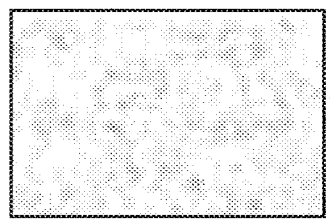
Figure 4A:
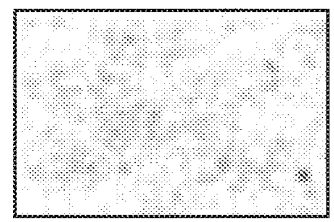
Figure 4B:
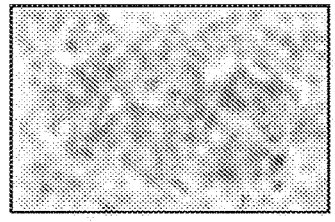
Figure 4B:
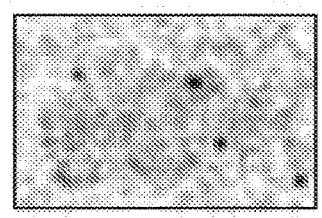
Figure 4B:
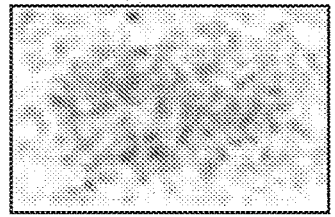
Figure 4B:
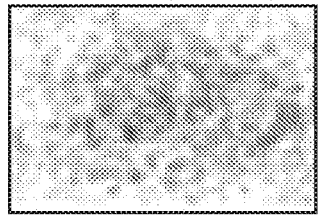

Results: FIG. 1 shows that Aβ aggregates are visible in the 12-month old heterozygous APP/PS1 mouse brain after incubation with 1 nM 10-[$^{3}$H]-methoxy-N-(pyridin-3-yl)-7-thia-2,5-diazatricyclo[6.4.0.0$^{2,6}$]dodeca-1(12),3,5,8,10-pentaene-4-carboxamide (FIG. 1A), as compared with a wild-type littermate (FIG. 1B). Binding of the positive control compound $^{3}$H-PiB to 18-month old heterozygous APP/PS1 mouse brain is shown in FIG. 2. mHTT aggregates are visible in the 10 week old R6/2 mouse brain after incubation with 0.5 nM 7-methoxy-N-(1-methyl-6-oxo-1,6-dihydropyridazin-3-yl)benzo[d]imidazo[2,1-b]thiazole-2-carboxamide (as shown in FIG. 4A) as compared with a wild-type littermate (as shown in FIG. 4B).

Example C

In Vivo Imaging with [¹¹C]-Compound 1 of Method 1 (10-[¹¹C]-methoxy-N-(pyridin-3-yl)-7-thia-2,5-diazatricyclo[6.4.0.0$^{2,6}$]dodeca-1(12),3,5,8,10-pentaene-4-carboxamide) in a Knock-In Model of Huntington's Disease ¹¹C-labeled Compound 1 of Method 1 was evaluated for its ability to penetrate the central nervous system of mice following systemic administration, and its binding to the cerebellum, striatum, hippocampus, and cortex was quantitated. Three groups of animals were compared: wild-type, and mice that were heterozygous or homozygous for the zQ175 knock-in allele. (Menalled L. B. et al. Comprehensive behavioral and molecular characterization of a new knock-in mouse model of Huntington's disease: zQ175. PloS One 2012, 7, e49838). Forty-eight nine months old animals (16 WT, 16 heterozygous and 16 homozygous zQ175) were obtained from The Jackson Laboratory, USA. The animals were housed at the animal department of Karolinska University Hospital in a temperature (±21° C.) and humidity (±40%) controlled environment on a 12 hour light/dark cycle (lights on 7:00 AM) with access to food and water ad libitum. Animals were allowed at least one week to habituate to the animal department before the start of the imaging sessions. All experiments were conducted during the light phase of the cycle.

Animals were anesthetized with inhalation of isoflurane (4-5% isoflurane in oxygen). After induction of anesthesia, the isoflurane concentration was lowered to 1.5-2% in 50/50 air/oxygen and the animals were positioned in the scanner in a designated mouse bed. A cannula was inserted in the tail vein through which the radioligand was administered. A 63-minute dynamic PET scan was initiated immediately upon intravenous injection of the radioligand. Upon completion of the imaging sessions, each animal was returned to its cage.

Image and Statistical Analysis

The acquired list mode data, was reconstructed into 25 timeframes (63 minute scan=4×10 s, 4×20 s, 4×60 s, 7×180 s, 6×360 s). The image reconstruction was made with a fully 3-dimensional maximum-likelihood expectation maximization algorithm (MLEM) with 20 iterations, without scatter and attenuation correction. The reconstructed dynamic PET images were co-registered to an inbuilt mouse MRI template available in PMOD, which also incorporates volumes of interest (VOI's) sets (PMOD Technologies Ltd., Zurich, Switzerland). With the help of these VOI sets, decay corrected time activity curves (TAC) were generated. The regional brain uptake values were expressed as percent standard uptake value (% SUV), which normalizes for injected radioactivity and body weight. In addition, the area under the curve (AUC) was calculated. The selected regions of interest (ROI) were: cortex, hippocampus, striatum and cerebellum.

Figure 3:
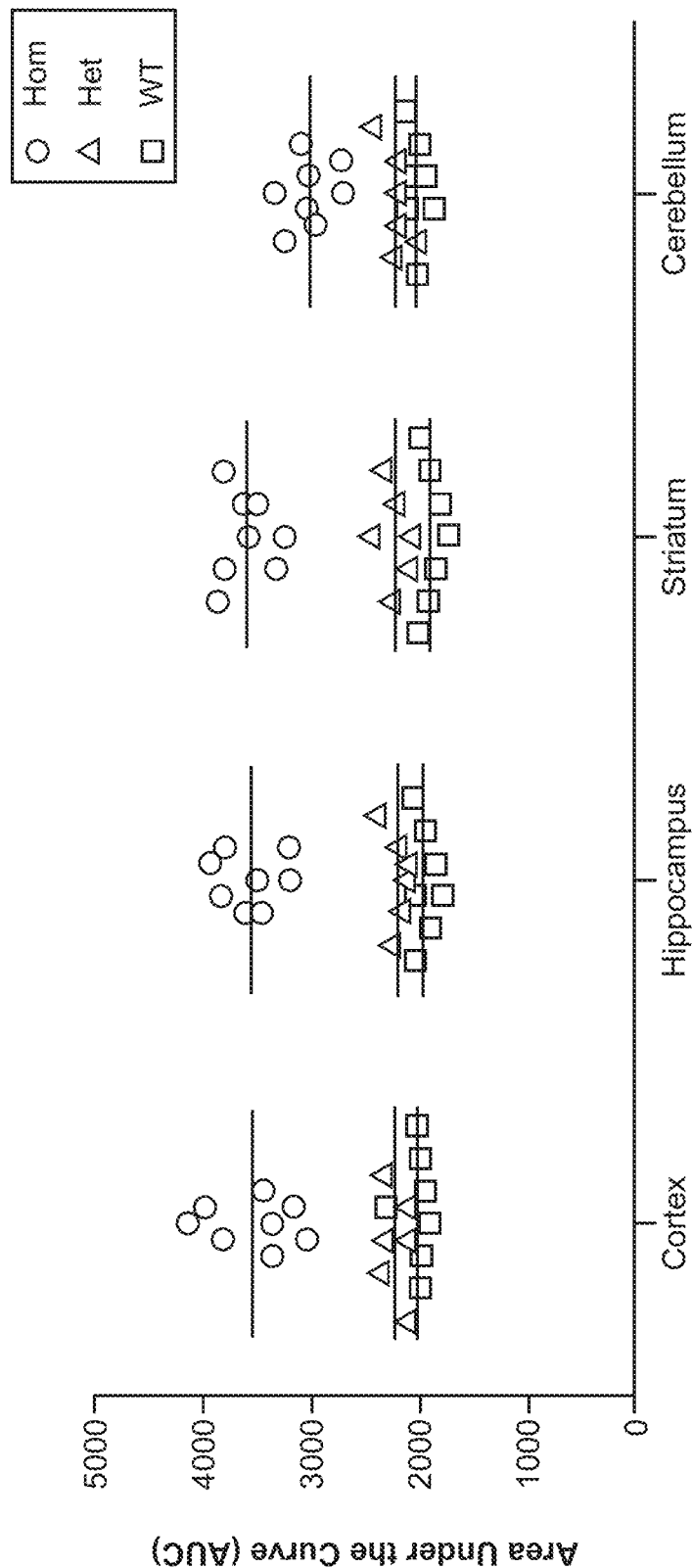
FIG. 3 shows AUC values for binding of 10-[$^{11}$C]-methoxy-N-(pyridin-3-yl)-7-thia-2,5-diazatricyclo[6.4.0.0$^{2,6}$]dodeca-1(12),3,5,8,10-pentaene-4-carboxamide in four regions of the brain in wild type mice and mice that are heterozygous or homozygous for the zQ175 knock-in allele.

The average % SUV and AUC values for the ¹¹C-labeled Compound 1 of Method 1 in the four brain regions, for the three groups of mice, are shown in Table 23. Increased binding of the radioligand, relative to wild type, was observed in all four brain regions in mice which were homozygous for the zQ175 allele. FIG. 3 presents the AUC values for the three groups of animals in the four regions of the brain.

TABLE 23

Average % SUV and AUC values of ¹¹C-labeled Compound 1 of Method 1 in the cortex, hippocampus, striatum and cerebellum of WT, het zQ175 and hom zQ175 animals. Each value is expressed as Mean ± SD

| | % SUV | | | AUC | | |
|---|---|---|---|---|---|---|
| | WT (n = 7) | Het (n = 6) | Hom (n = 8) | WT (n = 7) | Het (n = 6) | Hom (n = 8) |
| Cortex | 67.1 ± 5.7 | 73.4 ± 5.1 | 93.1 ± 9.6 | 2036 ± 131 | 2236 ± 116 | 3542 ± 397 |
| Hippocampus | 73.3 ± 6.5 | 82.0 ± 6.3 | 107.1 ± 10.8 | 1965 ± 101 | 2212 ± 120 | 3570 ± 274 |
| Striatum | 71.9 ± 6.7 | 82.7 ± 7.0 | 107.6 ± 9.6 | 1906 ± 97 | 2243 ± 146 | 3597 ± 231 |
| Cerebellum | 74.1 ± 7.1 | 80.5 ± 6.5 | 92.3 ± 11.3 | 2043 ± 96 | 2219 ± 135 | 3024 ± 221 |

Various modifications, additions, substitutions, and variations to the illustrative examples set forth herein will be apparent to those skilled in the art from the foregoing description. Such modifications are also intended to fall within the scope of the appended claims.

The invention claimed is:
1. A compound of Formula I,

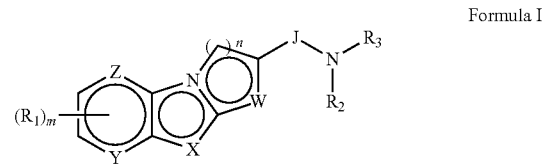

Formula I or a pharmaceutically acceptable salt thereof, wherein
m is 0, 1, or 2;
n is 1 or 2;
J is C(=O) or —CH$_2$—;
X is S or N;
Y is CH or N;
Z is CH or N;
W is N;
for each occurrence, R$_1$ is independently chosen from halo, lower alkoxy, hydroxy, aryl, heteroaryl, or cycloalkoxy, wherein the lower alkoxy, cycloalkoxy, aryl, or heteroaryl are each optionally substituted with one, two, or three groups independently selected from lower alkoxy, alkenyl, —NR$_4$R$_5$, halo, or heteroaryl optionally substituted with one to three lower alkoxy; or R$_1$ is lower alkyl optionally substituted with —NR$_4$R$_5$;
R$_2$ is hydrogen or lower alkyl; and
R$_3$ is pyridin-3-yl, pyridin-3-ylmethyl, 1-benzofuran-5-yl, 1H-pyrazol-4-yl, 6-oxo-1,6-dihydropyridazin-3-yl, pyrimidin-5-yl, 6-oxo-1,6-dihydropyridin-3-yl, pyridin-2-yl, pyridin-4-yl, pyrazin-2-yl, or 2-oxo-1,2-dihydropyrimidin-5-yl, each of which is optionally substituted with one, two, or three groups independently chosen from hydroxy, lower alkoxy optionally substituted with lower alkoxy, lower alkyl optionally substituted with halo, halo, heteroaryl, —(CH$_2$)$_t$NR$_4$R$_5$, cyano, and —C(O)—NR$_4$R$_5$;

t is 0, 1, or 2;

each R$_4$ is independently chosen from hydrogen or lower alkyl;

each R$_5$ is independently chosen from hydrogen or lower alkyl; or

R$_4$ and R$_5$ taken together with the nitrogen to which they are bound form a heterocycloalkyl ring, optionally substituted with one, two, or three groups independently chosen from hydroxy, lower alkoxy, lower alkyl, halo, or —C(O)—NR$_6$R$_7$;

each R$_6$ is independently chosen from hydrogen or lower alkyl; and each R$_7$ is independently chosen from hydrogen or lower alkyl.

2. A compound of claim 1, wherein the compound is of Formula I(a):

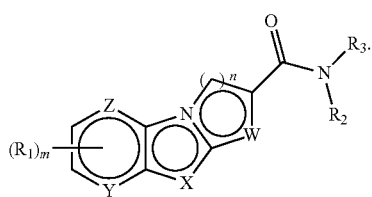

Formula I(a)

3. A compound of claim 1, wherein Y is CH.
4. A compound of claim 1, wherein Y is N.
5. A compound of claim 1, wherein Z is CH.
6. A compound of claim 1, wherein Z is N.
7. A compound of claim 1, wherein the compound is of Formula II(a):

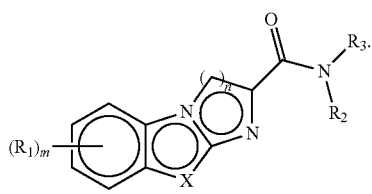

Formula II(a)

8. A compound of claim 1, wherein the compound is Formula II(b):

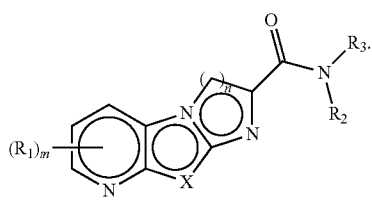

Formula II(b)

9. A compound of claim 1, wherein X is S.
10. A compound of claim 1, wherein X is N.

11. A compound of claim 1, wherein R$_2$ is hydrogen.
12. A compound of claim 1, wherein R$_2$ is methyl.
13. A compound of claim 1, wherein R$_3$ is chosen from pyridin-3-yl, 5-methoxypyridin-3-yl, 6-methoxypyridin-3-yl, 6-fluoropyridin-3-yl, 6-methylpyridin-3-yl, 6-(methylcarbamoyl)pyridin-3-yl, 1-benzofuran-5-yl, 1-methyl-6-oxo-1,6-dihydropyridazin-3-yl, 1-methyl-1H-pyrazol-4-yl, 2-methylpyrimidin-5-yl, 6-(1H-imidazol-1-yl)pyridin-3-yl, 6-oxo-1,6-dihydropyridin-3-yl, 5-(pyridin-3-yl)pyridin-2-yl, 6-(methylcarbamoyl)pyridin-3-yl, 6-oxo-1,6-dihydropyridazin-3-yl, 2-methoxypyridin-4-yl, 5,6-dimethoxypyridin-3-yl, 3-cyanopyridin-4-yl, 3-cyano-2-methoxypyridin-4-yl, 5-methoxypyridin-2-yl, pyridin-4-yl, pyrazin-2-yl, 1-methyl-2-oxo-1,2-dihydropyrimidin-5-yl, 5-(2-methoxyethoxy)pyridin-3-yl, or 6-(2-methoxyethoxy)pyridin-3-yl.

14. A compound of claim 1, wherein n is 1.
15. A compound of claim 1, wherein n is 2.
16. A compound of claim 1, wherein m is 1.
17. A compound of claim 1, wherein m is 2.
18. A compound of claim 16, wherein, for each occurrence, R$_1$ is independently chosen from halo, lower alkoxy, hydroxy, aryl, or heteroaryl, wherein the lower alkoxy, aryl, or heteroaryl are each optionally substituted with one to two groups independently selected from lower alkoxy, alkenyl, —NR$_4$R$_5$, halo, or heteroaryl optionally substituted with one to two lower alkoxy.
19. A compound of claim 16, wherein, for each occurrence, R$_1$ is independently chosen from bromo, methoxy, 2-fluoroethoxy, prop-2-en-1-yloxy, (dimethylamino)methyl, phenyl, 5-methoxypyridin-3-yl, (5-methoxypyridin-2-yl)methoxy, or hydroxy.
20. A compound of claim 1, wherein m is 0.
21. A compound of claim 1, wherein each R$_4$ is independently chosen from hydrogen or C$_{1-3}$alkyl.
22. A compound of claim 1, wherein each R$_5$ is independently chosen from hydrogen or C$_{1-3}$alkyl.
23. A compound of claim 1, wherein each R$_6$ is independently chosen from hydrogen or C$_{1-3}$alkyl.
24. A compound of claim 1, wherein each R$_7$ is independently chosen from hydrogen or C$_{1-3}$alkyl.
25. A compound, or a pharmaceutically acceptable salt thereof, selected from:

10-methoxy-N-(pyridin-3-yl)-7-thia-2,5-diazatricyclo[6.4.0.0$^{2,6}$]dodeca-1(12),3,5,8,10-pentaene-4-carboxamide;

10-methoxy-N-(6-methoxypyridin-3-yl)-7-thia-2,5-diazatricyclo[6.4.0.0$^{2,6}$]dodeca-1(12),3,5,8,10-pentaene-4-carboxamide;

10-methoxy-N-(pyridin-3-ylmethyl)-7-thia-2,5-diazatricyclo[6.4.0.0$^{2,6}$]dodeca-1(12),3,5,8,10-pentaene-4-carboxamide;

10-methoxy-N-methyl-N-(pyridin-3-yl)-7-thia-2,5-diazatricyclo[6.4.0.0$^{2,6}$]dodeca-1(12),3,5,8,10-pentaene-4-carboxamide;

N-(1-benzofuran-5-yl)-10-methoxy-7-thia-2,5-diazatricyclo[6.4.0.0$^{2,6}$]dodeca-1(12),3,5,8,10-pentaene-4-carboxamide;

10-hydroxy-N-(6-methoxypyridin-3-yl)-7-thia-2,5-diazatricyclo[6.4.0.0$^{2,6}$]dodeca-1(12),3,5,8,10-pentaene-4-carboxamide;

N-(6-methoxypyridin-3-yl)-1,8,10-triazatricyclo[7.4.0.0$^{2,7}$]trideca-2(7),3,5,8,10,12-hexaene-11-carboxamide;

N-(6-fluoropyridin-3-yl)-1,8,10-triazatricyclo[7.4.0.0$^{2,7}$]trideca-2(7),3,5,8,10,12-hexaene-11-carboxamide;

10-hydroxy-N-(pyridin-3-yl)-7-thia-2,5-diazatricyclo[6.4.0.0$^{2,6}$]dodeca-1(12),3,5,8,10-pentaene-4-carboxamide;

10-methoxy-N-(5-methoxypyridin-3-yl)-7-thia-2,5-diazatricyclo[6.4.0.0$^{2,6}$]dodeca-1(12),3,5,8,10-pentaene-4-carboxamide;

10-methoxy-N-(1-methyl-1H-pyrazol-4-yl)-7-thia-2,5-diazatricyclo[6.4.0.0$^{2,6}$]dodeca-1(12),3,5,8,10-pentaene-4-carboxamide;

N-(6-fluoropyridin-3-yl)-10-methoxy-7-thia-2,5-diazatricyclo[6.4.0.0$^{2,6}$]dodeca-1(12),3,5,8,10-pentaene-4-carboxamide;

10-methoxy-N-(pyridin-3-yl)-7-thia-2,5,9-triazatricyclo[6.4.0.0$^{2,6}$]dodeca-1(12),3,5,8,10-pentaene-4-carboxamide;

10-methoxy-N-(5-methoxypyridin-3-yl)-7-thia-2,5,9-triazatricyclo[6.4.0.0$^{2,6}$]dodeca-1(12),3,5,8,10-pentaene-4-carboxamide;

10-methoxy-N-[6-(methylcarbamoyl)pyridin-3-yl]-7-thia-2,5-diazatricyclo[6.4.0.0$^{2,6}$]dodeca-1(12),3,5,8,10-pentaene-4-carboxamide;

10-methoxy-4-{1H,2H,3H-pyrrolo[2,3-c]pyridine-1-carbonyl}-7-thia-2,5-diazatricyclo[6.4.0.0$^{2,6}$]dodeca-1(12),3,5,8,10-pentaene;

10-methoxy-N-(6-methylpyridin-3-yl)-7-thia-2,5-diazatricyclo[6.4.0.0$^{2,6}$]dodeca-1(12),3,5,8,10-pentaene-4-carboxamide;

10-methoxy-4-{1-methyl-1H,4H,5H,6H-pyrrolo[3,4-c]pyrazole-5-carbonyl}-7-thia-2,5-diazatricyclo[6.4.0.0$^{2,6}$]dodeca-1(12),3,5,8,10-pentaene;

10-methoxy-N-(1-methyl-6-oxo-1,6-dihydropyridazin-3-yl)-7-thia-2,5-diazatricyclo[6.4.0.0$^{2,6}$]dodeca-1(12),3,5,8,10-pentaene-4-carboxamide;

10-methoxy-N-(2-methylpyrimidin-5-yl)-7-thia-2,5-diazatricyclo[6.4.0.0$^{2,6}$]dodeca-1(12),3,5,8,10-pentaene-4-carboxamide;

N-[6-(1H-imidazol-1-yl)pyridin-3-yl]-10-methoxy-7-thia-2,5-diazatricyclo[6.4.0.0$^{2,6}$]dodeca-1(12),3,5,8,10-pentaene-4-carboxamide;

10-methoxy-N-(pyrimidin-5-yl)-7-thia-2,5-diazatricyclo[6.4.0.0$^{2,6}$]dodeca-1(12),3,5,8,10-pentaene-4-carboxamide;

N-[2-(dimethylamino)ethyl]-10-methoxy-7-thia-2,5-diazatricyclo[6.4.0.0$^{2,6}$]dodeca-1(12),3,5,8,10-pentaene-4-carboxamide;

10-methoxy-N-(2-methoxyethyl)-7-thia-2,5-diazatricyclo[6.4.0.0$^{2,6}$]dodeca-1(12),3,5,8,10-pentaene-4-carboxamide;

10-methoxy-N-(6-oxo-1,6-dihydropyridin-3-yl)-7-thia-2,5-diazatricyclo[6.4.0.0$^{2,6}$]dodeca-1(12),3,5,8,10-pentaene-4-carboxamide;

10-methoxy-N-[5-(pyridin-3-yl)pyridin-2-yl]-7-thia-2,5-diazatricyclo[6.4.0.0$^{2,6}$]dodeca-1(12),3,5,8,10-pentaene-4-carboxamide;

10-methoxy-N-(6-oxo-1,6-dihydropyridazin-3-yl)-7-thia-2,5-diazatricyclo[6.4.0.0$^{2,6}$]dodeca-1(12),3,5,8,10-pentaene-4-carboxamide;

5-methoxy-N-(pyridin-3-yl)-1,8,10-triazatricyclo[7.4.0.0$^{2,7}$]trideca-2(7),3,5,8,10,12-hexaene-11-carboxamide;

N-[6-(methylcarbamoyl)pyridin-3-yl]-1,8,10-triazatricyclo[7.4.0.0$^{2,7}$]trideca-2(7),3,5,8,10,12-hexaene-11-carboxamide;

N-(5-methoxypyridin-3-yl)-1,8,10-triazatricyclo[7.4.0.0$^{2,7}$]trideca-2(7),3,5,8,10,12-hexaene-11-carboxamide;

N-(1-methyl-6-oxo-1,6-dihydropyridazin-3-yl)-1,8,10-triazatricyclo[7.4.0.0$^{2,7}$]trideca-2(7),3,5,8,10,12-hexaene-11-carboxamide;

N-(6-oxo-1,6-dihydropyridin-3-yl)-1,8,10-triazatricyclo[7.4.0.0$^{2,7}$]trideca-2(7),3,5,8,10,12-hexaene-11-carboxamide;

N-(pyridin-3-yl)-1,8,10-triazatricyclo[7.4.0.0$^{2,7}$]trideca-2(7),3,5,8,10,12-hexaene-11-carboxamide;

N-(3-cyanopyridin-4-yl)-1,8,10-triazatricyclo[7.4.0.0$^{2,7}$]trideca-2(7),3,5,8,10,12-hexaene-11-carboxamide;

N-(2-methoxypyridin-4-yl)-1,8,10-triazatricyclo[7.4.0.0$^{2,7}$]trideca-2(7),3,5,8,10,12-hexaene-11-carboxamide;

N-(5,6-dimethoxypyridin-3-yl)-1,8,10-triazatricyclo[7.4.0.0$^{2,7}$]trideca-2(7),3,5,8,10,12-hexaene-11-carboxamide;

5-methoxy-N-(1-methyl-6-oxo-1,6-dihydropyridazin-3-yl)-1,8,10-triazatricyclo[7.4.0.0$^{2,7}$]trideca-2(7),3,5,8,10,12-hexaene-11-carboxamide;

5-methoxy-11-{1-methyl-1H,4H,5H,6H-pyrrolo[3,4-c]pyrazole-5-carbonyl}-1,8,10-triazatricyclo[7.4.0.0$^{2,7}$]trideca-2(7),3,5,8,10,12-hexaene;

4-methoxy-N-(5-methoxypyridin-3-yl)-1,8,10-triazatricyclo[7.4.0.0$^{2,7}$]trideca-2(7),3,5,8,10,12-hexaene-11-carboxamide;

5-methoxy-N-(5-methoxypyridin-3-yl)-1,8,10-triazatricyclo[7.4.0.0$^{2,7}$]trideca-2(7),3,5,8,10,12-hexaene-11-carboxamide;

N-[6-(1H-imidazol-1-yl)pyridin-3-yl]-5-methoxy-1,8,10-triazatricyclo[7.4.0.0$^{2,7}$]trideca-2(7),3,5,8,10,12-hexaene-11-carboxamide;

N-(3-cyanopyridin-4-yl)-5-methoxy-1,8,10-triazatricyclo[7.4.0.0$^{2,7}$]trideca-2(7),3,5,8,10,12-hexaene-11-carboxamide;

N-(6-oxo-1,6-dihydropyridazin-3-yl)-1,8,10-triazatricyclo[7.4.0.0$^{2,7}$]trideca-2(7),3,5,8,10,12-hexaene-11-carboxamide;

N-(3-cyano-2-methoxypyridin-4-yl)-1,8,10-triazatricyclo[7.4.0.0$^{2,7}$]trideca-2(7),3,5,8,10,12-hexaene-11-carboxamide;

5-methoxy-N-(6-methoxypyridin-3-yl)-1,8,10-triazatricyclo[7.4.0.0$^{2,7}$]trideca-2(7),3,5,8,10,12-hexaene-11-carboxamide;

10-methoxy-N-(5-methoxypyridin-2-yl)-7-thia-2,5-diazatricyclo[6.4.0.0$^{2,6}$]dodeca-1(12),3,5,8,10-pentaene-4-carboxamide;

N-(5-methoxypyridin-3-yl)-7-thia-2,5-diazatricyclo[6.4.0.0$^{2,6}$]dodeca-1(12),3,5,8,10-pentaene-4-carboxamide;

10-methoxy-N-(pyridin-4-yl)-7-thia-2,5-diazatricyclo[6.4.0.0$^{2,6}$]dodeca-1(12),3,5,8,10-pentaene-4-carboxamide;

10-methoxy-N-(pyrazin-2-yl)-7-thia-2,5-diazatricyclo[6.4.0.0$^{2,6}$]dodeca-1(12),3,5,8,10-pentaene-4-carboxamide;

3-{10-methoxy-7-thia-2,5-diazatricyclo[6.4.0.0$^{2,6}$]dodeca-1(12),3,5,8,10-pentaene-4-amido}pyridin-1-ium-1-olate;

10-(2-fluoroethoxy)-N-(pyridin-3-yl)-7-thia-2,5-diazatricyclo[6.4.0.0$^{2,6}$]dodeca-1(8),3,5,9,11-pentaene-4-carboxamide;

N-({10-methoxy-7-thia-2,5-diazatricyclo[6.4.0.0$^{2,6}$]dodeca-1(12),3,5,8,10-pentaen-4-yl}methyl)pyridin-3-amine;

10-[(5-methoxypyridin-2-yl)methoxy]-N-(5-methoxypyridin-3-yl)-7-thia-2,5-diazatricyclo[6.4.0.0$^{2,6}$]dodeca-1(12),3,5,8,10-pentaene-4-carboxamide;

N-(1-methyl-6-oxo-1,6-dihydropyridin-3-yl)-1,8,10-triazatricyclo[7.4.0.0$^{2,7}$]trideca-2(7),3,5,8,10,12-hexaene-11-carboxamide;

11-bromo-N-(5-methoxypyridin-3-yl)-7-thia-2,5,9-tri-azatricyclo[6.4.0.0$^{2,6}$]dodeca-1(12),3,5,8,10-pentaene-4-carboxamide;

N-(1-methyl-6-oxo-1,6-dihydropyridazin-3-yl)-10-(prop-2-en-1-yloxy)-7-thia-2,5-diazatricyclo[6.4.0.0$^{2,6}$]do-deca-1(12),3,5,8,10-pentaene-4-carboxamide;

10-methoxy-N-(5-methoxypyridin-3-yl)-5-thia-2,7-di-azatricyclo[6.4.0.0$^{2,6}$]dodeca-1(12),3,6,8,10-pentaene-4-carboxamide;

10-methoxy-N-(1-methyl-6-oxo-1,6-dihydropyridazin-3-yl)-5-thia-2,7-diazatricyclo[6.4.0.0$^{2,6}$]dodeca-1(12),3,6,8,10-pentaene-4-carboxamide;

10-methoxy-N-(2-methylpyrimidin-5-yl)-5-thia-2,7-di-azatricyclo[6.4.0.0$^{2,6}$]dodeca-1(8),3,6,9,11-pentaene-4-carboxamide;

N-(1-methyl-2-oxo-1,2-dihydropyrimidin-5-yl)-1,8,10-triazatricyclo[7.4.0.0$^{2,7}$]trideca-2(7),3,5,8,10,12-hexaene-11-carboxamide;

11-methoxy-N-(5-methoxypyridin-3-yl)-7-thia-2,5,9-tri-azatricyclo[6.4.0.0$^{2,6}$]dodeca-1(12),3,5,8,10-pentaene-4-carboxamide;

11-methoxy-N-(1-methyl-6-oxo-1,6-dihydropyridazin-3-yl)-7-thia-2,5,9-triazatricyclo[6.4.0.0$^{2,6}$]dodeca-1(12),3,5,8,10-pentaene-4-carboxamide;

10-methoxy-N-{3-[(methylamino)methyl]phenyl}-7-thia-2,5-diazatricyclo[6.4.0.0$^{2,6}$]dodeca-1(8),3,5,9,11-pentaene-4-carboxamide;

10-[(dimethylamino)methyl]-N-(5-methoxypyridin-3-yl)-7-thia-2,5-diazatricyclo[6.4.0.0$^{2,6}$]dodeca-1(12),3,5,8,10-pentaene-4-carboxamide;

N-(5-methoxypyridin-3-yl)-10-phenyl-7-thia-2,5-diaza-tricyclo[6.4.0.0$^{2,6}$]dodeca-1(12),3,5,8,10-pentaene-4-carboxamide;

N,5-bis(5-methoxypyridin-3-yl)-1,8,10-triazatricyclo[7.4.0.0$^{2,7}$]trideca-2(7),3,5,8,10,12-hexaene-11-carboxamide;

N,4-bis(5-methoxypyridin-3-yl)-1,8,10-triazatricyclo[7.4.0.0$^{2,7}$]trideca-2(7),3,5,8,10,12-hexaene-11-carboxamide;

N-[5-(2-methoxyethoxy)pyridin-3-yl]-1,8,10-triazatricy-clo[7.4.0.0$^{2,7}$]trideca-2(7),3,5,8,10,12-hexaene-11-carboxamide; and N-[6-(2-methoxyethoxy)pyridin-3-yl]-1,8,10-triazatricy-clo[7.4.0.0$^{2,7}$]trideca-2(7),3,5,8,10,12-hexaene-11-carboxamide.

26. A pharmaceutical composition comprising a compound of claim 1, or a pharmaceutically acceptable salt thereof, and a pharmaceutically acceptable adjuvant, excipient, or diluent.

27. A pharmaceutical composition comprising a compound of claim 25, or a pharmaceutically acceptable salt thereof, and a pharmaceutically acceptable adjuvant, excipient, or diluent.

* * * * *